United States Patent
Blythin et al.

[11] Patent Number: 5,968,929
[45] Date of Patent: Oct. 19, 1999

[54] PIPERAZINO DERIVATIVES AS NEUROKININ ANTAGONISTS

[75] Inventors: David J. Blythin, North Caldwell; Xiao Chen, Edison; Richard J. Friary, Bridgewater; Kevin D. McCormick, Edison; John J. Piwinski, Clinton Township; Neng-Yang Shih, North Caldwell; Ho-Jane Shue, Pine Brook, all of N.J.

[73] Assignee: Schering Corporation, Kenilworth, N.J.

[21] Appl. No.: 08/958,896

[22] Filed: Oct. 28, 1997

Related U.S. Application Data

[60] Provisional application No. 60/029,813, Oct. 30, 1996.

[51] Int. Cl.$^6$ .......................... A61K 31/495; A61K 31/55; C07D 471/08; C07D 487/08

[52] U.S. Cl. .......................... 514/215; 514/216; 514/252; 514/253; 540/580; 540/584; 544/360; 544/362; 544/359; 544/364; 544/365; 544/372; 544/373

[58] Field of Search ...................................... 544/362, 373; 540/580; 514/253, 215

[56] References Cited

U.S. PATENT DOCUMENTS

| | | | |
|---|---|---|---|
| 4,935,419 | 6/1990 | Bjork et al. | 514/231.5 |
| 5,350,852 | 9/1994 | Emonds-Alt et al. | 544/336 |
| 5,607,936 | 3/1997 | Chiang et al. | 514/255 |
| 5,719,156 | 2/1998 | Shue et al. | 514/255 |
| 5,783,579 | 7/1998 | McCormick | 514/255 |
| 5,795,894 | 8/1998 | Shue et al. | 514/253 |
| 5,798,359 | 8/1998 | Shue et al. | 514/255 |

FOREIGN PATENT DOCUMENTS

| | | |
|---|---|---|
| 0 655 442 | 5/1995 | European Pat. Off. . |
| WO 92/20661 | 11/1992 | WIPO . |
| WO 94/13646 | 6/1994 | WIPO . |
| WO 96/34864 | 11/1996 | WIPO . |
| WO 97/08166 | 3/1997 | WIPO . |
| WO 97/22597 | 6/1997 | WIPO . |

OTHER PUBLICATIONS

Kramer et al, Science, vol. 281, pp. 1640–1645, (1998).
Stratton et al, Eur. J. Pharmacol., 250 (1993), pp. R11–R12.
Walsh et al, Psychopharmacology, 121 (1995), pp. 186–191.
Lecci et al, Neuroscience Let., 129(1991), pp. 299–302.
Teixeira et al, Eur. J. Pharmacol., 311 (1996), pp. 7–14.
Picard et al, Eur. J. Pharmacol., 232 (1993), pp. 255–261.
Fleetwood–Walker et al, Eur. J. Pharmacol., 242 (1993), pp. 173–181.
J. Med. Chem., 9 (1966), p. 181, Roderick et al.
Maggi et al, Eur. J. Pharmacol., 166, (1989), pp. 435–440.
Ellis et al, J. Pharmacol. Exp. Ther., 267, 1 (1993), pp. 95–101.
Furchgott, Pharm. Rev., 7 (1955), pp. 183–265.
Arunlakshana et al, Brit. J. Pharmacol., 14, 48 (1959), pp. 48–58.
Danko et al, Pharmacol. Comm., 1, 3 (1992), pp. 203–209.
Firouzubadi et al, Bull. Chem. Soc. Jpn., 56 (1983), p. 914.
Chem. Comm., (1984), p. 874, Mitsui et al.
Frossard et al, Life Sci., 49 (1991), pp. 1941–1953.

Primary Examiner—Emily Bernhardt
Attorney, Agent, or Firm—Anita W. Magatti

[57] ABSTRACT

The invention relates to compounds of the formula

I

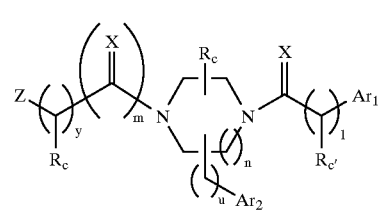

wherein Z, $R_c$, y, m, u, $Ar_2$, n, X, $R_{c'}$, l and $Ar_2$ are as described herein. These compounds are neurokinin antagonists. These compounds are useful in the treatment of chronic airway diseases such as asthma.

6 Claims, No Drawings

PIPERAZINO DERIVATIVES AS NEUROKININ ANTAGONISTS

This application claims the benefit of U.S. Provisional Application No. 60/029813, filed Oct. 30, 1996.

BACKGROUND OF THE INVENTION

The present invention relates to a genus of compounds useful as antagonists of neurokinin receptors. In particular, these can be neurokinin-1 receptor ($NK_1$) antagonists. Some can also be neurokinin-1 receptor ($NK_1$) antagonists and neurokinin-2 receptor ($NK_2$) antagonists, that is, $NK_1/NK_2$ dual receptor antagonists. Some can also be neurokinin-2 receptor ($NK_2$) antagonists. Some can also be neurokinin-3 receptor ($NK_3$) antagonists.

Neurokinin receptors are found in the nervous system and the circulatory system and peripheral tissues of mammals, and therefore are involved in a variety of biological processes. Neurokinin receptor antagonists are consequently expected to be useful in the treatment or prevention of various mammalian disease states, for example pulmonary disorders like asthma, cough, bronchospasm, chronic obstructive pulmonary diseases, and airway hyperreactivity; skin disorders and itch, for example, atopic dermatitis, and cutaneous wheal and flare; neurogenic inflammation inflammatory diseases such as arthritis, migraine, nociception; CNS diseases such as anxiety, Parkinson's disease, movement disorders and psychosis; convulsive disorders, renal disorders, urinary incontinence, ocular inflammation, inflammatory pain, and eating disorders such as food intake inhibition; allergic rhinitis, neurodegenerative disorders, psoriasis, Huntington's disease, depression, emesis and various gastrointestinal disorders such as Crohn's disease.

In particular, $NK_1$ receptors have been reported to be involved in microvascular leakage and mucus secretion, and $NK_2$ receptors have been associated with smooth muscle contraction, making $NK_1$ and $NK_2$ receptor antagonists especially useful in the treatment and prevention of asthma.

Moreover, $NK_3$ receptor antagonists are especially useful in the treatment and prevention of asthma, inflammatory diseases and conditions, such as ocular inflammation, allergic rhinitis, cutaneous wheal and flare, psoriasis, atopic dermatitis, CNS diseases such as anxiety and Parkinson's disease.

SUMMARY OF THE INVENTION

The invention relates to compounds of the formula:

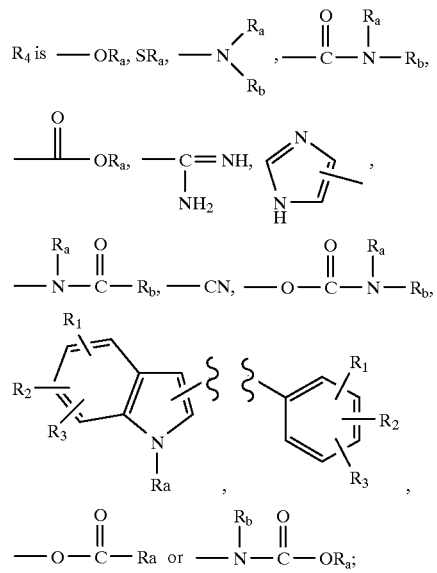

I wherein
each X is independently selected from the group consisting of =O, (H,H), =NRd, and =S;
n is 0 to 2; u is 0 to 2; l is 0 to 2;
m is 1, and y is 1 to 3; or m is 2, and y is 0;
each $R_c$ is independently selected from the group consisting of H, $C_1$–$C_6$ alkyl and —$(CH_2)_{n1}$—$R_4$, wherein $n_1$ is 1 to 6, with the proviso that no more than one $R_c$ is other than H in the

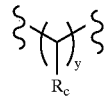

moiety;

$R_d$ is independently selected from the group consisting of H, $C_1$–$C_6$ alkyl, —CN, —$OR_a$, phenyl, substituted phenyl, benzyl, substituted benzyl, or allyl;

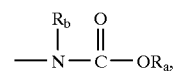

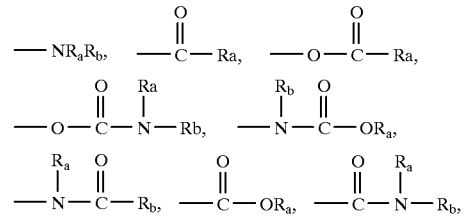

$R_{c'}$ is H, $C_1$–$C_6$ alkyl or $(CH_2)_nOR_a$, with the proviso that no more than one $R_{c'}$ is other than H;

each $R_a$ and $R_b$ is independently selected from the group consisting of H, $C_1$–$C_6$ alkyl, phenyl, substituted phenyl, benzyl, substituted benzyl and allyl; with the proviso that when $R_4$ is $$-N(R_b)-C(=O)-OR_a,$$

$R_a$ is not H; or when $R_a$ and $R_b$ are attached to the same nitrogen, then $R_a$ and $R_b$, together with the nitrogen to which they are attached, can form a 4 to 7 member ring;

each $R_1$ and $R_2$ is independently selected from the group consisting of H, $C_1$–$C_6$ alkyl, —$CF_3$, —$C_2F_5$, Cl, Br, I, F, —$NO_2$, —$OR_a$, —CN, —$NR_aR_b$, —C(O)$R_a$, —O—C(O)$R_a$,
—O—C(O)N($R_a$)$R_b$, —N($R_b$)C(O)$OR_a$,
—N($R_a$)C(O)$R_b$, —C(O)$OR_a$, —C(O)N($R_a$)$R_b$, -continued

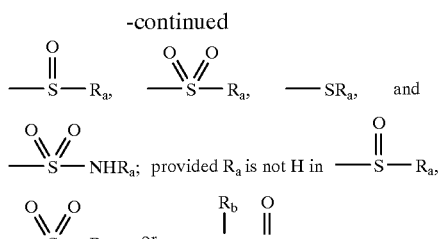

or when $R_1$ and $R_2$ are on adjacent carbons on a ring, they can form

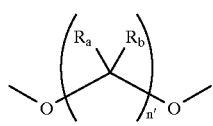

wherein n' is 1 or 2;

each $R_3$ is independently selected from the group consisting of H, $C_1$–$C_6$ alkyl, —$CF_3$, —$C_2F_5$, Cl, Br, I, F, —$OR_a$, —$OCF_3$, phenyl,

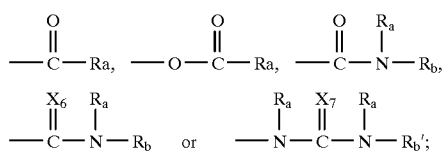

$X_6$ is =S or =$NR_8$;

$R_b'$ is $R_b$ or —$OR_b$;

$R_8$ is $R_m$, —$OR_m$, —$O(CH_2)_{n10}$—$R_k$ or —$O(CH_2)_{n11}$—$R_n$;

$R_m$ is $R_a$ or heteroaryl;

$R_k$ is $R_m$, —$OR_m$, —$SO_3H$, —$PO_3H$ or

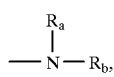

and $n_{10}$ is 2–4;

$R_n$ is CN or

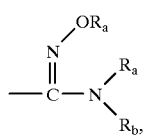

and $n_{11}$ is 1–4;

$X_7$ is =O, =S, =$NR_a$ or =N—$OR_a$;

$Ar_1$ is heteroaryl or substituted heteroaryl,

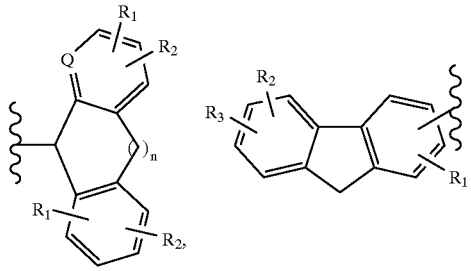

Q is =N— or =CH—;

$Ar_2$ is heteroaryl, substituted heteroaryl,

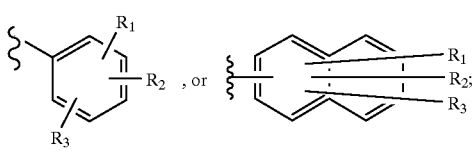

Z is

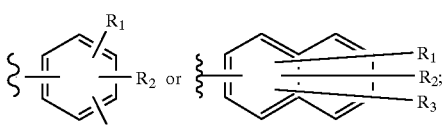

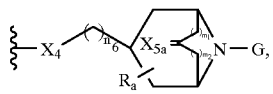

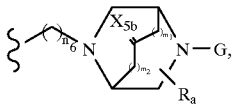

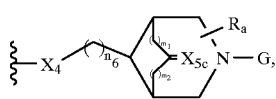

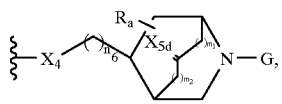

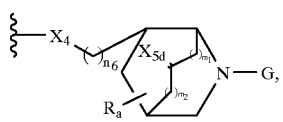

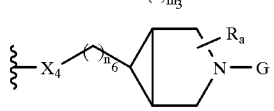

$m_1$ and $m_2$ are independently 0 or 1;

$m_3$ is 1, 2 or 3;

$n_6$ is 0 to 2;

$X_4$ and $X_{4a}$ are —O—, —S— or $$-\underset{(R_5)_{n_5}}{N}-;$$

$X_{5a}$, $X_{5b}$, $X_{5c}$ and $X_{5d}$ are =O, =S, =NO—$R_a$, (H,—$R_a$), (—$OR_a$, —$R_a$), =CH—$R_a$ or =CH—$R_4$;

G is $n_3$ is 0 to 4;

$X_8$ is —$OR_m$, —$SR_m$, halogen, —O—(CH$_2$)$_{n10}$—$R_k$, —O—(CH$_2$)$_{n11}$—$R_n$, —S—(CH$_2$)$_{n10}$—$R_k$ or —S—(CH$_2$)$_{n11}$—$R_n$;

$R_g$ is H, C$_1$–C$_6$ alkoxy, C$_1$–C$_6$ alkyl, C$_3$–C$_8$ cycloalkyl, substituted C$_3$–C$_8$ cycloalkyl, substituted heterocycloalkyl, heterocycloalkyl, aryl, substituted aryl, heteroaryl, substituted heteroaryl, —NR$_a$R$_b$, —O—(CR$_a$,R$_b$)$_{n7}$-aryl, —O—(CR$_a$,R$_b$)$_{n7}$-substituted aryl, —O—(CR$_a$,R$_b$)$_{n7}$-heteroaryl, —O—(CR$_a$,R$_b$)$_{n7}$-substituted heteroaryl, —NR$_a$—(CR$_a$,R$_b$)$_{n7}$-heteroaryl, —NR$_a$—(CR$_a$,R$_b$)$_{n7}$-substituted heteroaryl, —O—(CR$_a$,R$_b$)$_{n7}$-heterocycloalkyl, —O—(CR$_a$,R$_b$)$_{n7}$-substituted heterocycloalkyl, —NR$_a$—(CR$_a$, R$_b$)$_{n7}$-aryl, —NR$_a$—(CR$_a$,R$_b$)$_{n7}$-substituted aryl, —NR$_a$—(CR$_a$,R$_b$)$_{n7}$-heterocycloalkyl or —NR$_a$—(CR$_a$,R$_b$)$_{n7}$-substituted heterocycloalkyl;

$R_h$ is H, C$_1$–C$_6$ alkyl, —C(O)R$_a$, —C(O)NR$_a$R$_b$, —C(O)OR$_a$, —C(O)CH(N(R$_a$)(R$_b$))—R$_7$, —SO$_2$R$_m$, —(CH$_2$)$_{n10}$—R$_k$, —(CH$_2$)$_{n11}$—R$_n$, provided that when $R_h$ is —C(O)OR$_a$, Ra is not H;

$R_i$ is —CN or —R$_a$;

$n_7$ is 0 to 4;

each $R_e$ and $R_f$ is independently selected from the group consisting of H, C$_1$–C$_6$ alkyl, phenyl, substituted phenyl, benzyl, substituted benzyl and allyl;

$n_5$ is 1 to 2;

each $R_5$ is independently selected from the group consisting of H, $$-\text{OH}, \quad -\overset{\overset{O}{\|}}{C}-Ra,$$

C$_1$–C$_6$ alkyl and —(CH$_2$)$_{n1}$—R$_4$, wherein $n_1$ is 1 to 6, with the proviso that when $n_1$ is 1, $R_4$ is not —OH or —NR$_a$R$_b$; also with the proviso that when $n_5$ is 2, $R_5$ is C$_1$–C$_6$ alkyl, and two $R_5$ groups can be attached to the nitrogen to form a quaternary salt;

$R_6$ is H, C$_1$–C$_6$ alkyl, C$_3$–C$_8$ cycloalkyl, substituted C$_3$–C$_8$ cycloalkyl, heteroaryl, substituted heteroaryl, heterocycloalkyl, substituted heterocycloalkyl, wherein $X_3$ is not (H, H) when $n_3$ is 1, $X_3$ is (H,H), =O, =NR$_d$, or =S;

$n_8$ is 0, 1 or 2; $n_9$ is 1 or 2;

$R_7$ is

-continued

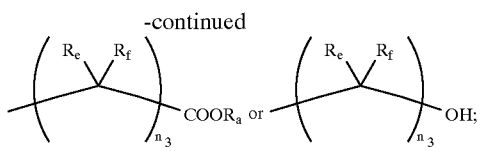

provided that when $X_4$ is

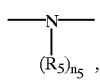

$X_{5a}$ is (H, H) and the sum of $m_1$ plus $m_2$ is 1 or 2, G is not

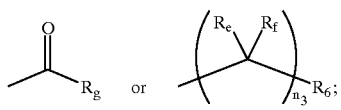

provided that when $X_{5b}$ is (H, H), $m_1$ is 0 or 1 and $m_2$ is 0, G is not

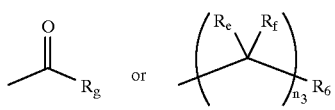

when $R_3$ is H, $C_1$–$C_6$ alkyl, —$CF_3$, —$C_2F_5$, Cl, Br, I, F, —$OR_a$, —$OCF_3$, phenyl,

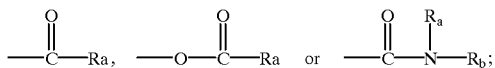

and provided that when $X_{4a}$ is

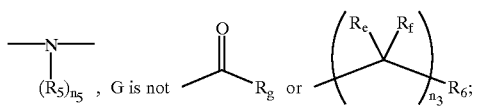

or any enantiomer or diastereomer thereof, or a pharmaceutically acceptable salt thereof.

All of the variables in the above formulas such as Z, $R_1$, $R_2$, and $R_3$, have the same meaning throughout the specification unless otherwise specified.

Preferred compounds of the invention are compounds of formula I wherein each X is =O or (H, H) and at least one X is =O.

Also preferred are compounds of formula I wherein each X is =O.

Also preferred are compounds of formula I wherein l is 0, m is 1, n is 1, u is 0 and y is 1–3.

Also preferred are compounds of formula I wherein $Ar_1$ is

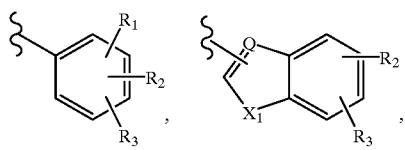

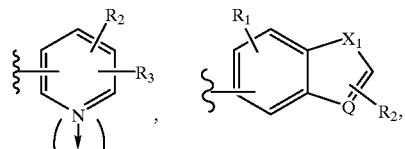

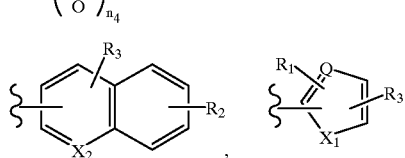

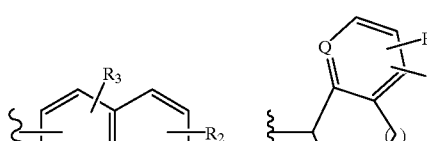

or 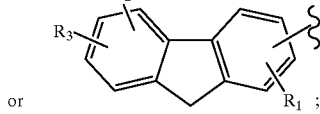 ;

wherein

Q is =N— or =CH—;

each $X_1$ is independently —O—, —S— or —$NR_a$—;

each $X_2$ is independently =CH— or —N=; and $n_4$ is 0 or 1; and $Ar_2$ is

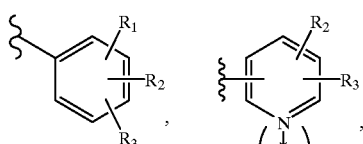

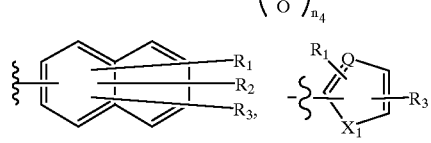

or 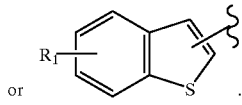 .

Also preferred are compounds of formula I wherein Z is

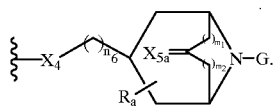

Also preferred are compounds of formula I wherein Z is

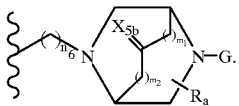

Also preferred are compounds of formula I wherein Z is

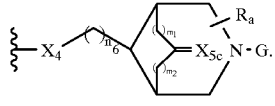

Also preferred are compounds of formula I wherein Z is

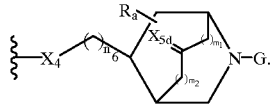

Also preferred are compounds of formula I wherein Z is

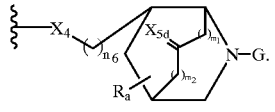

Also preferred are compounds of formula I wherein Z is

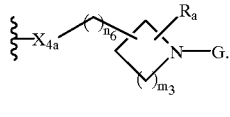

Also preferred are compounds of formula I wherein Z is

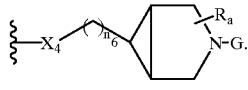

Also preferred are compounds of formula I wherein each X is =O; I is 0; m is 1; y is 1–3; n is 1; u is 0; $Ar_1$ is

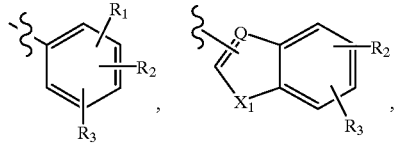

or $Ar_2$ is

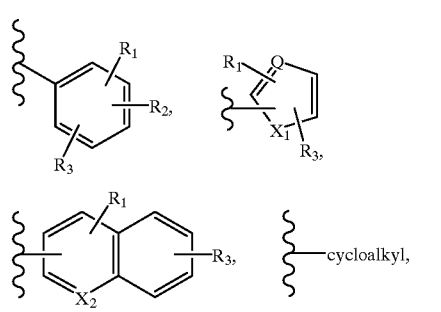

wherein $n_4$ is 0 or 1; Z is as defined in Formula I; $R_e$ and $R_f$ are H, $C_1$–$C_6$ alkyl or allyl; $R_6$ is

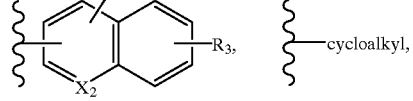

-continued
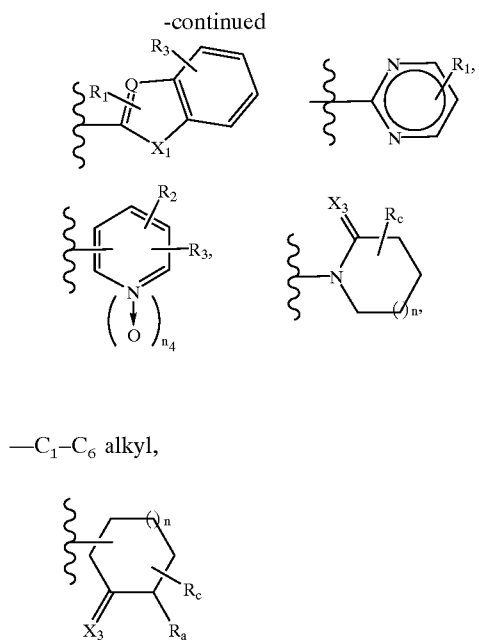
—$C_1$–$C_6$ alkyl,
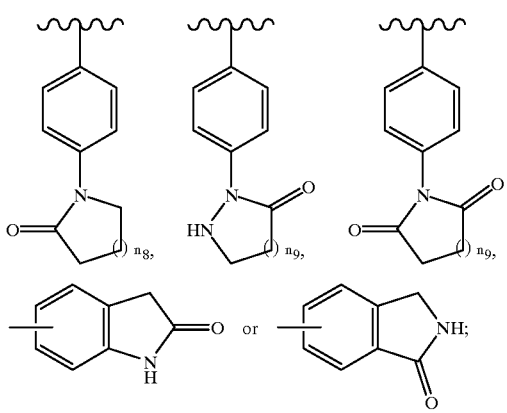
wherein $X_3$ is not (H,H) when $n_3$ is 1,
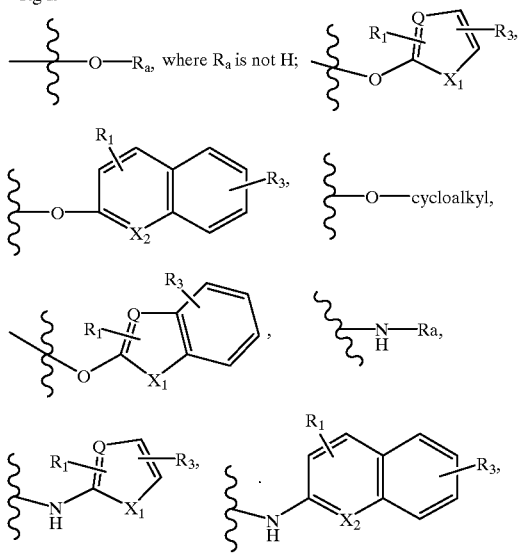
Rg is
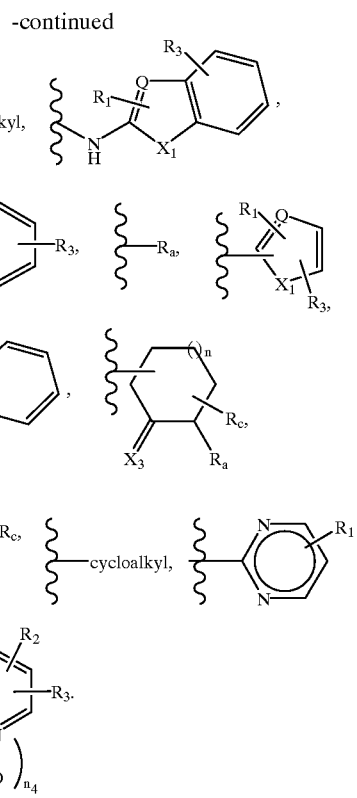
-continued
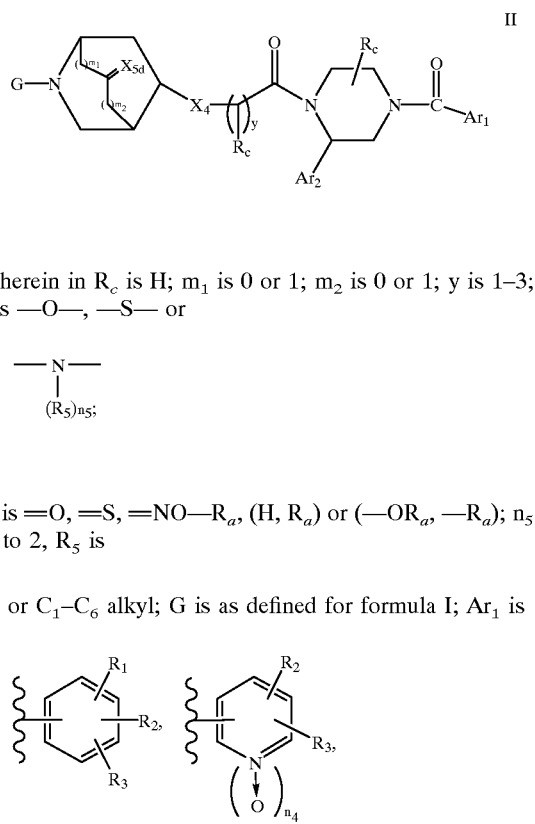
Also preferred are compounds of formula II
wherein in $R_c$ is H; $m_1$ is 0 or 1; $m_2$ is 0 or 1; y is 1–3; $X_4$ is —O—, —S— or
$$-\underset{(R_5)_{n_5}}{N}-;$$
$X_{5d}$ is =O, =S, =NO—$R_a$, (H, $R_a$) or (—O$R_a$, —$R_a$); $n_5$ is 1 to 2, $R_5$ is
H or $C_1$–$C_6$ alkyl; G is as defined for formula I; $Ar_1$ is -continued

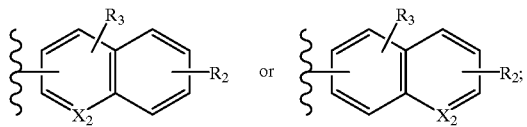

and Ar$_2$ is

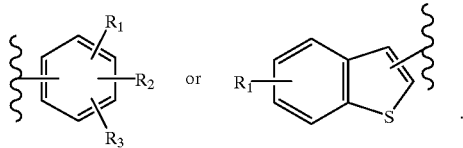

All enantiomers and diastereomers are included.

Also preferred are compounds of the invention of the formula III:

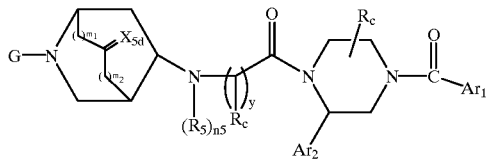

III wherein G is as defined for formula I and Ar$_1$, Ar$_2$, R$_c$, y, R$_5$, n$_5$, m$_1$, m2 and X$_{5d}$ are as defined for formula II.

Also preferred are compounds of the invention of formula III wherein X$_{5d}$ is (H, H) and R$_e$ and R$_f$ are each H.

Also preferred are compounds of the invention of the formula IIIA:

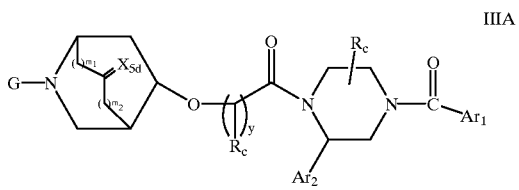

IIIA wherein G is as defined for formula I and Ar$_1$, Ar$_2$, R$_c$, y, m$_1$, m$_2$ and X$_{5d}$ are as defined for formula II.

Also preferred are compounds of the invention of formula IIIA wherein X$_{5d}$ is (H, H) and R$_e$ and R$_f$ are each H.

Also preferred are compounds of the invention of formula IV

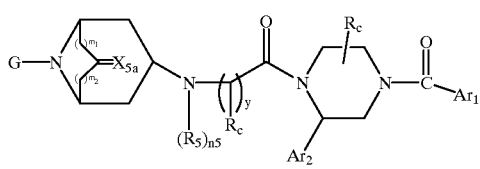

IV wherein Ar$_1$, Ar$_2$, R$_c$, y, R$_5$, n$_5$, m$_1$ and m$_2$ are as defined for formula II, X$_{5a}$ is =O, =S, =NO—R$_a$, (H, R$_a$) or (—OR$_a$, —R$_a$); and G is

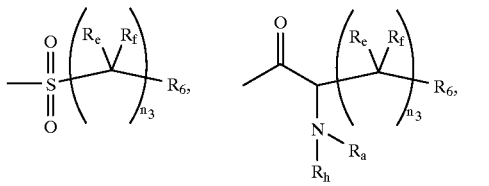

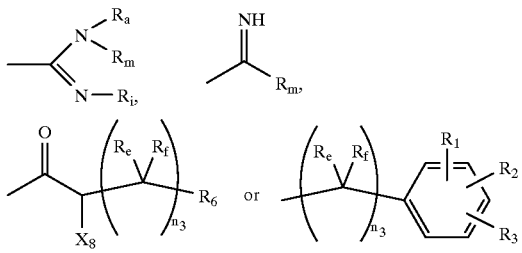

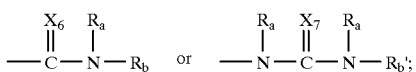

wherein R$_3$ is.

Also preferred are compounds of the invention of formula IV wherein X$_{5a}$ is (H, H) and R$_e$ and R$_f$ are each H.

Also preferred are compounds of the invention of formula IVA

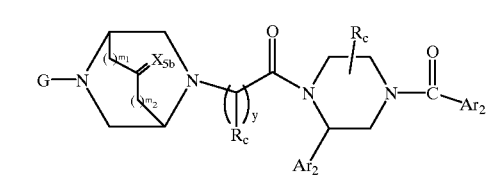

IVA wherein Ar$_1$, Ar$_2$, R$_c$, y, m$_1$ and m$_2$ are as defined for formula II, X$_{5a}$ is =O, =S, =NO—R$_a$, (H, R$_a$) or (—OR$_a$, —R$_a$); and G is as defined for formula I.

Also preferred are compounds of the invention of formula IVA wherein X$_{5a}$ is (H, H) and R$_e$ and R$_f$ are each H.

Also preferred are compounds of the invention of formula V

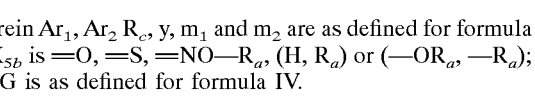

V wherein Ar$_1$, Ar$_2$ R$_c$, y, m$_1$ and m$_2$ are as defined for formula II; X$_{5b}$ is =O, =S, =NO—R$_a$, (H, R$_a$) or (—OR$_a$, —R$_a$); and G is as defined for formula IV.

Also preferred are compounds of formula V wherein X$_{5b}$ is (H, H) and R$_e$ and R$_f$ are each H.

Also preferred are compounds of the invention of formula VI

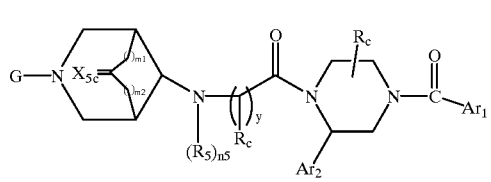

wherein G is as defined for formula I; $Ar_1$, $Ar_2$ $R_c$, $n_5$, $R_5$, y, $m_1$ and $m_2$ are as defined for formula II; and $X_{5c}$ is =O, =S, =NO—$R_a$, (H, $R_a$) or (—$OR_a$, —$R_a$).

Also preferred are compounds of formula VI wherein $X_{5c}$ is (H, H) and $R_e$ and $R_f$ are each H.

Also preferred are compounds of the invention of formula VII

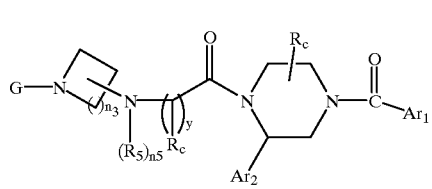

wherein $Ar_1$, $Ar_2$ $R_c$, $n_5$, $R_5$ and y are as defined for formula II and G is as defined for formula IV.

Preferred are compounds of formula VII wherein $n_3$ is 2, i.e., those having the partial formula

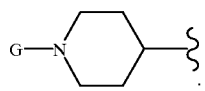

Also preferred are compounds of formula VII wherein $R_e$ and $R_f$ are each H.

Also preferred are compounds of the invention of formula VIII

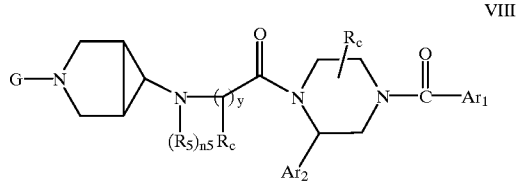

wherein $Ar_1$, $Ar_2$ $R_c$, $n_5$, $R_5$, y and G are as defined for formula II.

Also preferred are compounds of formula VIII wherein $R_e$ and $R_f$ are each H.

Exemplary compounds of the invention are compounds of the formulas:

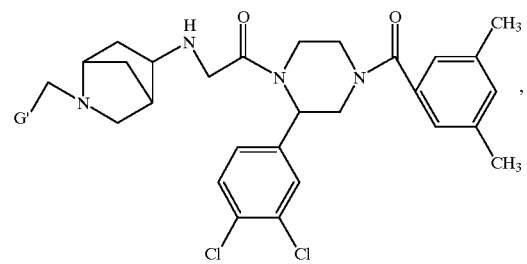

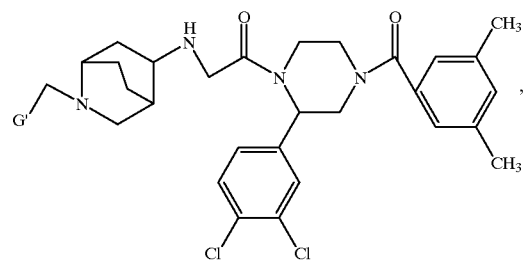

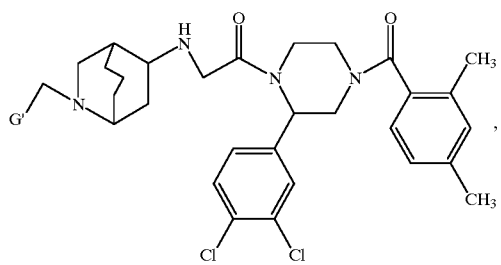

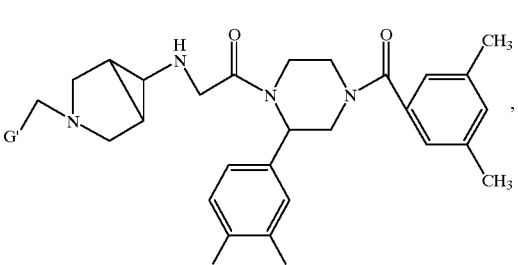

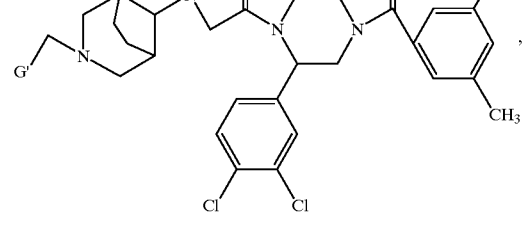

-continued
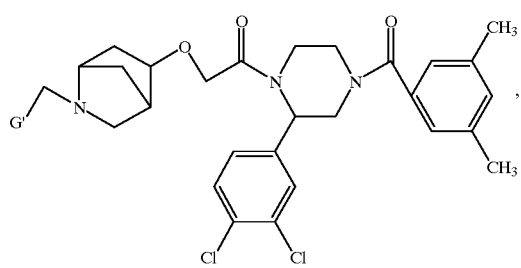,
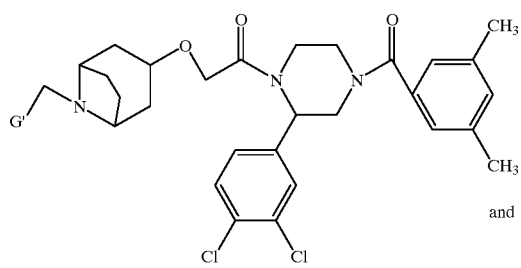 and
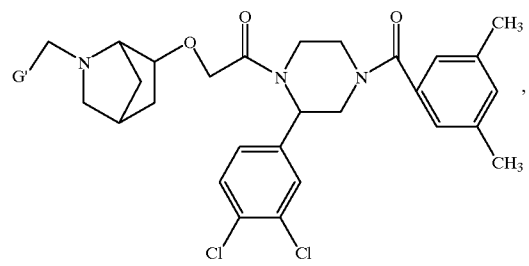,
wherein G' is represented by the following formulas:
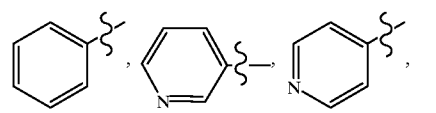
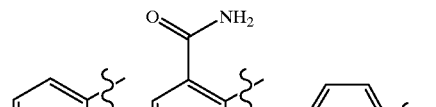
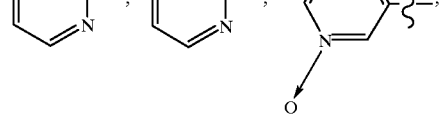
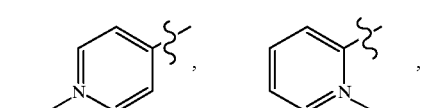
-continued
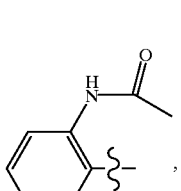, 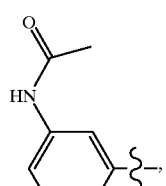,
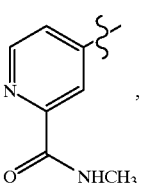 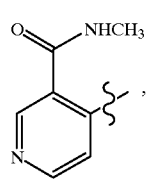,
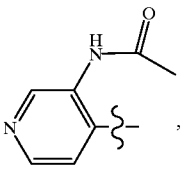,
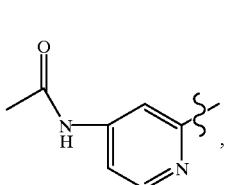,
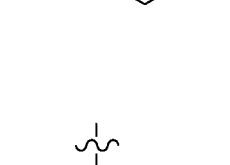,
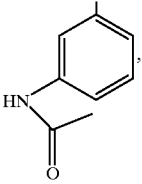, 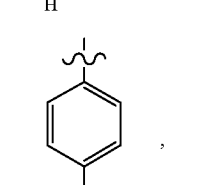
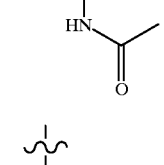, 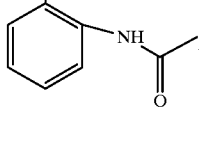
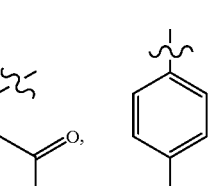
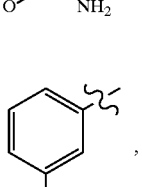,
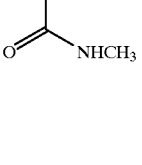

-continued
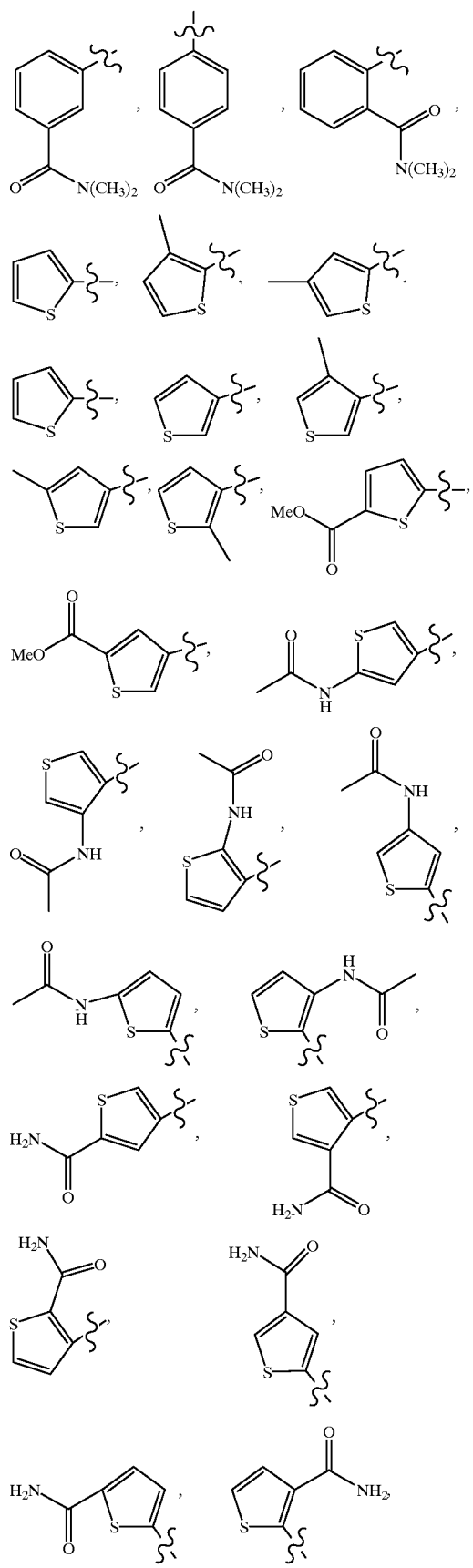
-continued
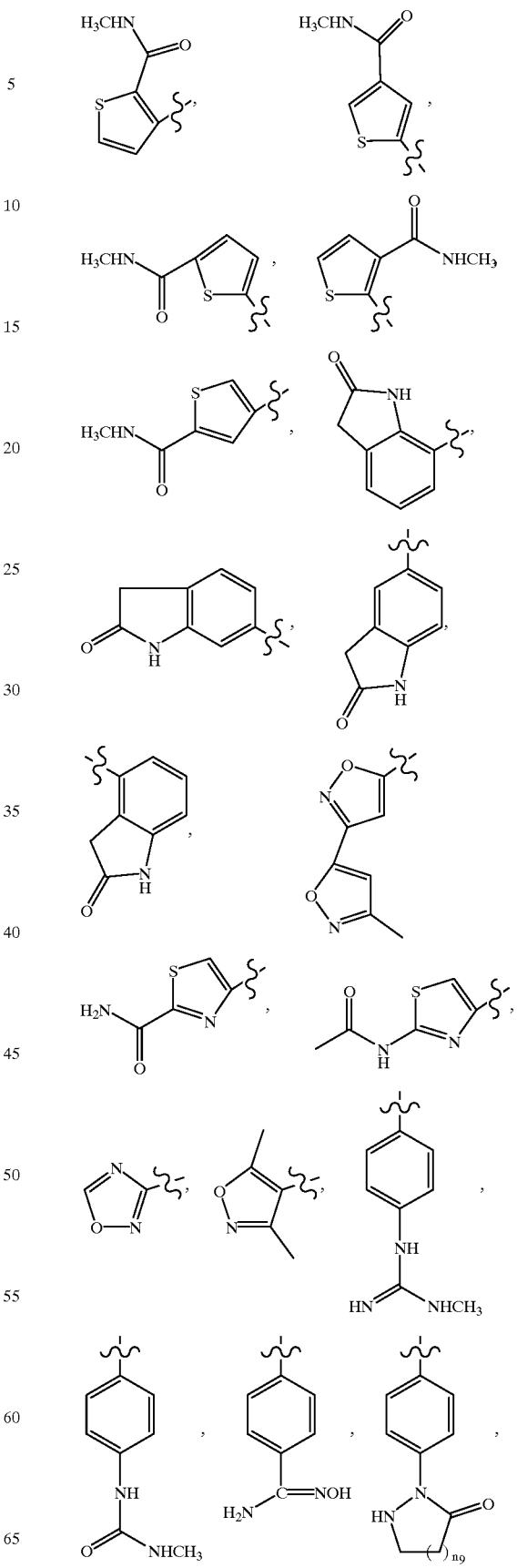

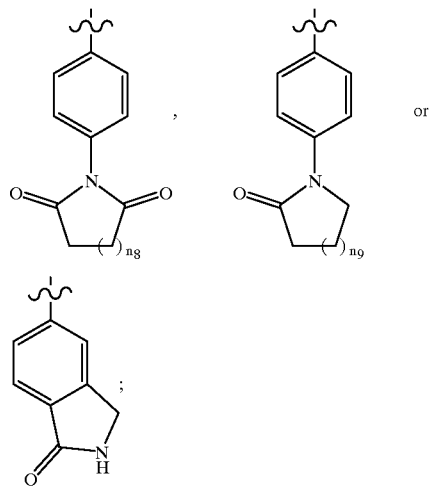
compounds of the formulas
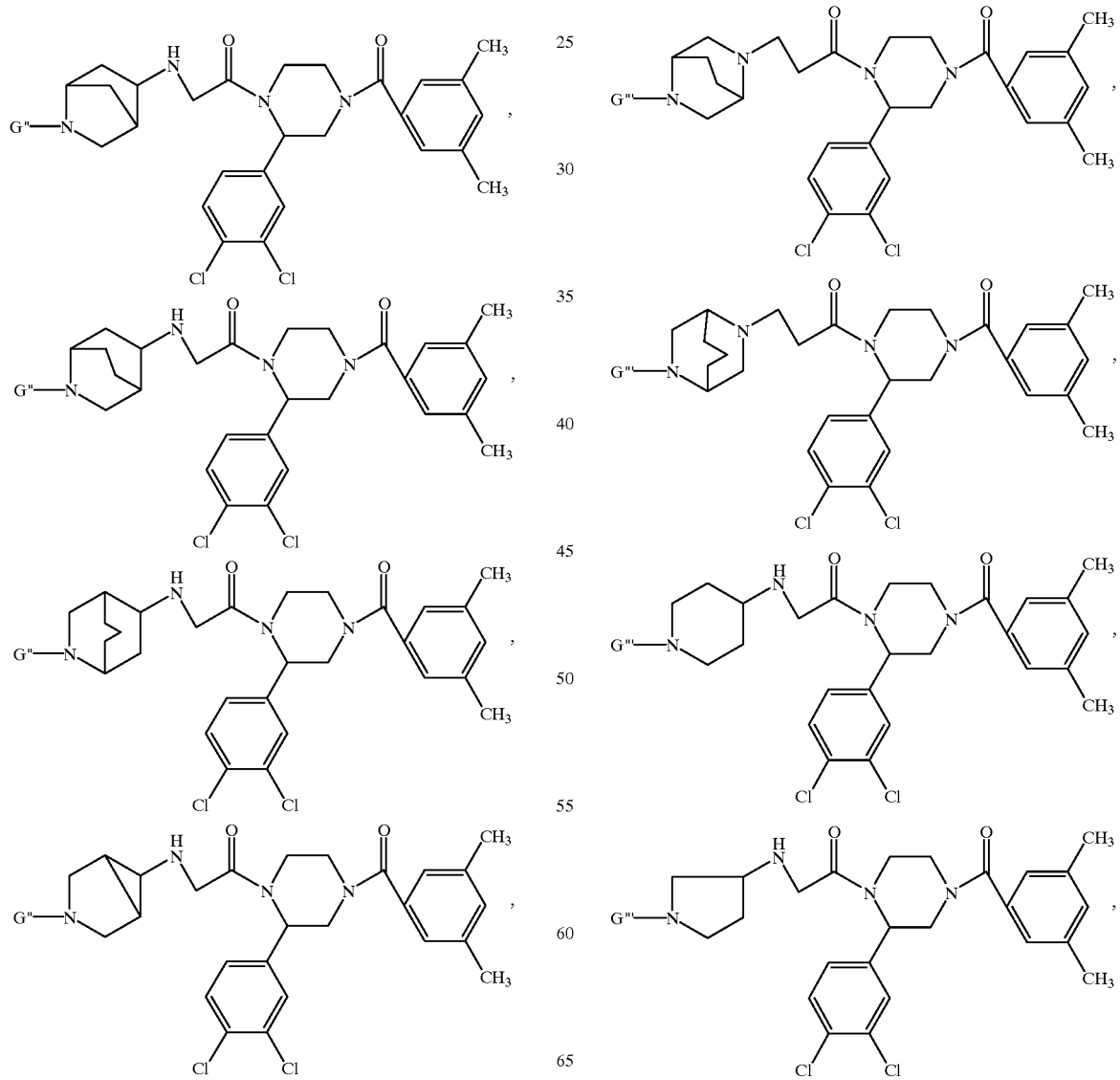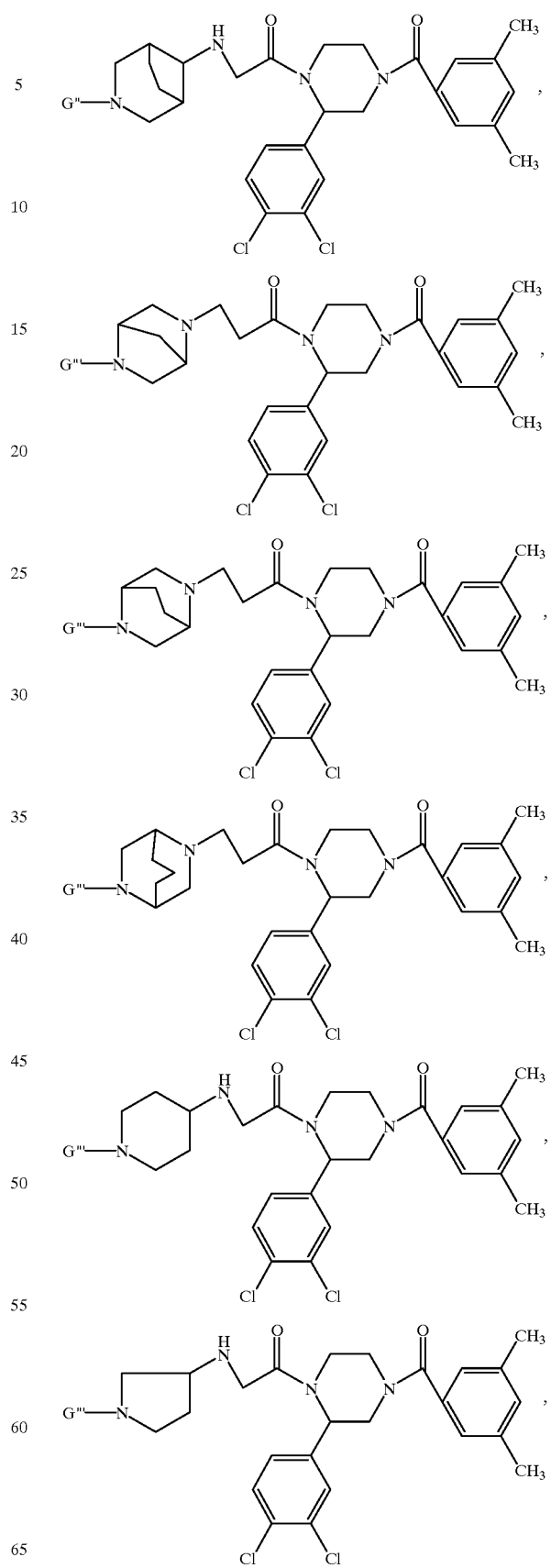

-continued
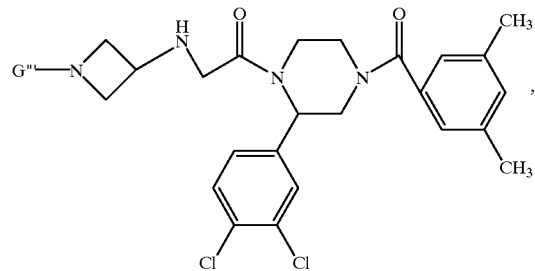
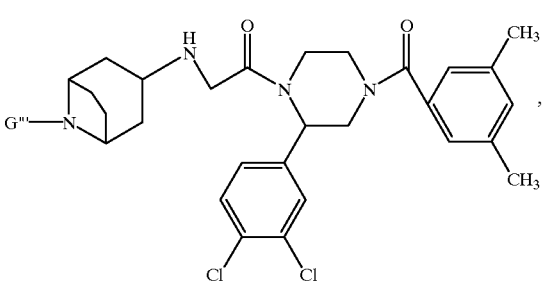
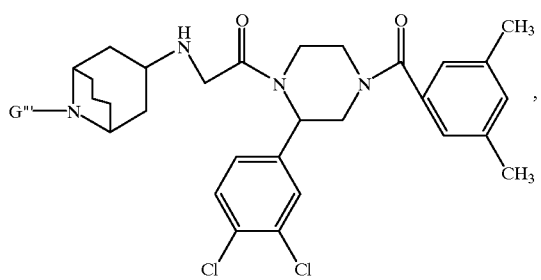
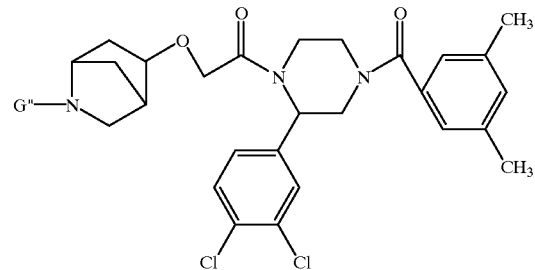
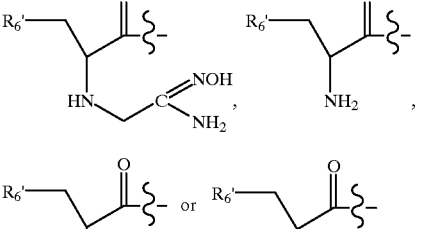
wherein G" and G'" are represented by the formulas:
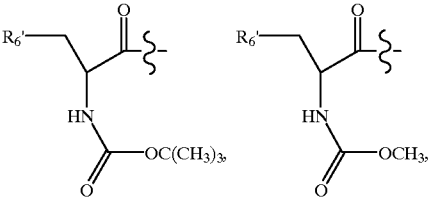
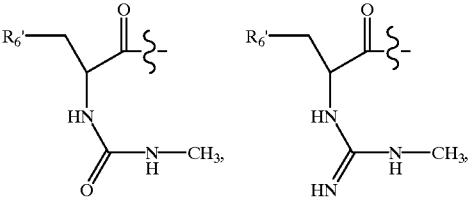
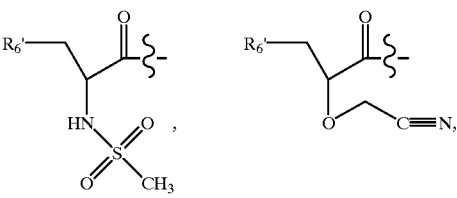
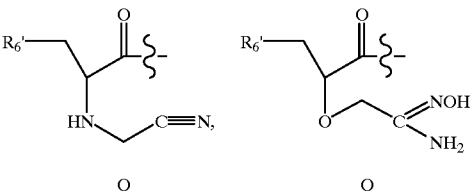
and
wherein $R_6'$ is
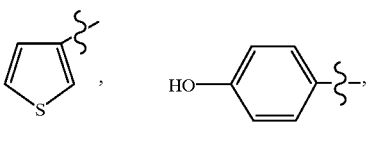
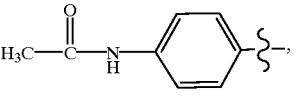
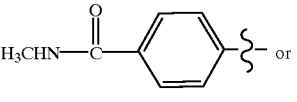 or

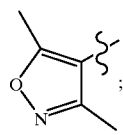
or G" and G'" are represented by the formulas:
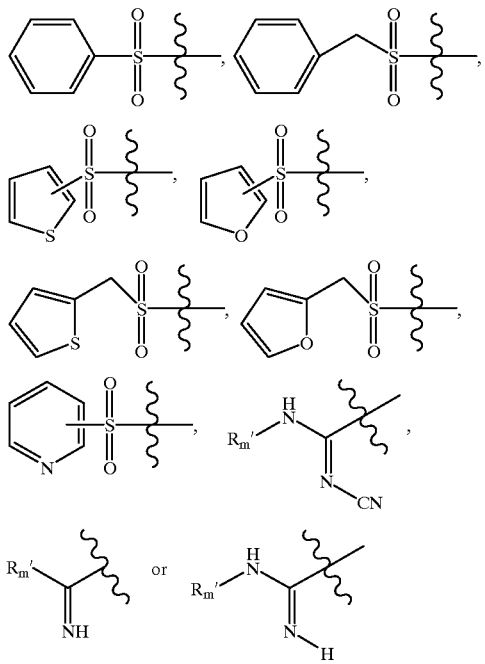
wherein $R_m'$ is represented by the formulas:
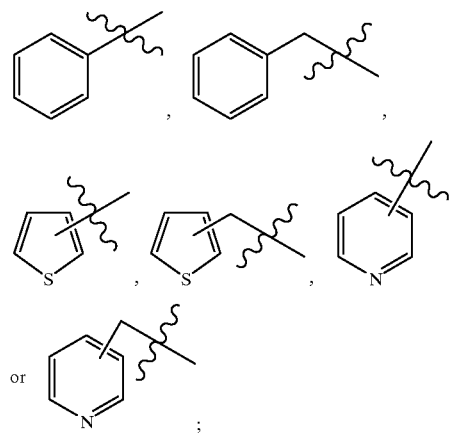
and wherein G" also is:
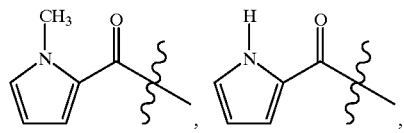
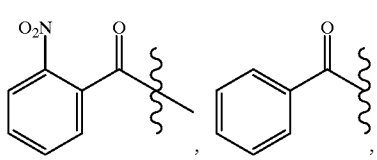
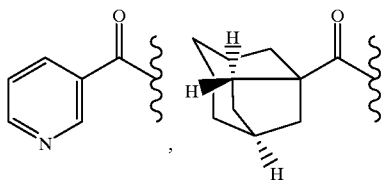
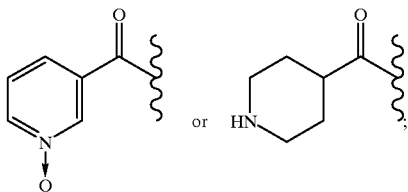
and wherein G'" also is:
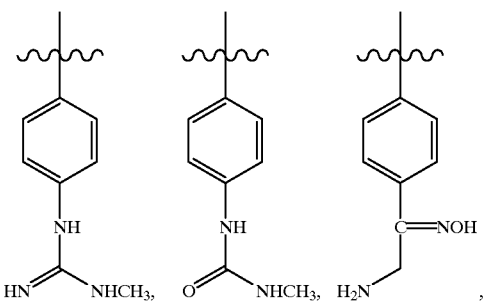
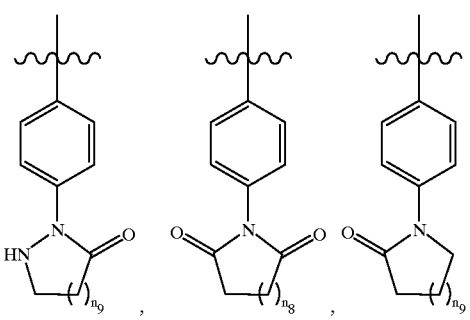
or
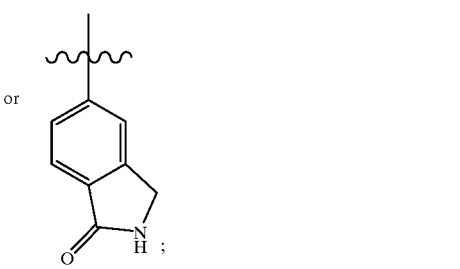

or a compound of the formula
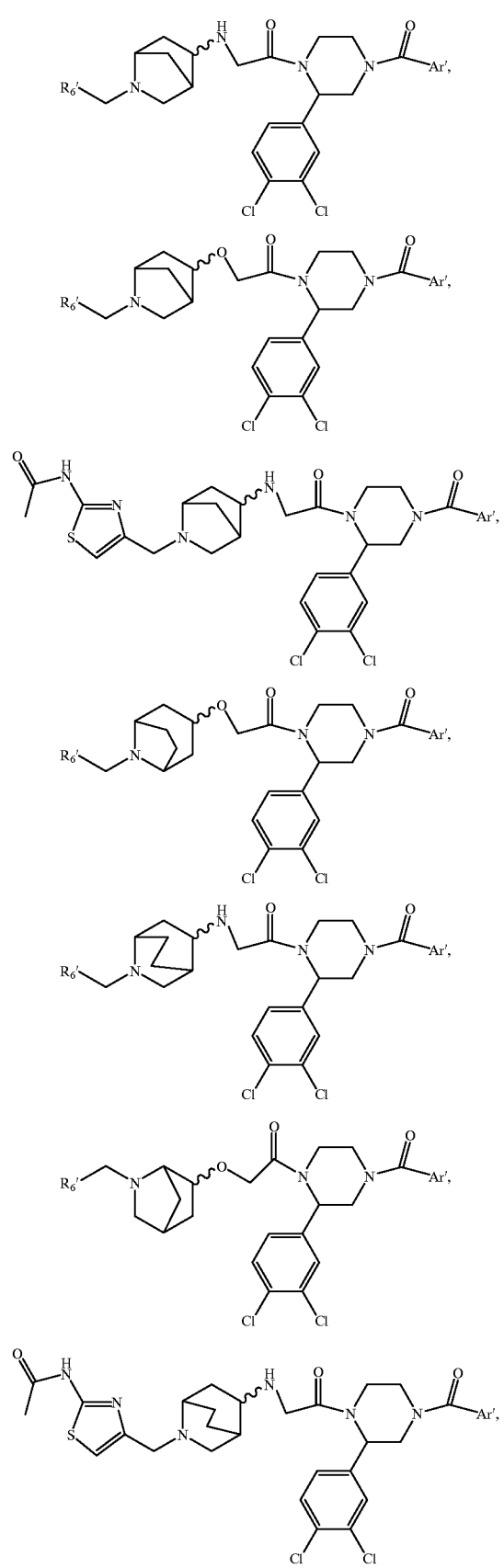
-continued
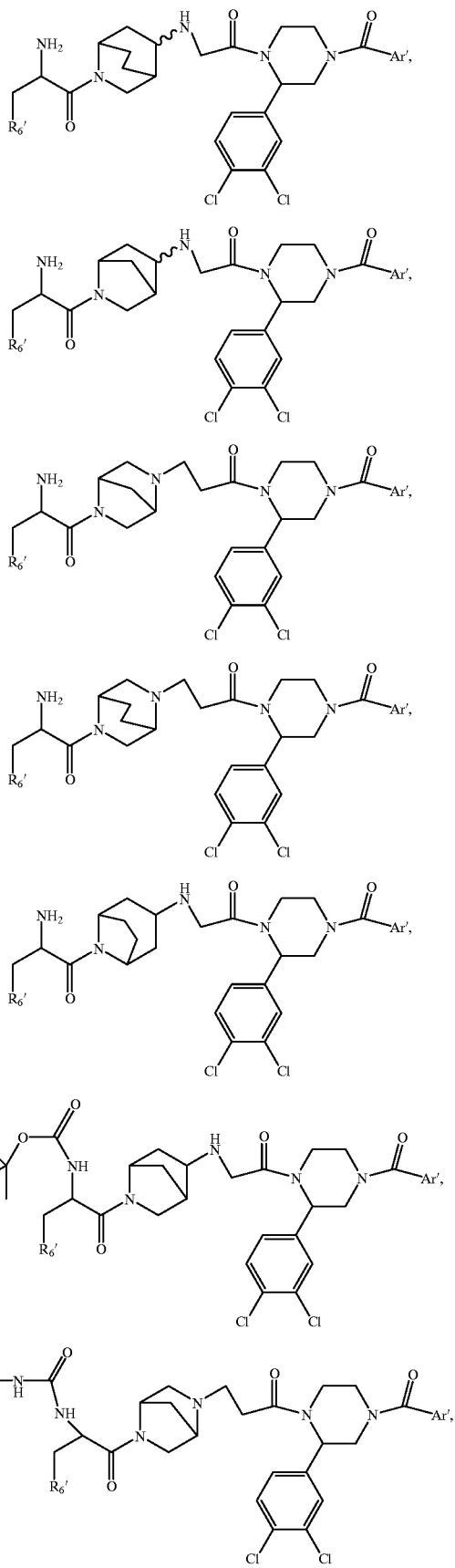

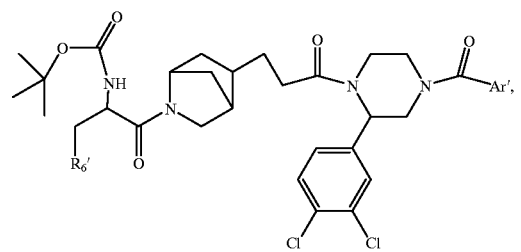
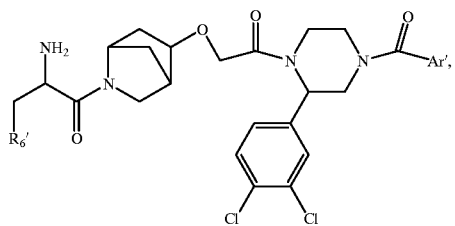
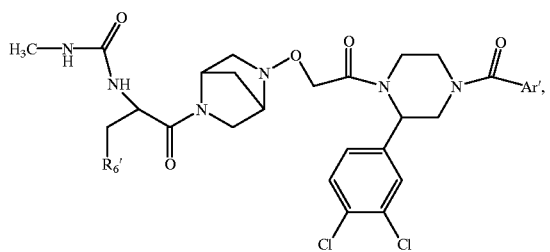
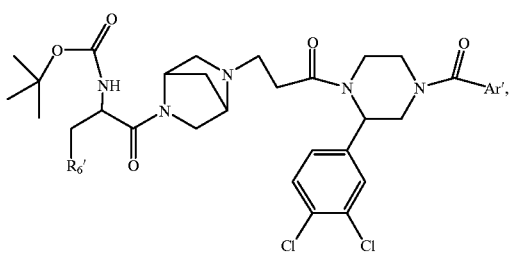
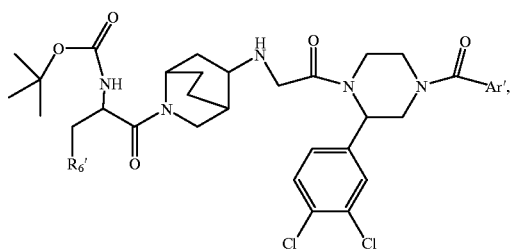
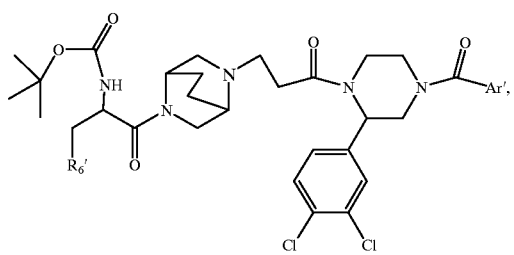
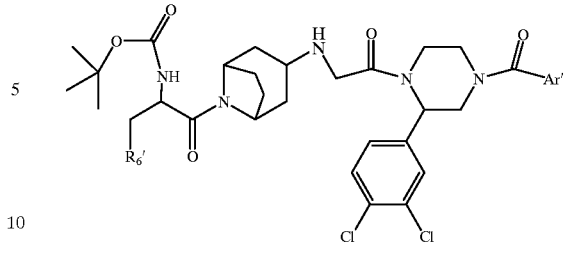
or
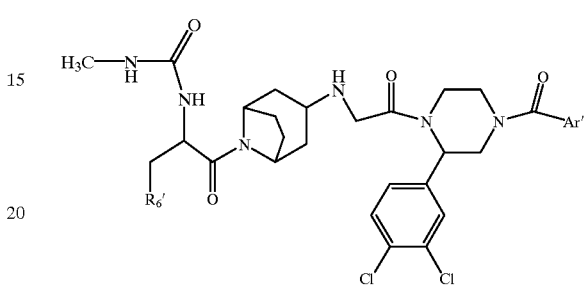
wherein R$_6$' is as defined above and wherein Ar' is
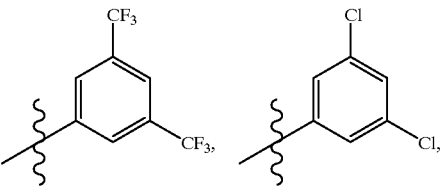 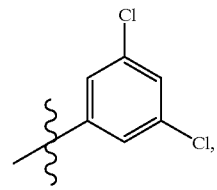
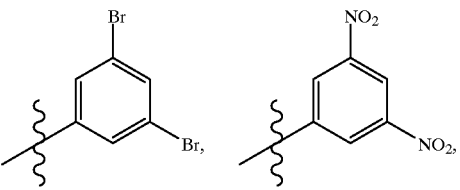 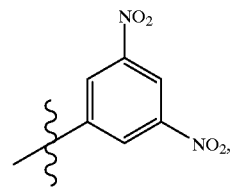
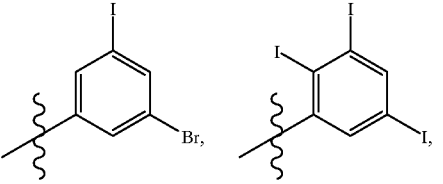 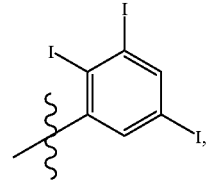
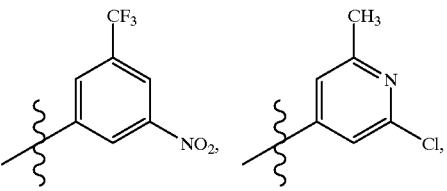 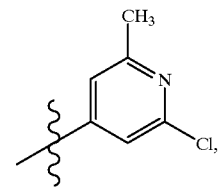
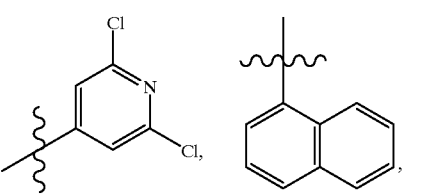 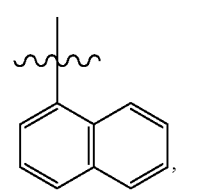

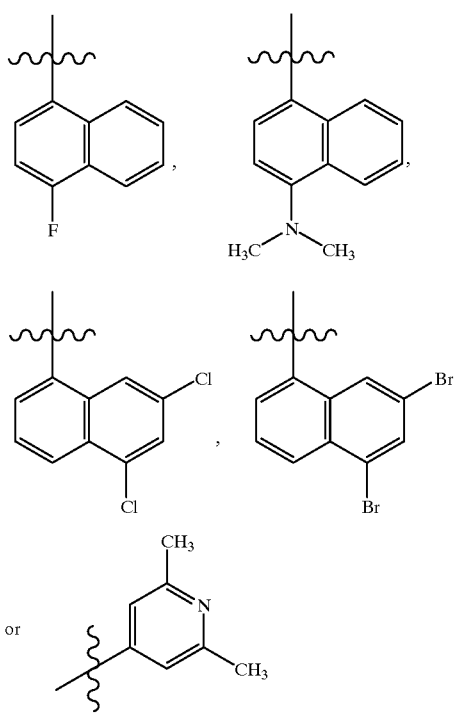

or any stereoisomer therof, including any enantiomer, diastereomer, endo, exo, R or S form thereof, or a pharmaceutically acceptable salt thereof.

The invention also relates to a pharmaceutical composition comprising a thereapeutically effective amount of a compound of formula I in combination with a pharmaceutically acceptable carrier.

The invention also relates to a method for inducing neurokinin antagonism which comprises administering a neurokinin antagonistic effective amount of a compound of formula I to a mammal in need thereof.

The invention also relates to a method for treating chronic airway diseases such as asthma and allergies; inflammatory diseases such as inflammatory bowel disease, psoriasis, fibrositos, osteoarthritis, and rheumatoid arthritis; migraine; central nervous system disorders such as emesis, depression, psychosis, dementia, and Alzheimer's disease; Down's syndrome; neuropathy; multiple sclerosis; ophthalmic disorders; conjunctivitis; auto immune disorders; graft rejection; systemic lupus erythematosus; GI disorders such as Crohn's disease and ulcerative colitis; disorders of bladder function; circulatory disorders such as angina; Raynaud's disease; coughing and pain. In particular, the invention also relates to a method of treating asthma which comprises administering to a mammal in need of such treatment an anti-asthma effective amount of a compound of formula I for such purpose.

DETAILED DESCRIPTION OF THE INVENTION

As used herein the term alkyl means a straight or branched, saturated hydrocarbon chain having from 1 to 6 carbon atoms. The number of carbon atoms may be designated. For example, "$C_1$–$C_6$ alkyl" represents a straight or branched, saturated hydrocarbon having from 1 to 6 carbon atoms.

The term $C_3$–$C_6$ cycloalkyl means a cycloalkyl having from 3 to 6 carbon atoms, that is cyclopropyl, cyclobutyl, cyclopentyl and cyclohexyl.

The term alkenyl means means a straight or branched, saturated alkenyl having from 2 to 6 carbon atoms. The number of carbon atoms may be designated. For example, "$C_2$–$C_6$ alkenyl" represents a straight or branched alkenyl having from 1 to 6 carbon atoms.

The term alkynyl means a straight or branched alkynyl having from 2 to 6 carbon atoms. The number of carbon atoms may be designated. For example, "$C_2$–$C_6$ alkynyl" represents a straight or branched chain alkynyl having from 2 to 6 carbon atoms.

As used herein, a heavy dark line (◀) denotes a chemical bond coming above the plane of the page. A dashed line (⸺) denotes a chemical bond coming below the plane of the page.

As used herein,

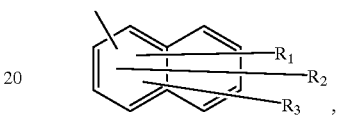

for example, means that $R_1$, $R_2$, and $R_3$ can be in either of the rings of the above naphthyl moiety.

Asymmetric centers exist in compounds of formula I of the invention. Accordingly, compounds of formula I include stereoisomers, i.e., enantiomers, diastereomers, endo and exo forms.

All such isomeric forms and mixtures thereof are within the scope of the present invention. Unless otherwise indicated, the methods of preparation disclosed herein may result in product distributions which include all possible structural isomers, although it is understood that physiological response may vary according to stereochemical structure. The isomers may be separated by conventional means such as fractional crystallization, preparative plate or column chromatography on silica, alumina, or reversed phase supports or HPLC (high performance liquid chromatography).

Enantiomers may be separated, where appropriate, by derivatization or salt formation with an optically pure reagent, followed by separation by one of the aforementioned methods. Alternatively, enantiomers may be separated by chromatography on a chiral support.

The compounds of formula I can exist in unsolvated as well as solvated forms, including hydrated forms, e.g. the hemihydrate. In general, the solvated forms, with pharmaceutically acceptable solvents such as water, ethanol, and the like are equivalent to the unsolvated forms for the purposes of the invention.

Those compounds of formula I which contain a basic group such as —$CH_2NH_2$, form pharmaceutically acceptable salts. The preferred pharmaceutically acceptable salts are nontoxic acid addition salts formed by adding to a suitable compound of the invention about a stoichiometric amount of a mineral acid, such as HCl, HBr, $H_2SO_4$ or $H_3PO_4$ or of an organic acid such as acetic, propionic, valeric, oleic, palmitic, stearic, lauric, benzoic, lactic, para-toluenesulfonic, methane-sulfonic, citric, maleic, fumaric, succinic, hydroxypropane sulfonic and the like, respectively.

GENERAL METHODS OF PREPARATION

The compounds of this invention may be prepared by one of the following general methods. As used herein RT means room temperature. Unless otherwise indicated, variables in the structural formulas below are as defined above. Starting materials and reagents used in the methods and examples below, are known or may be prepared according to known methods.

As used herein the term "substituted phenyl" means

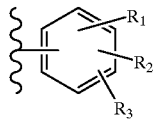

wherein $R_1$, $R_2$, and $R_3$ are as described herein.

"Substituted" means substituted by $R_1$, $R_2$, and/or $R_3$ as described herein.

"Aryl" means phenyl, naphthyl, indenyl, tetrahydronaphthyl, indanyl, anthracenyl or fluorenyl.

"Halogeno" refers to fluoro, chloro, bromo or iodo atoms.

"Heterocycloalkyl" refers to 4- to 6-membered rings comprising 1 to 3 heteroatoms independently selected from the group consisting of —O—, —S— and —N($R^6$)—, with the remaining ring members being carbon. Examples of heterocycloalkyl rings are tetrahydrofuranyl, pyrrolidinyl, piperidinyl, morpholinyl, thiomorpholinyl and piperazinyl.

"Heteroaryl" refers to 5- to 10-membered single or benzofused aromatic rings comprising 1 to 3 heteroatoms independently selected from the group consisting of —O—, —S— and —N=. Examples of single-ring heteroaryl groups are pyridyl, isoxazolyl, oxadiazolyl, furanyl, pyrrolyl, thienyl, imidazolyl, pyrazolyl, tetrazolyl, thiazolyl, thiadiazolyl, pyrazinyl, pyrimidinyl, pyridazinyl and triazolyl. Examples of benzofused heteroaryl groups are quinolinyl, thianaphthenyl (i.e., benzothienyl) and benzofurazanyl. N-oxides of nitrogen-containing heteroaryl groups are also included. All positional isomers are contemplated, e.g., 1-pyridyl, 2-pyridyl, 3-pyridyl and 4-pyridyl.

Where $R^2$ and $R^3$ substituents form a ring and additional heteroatoms are present, the rings do not include adjacent oxygen and/or sulfur atoms or three adjacent heteroatoms. Typical rings so formed are morpholinyl, piperazinyl and piperidinyl.

As used herein, the term "BOC" means t-butoxycarbonyl.

As used herein, the term "Ph" means phenyl.

As used herein, the term "parallel synthesis" means the preparation of individual chemical compounds as one of a batch of, for instance, 20, 30, or even 100 identical reactions on usually a single substrate but using a different reagent in each vessel. Such reagents are always of the same general class- in this case, either carboxylic acids or organic amines in any set of parallel reactions. The conditions used for each reaction are identical to those described in the examples, except that a simplified work-up is employed, generally a simple wash either with acid or base if appropriate, then water. The presence of the product is detected by thin layer chromatography (TLC) using known products as representative standards. Further characterization by combination HPLC/MS is generally performed. No further purification is performed on these materials before they are submitted to biological assays.

As used herein, each $R_c$ and $R_c'$ is independently selected from the group consisting of H, $C_1$–$C_6$ alkyl, $C_2$–$C_6$ alkenyl, $C_2$–$C_6$ alkynyl, unsubstituted or substituted phenyl, and unsubstituted or substituted benzyl.

The starting materials in the methods below are either known or can be prepared in accordance with known methods. In particular, the following compounds are either known or can be prepared in accordance with known methods: the diamine A, the compounds of formulas A, VI, VIII, X, XI, XIV, XVIII, XIX, XXa, A', XXV, and Z—H, as well as esters of formula XI, and compounds of formula

Method 1

If the group $Ar_2$ is an aromatic group with no I or Br substituents, then the following method may be used to prepare the useful intermediates (IV):

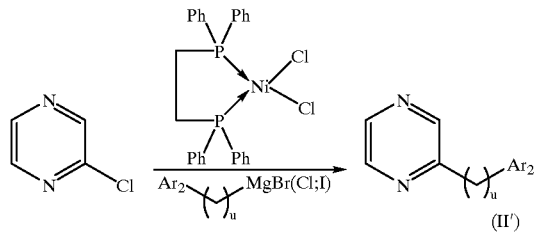

Transition metal catalyzed coupling of 2-chloropyrazine with an aromatic Grignard reagent in a dry, ether solvent, such as THF, yields the aryl-substituted pyrazine of formula II'. The catalyst shown, [1,2-bis-(diphenylphosphino)ethane]nickel$^{II}$ chloride, is a preferred reagent for this transformation. Where $Ar_2$ has no halo substituents, reduction of a compound of formula II' by catalytic hydrogenation, using, for instance, palladium acetate, preferably in acetic acid solvent, results in preferential reduction of the pyrazine ring, leaving the aromatic ring unreduced, that is, it results in a compound of formula II. Similarly, 10% Pd on charcoal (Pd—C) can be used in an alcohol solvent, preferably methanol, with or without the addition of a small quantity (1 to 5 equivalents) of acetic acid. Reaction times of about 1 to 24 hours generally suffice for this reaction, which is preferentially run at room temperature or slightly above (up to about 50° C.) and using from 1 to about 6 atmospheres pressure of hydrogen.

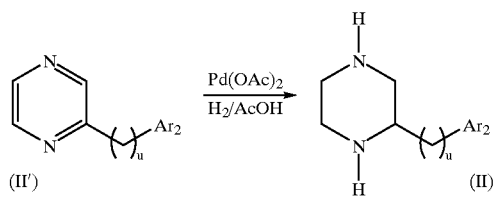

The intermediate of formula II may also be prepared from a compound of formula II', even if the group $Ar_2$ contains halogen atoms, by reduction using a strong hydride ion donor, preferably lithium aluminum hydride (LAH) or diisobutyl aluminum hydride (DIBAL-H) in an ether solvent, such as ether, THF or dimethoxyethane (DME).

Selective alkylation of a compound of formula II is possible using low temperature conditions. Thus, reacting a compound of formula II with a substituted aryl-alkyl halide of formula III where I is 0 to 2, results in the formation of the 4-substituted derivative of formula IV. Suitable conditions include use of a halogenated solvent, such as $CH_2Cl_2$, at low temperature. Suitable temperatures are from −78° C. initially, allowing the reaction mixture to warm gradually to RT if the reaction is not completed after several hours. The reaction is catalyzed by the addition of an equivalent amount of an organic base, such as triethylamine and diisopropylethylamine (Hünig's base).

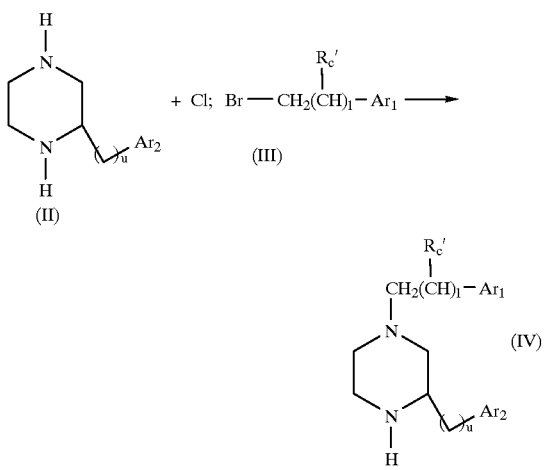

Method 2

If the group $Ar_2$ contains one or more halogen atoms on an aromatic ring and the other groups are as in Method 1, then an alternate route to a compound of formula IV is preferred. In addition, this method can be used to prepare compounds in which I is from 0 to 2. Mono-protection of the diamine of formula (A), preferably with BOC anhydride, or other agents known to introduce the t-butyloxycarbonyl protecting group, in an alcohol solvent, such as methanol, preferably at about −10° C., produces a compound of formula V.

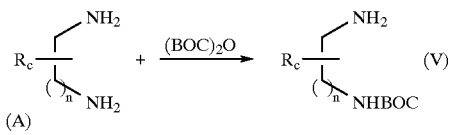

These compounds are used to perform a reductive amination reaction with the aldehyde of formula VI to produce an amine of formula VII. (In structures (A), (V), (VII), and (IX) herein, $R_c$ can be bound to any position between the two nitrogens. In cyclic structures like (IVA) below, $R_c$ can be bound to any available cyclic position that is occupied by carbon, and that is between the two nitrogens.)

Suitable conditions for this type of reaction include the use of an alcohol solvent, preferably methanol, or 2,2,2-trifluoroethanol, made slightly acidic with a weak organic acid, such as acetic acid, and a reducing agent known to favor reductive amination reactions, preferably sodium cyanoborohydride, $NaBH_3CN$.

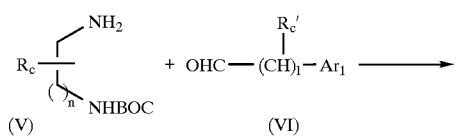

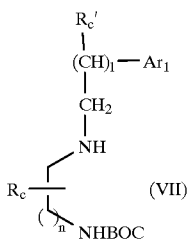

Reaction of a compound of formula VII with an α-haloketone of formula VIII, in which $Ar_2$ preferably represents a halogenated aromatic ring, but may be any of the claimed aromatic rings, in the presence of an organic base, such as di-isopropylethylamine, also known as Hünig's Base, in an ether solvent, such as THF, results in the formation of the intermediates of formula IX.

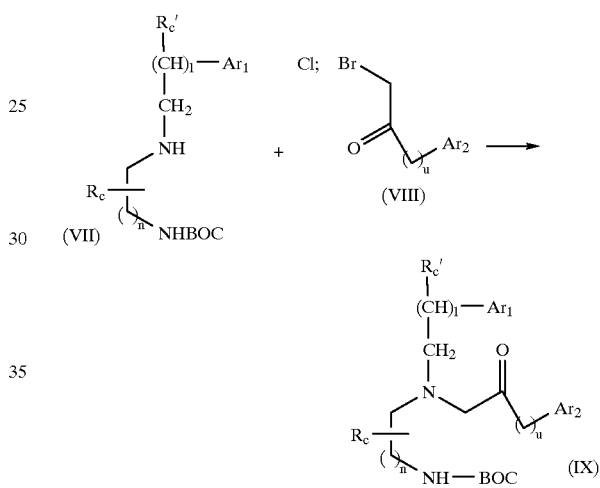

Removal of the BOC protecting group using a suitable acidic catalyst, such as trifluoroacetic acid, followed by an intramolecular reductive amination, under conditions such as those described above for the preparation of a compound of formula VII, leads to the formation of compounds of formula IVA.

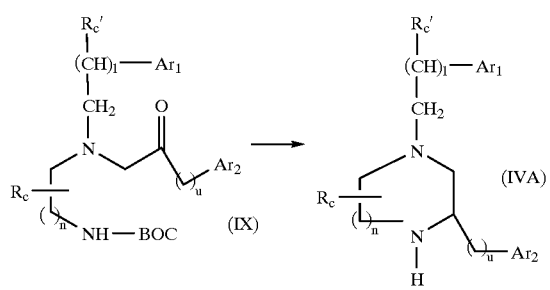

Method 3

An alternate route to compounds of the invention in which I is 0 to 2 is as follows. Standard coupling of an N-protected amino acid of formula X, wherein $Ar_2$ is as described above, with an amino acid ester derivative

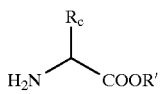

R' is $C_2$–$C_4$ alkyl, preferably, the ethyl ester of formula XI, .Et in the formulas herein means ethyl), produces a dipeptide of formula XII. A suitable protecting group is BOC, although many others may also be used. Other esters of the amino acid may also be used. Standard coupling techniques may be applied, an example being the use of N-hydroxybenztriazole (HOBT) and a water-soluble carbodiimide, such as 1-(3-dimethylaminopropyl)-3-ethylcarbodiimide (DEC), in a non-hydroxylic solvent such as $CH_2Cl_2$, DMF or a mixture of the two foregoing solvents. The reaction is run, preferably, at or below RT, and takes from 1 to 40 hours for completion, depending upon the substrates.

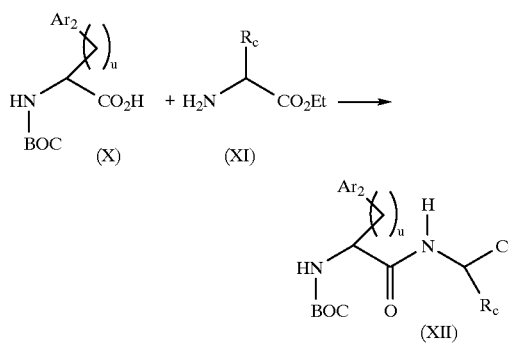

Removal of the protecting group under standard conditions, followed by treatment of the product with a base results in cyclization to the diketopiperazine of formula XIII. Suitable conditions for removal of the exemplified BOC group are well known in the art and include catalysis by trifluoroacetic acid (TFA). A suitable base for cyclization is the alkali metal salt of an alcohol in the alcohol itself used as solvent. For example, a solution of sodium ethoxide in ethanol may be used. The temperature is preferably around RT but may be slightly above or below, in the range 0° C. to about 40° C. The reaction is generally complete within a few hours. Suitable reaction times are from 1 to 24 hours.

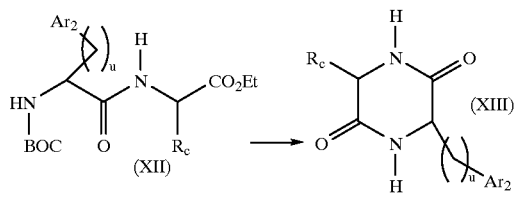

Reduction of the diketopiperazine of formula XIII to a compound of formula II may be accomplished preferentially with a strong hydride reducing agent, such as LAH or a solution of sodium bis(2-methoxy-ethoxy)aluminum hydride in toluene (also known as Red-Al®), or the $BH_3$.S$(CH_3)_2$ complex. Suitable solvents for this reaction are DME and other higher boiling ethers since the reaction is run at elevated temperatures, from about 50° C. to about 110° C., preferably about 90° C.

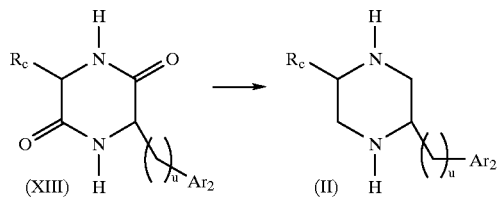

Alternatively, a compound of formula of II may be prepared by the scheme shown below (J. Med. Chem., 9, 181 (1966)). As used herein L is any readily available ester residue such as $C_1$–$C_7$ alkyl, more preferably methyl or ethyl.

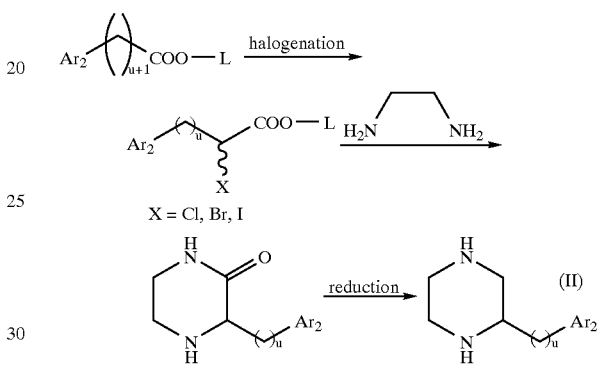

A compound of formula II may be converted to a compound of formula IV by the processes described in Method 1 above or Method 6 below.

Method 4

The intermediates of formula IV or IVA, formed via any of the previous methods, may be further processed as follows. A compound of formula IVA will be used in the Schemes. Reaction of a compound of formula IVA with an activated halo-acid, generally the acid halide of formula XIV, in which Hal represents Cl, Br, or I, yields the acylated derivative of formula XV that is, m is 1 for formula I. An organic base is used to take up the hydrogen halide formed in the reaction, suitable bases being triethylamine (TEA) and Hünig's Base. Suitable reaction media include halogenated solvents, such as methylene chloride and chloroform. The reaction is preferably run at low temperature, at least initially. Suitable temperatures are in the region of −50° C. down to −80° C. Later in the reaction it may be desirable to allow the mixture to warm up to about RT to ensure completion of the reaction.

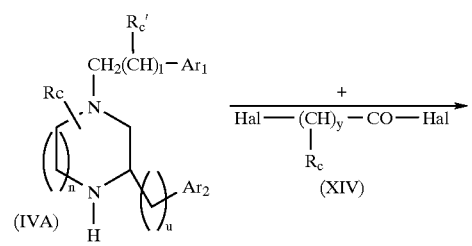

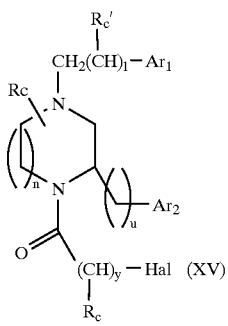

Reaction of the halogenated amides of formula XV with an amine of formula Z—H results in formation of the products of formula XVI, which are compounds of the invention in which X is O and m is 1. Compounds of formula XVI have been modified to show the fact that these products could have been prepared from compounds of formula IVA as well as from IV. Suitable solvents for this reaction are halogenated hydrocarbons, such as methylene chloride, and an organic base is present to absorb the H-Hal formed. Appropriate bases include Hünig's Base. The reaction is performed at or around RT, a suitable temperature being generally in the range of from 0° C. to 40° C. Reaction is complete within 1 to 48 hours.

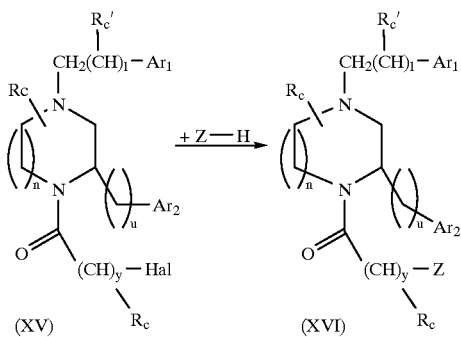

Method 5

Compounds of formula XVI where y≠0 may be converted to other compounds of the invention of formula XVII by reduction under controlled conditions.

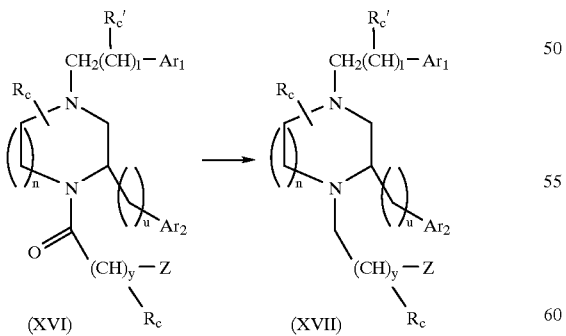

Suitable reducing agents to effect this transformation include the borane-dimethyl sulfide complex, as well as other less selective reagents, such as LAH, (assuming that no other group reactive to LAH is present), Red-Al®, and diborane in ether. Effective temperatures for the borane-dimethylsulfide complex to reduce compounds of formula XVI, range from RT to the reflux temperature of the solution of the reagent in THF (about 80° C.).

Method 6

Intermediates of the formula XVIII may be selectively acylated by coupling with an acid of the formula XIX. Standard coupling techniques may be applied, for example the use of HOBT, a water-soluble carbodiimide, such as DEC, and an organic base, such as Et₃N, in a non-hydroxylic solvent, such as CH₂Cl₂, at a temperature of about −20° C. initially. The mixture may be allowed to warm to RT to complete the reaction. The product of reaction is the amide of formula XX.

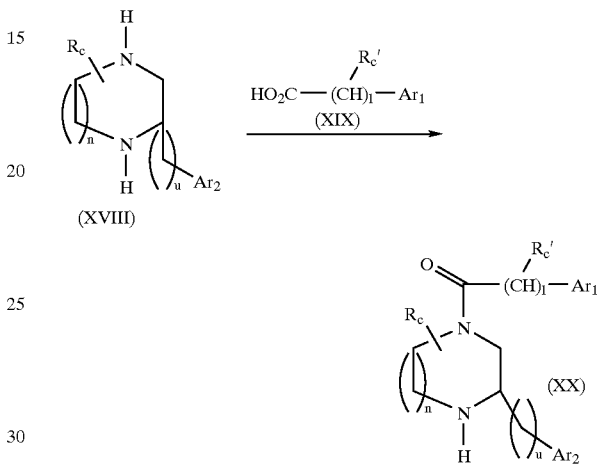

Compounds of the formula XX, may be further acylated using an acid halide of formula XIV. The reaction is run, preferably at about −78° C., over a period of 1 to 12 hours, in a halogenated solvent, such as methylene chloride or similar solvent. An organic tertiary amine is used to absorb the H-Hal produced in the reaction. Suitable amines include triethylamine and Hünig's Base. As used herein Hal means Cl, Br, or I.

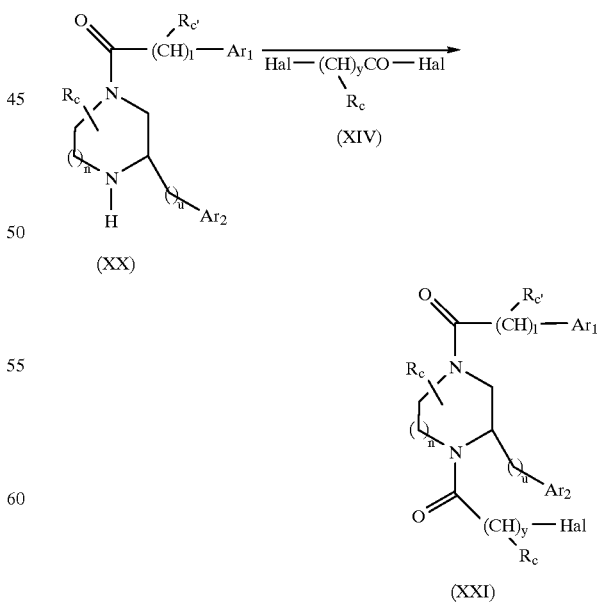

The compounds of formula XXI, that is, m is 1 in formula I, y=1–3, l=0–2 may be used for further reaction without isolation. Additional organic base, for instance, Hünig's Base, is added to the mixture followed by Z—H, at or around −78° C. The reaction is completed by allowing the mixture to warm to RT overnight yielding the compounds of formula XXII after work-up and purification by standard methods.

If the group $X_4$ in Z is —O—, then the reaction of Z—H with XXI is preferably carried out after isolation of XXI by adding NaH, or a similar base, to a solution of Z—H (wherein $X_4$ is —O—) in an ether solvent (e.g., THF) at or near RT, under $N_2$. After about 24 hours of stirring, XXI in a solvent such as THF is added and the mixture is allowed to stir at RT for 2 to 24 hours, followed by work-up and purification by flash chromatography to obtain the product of formula XXII wherein $X_4$ is —O—.

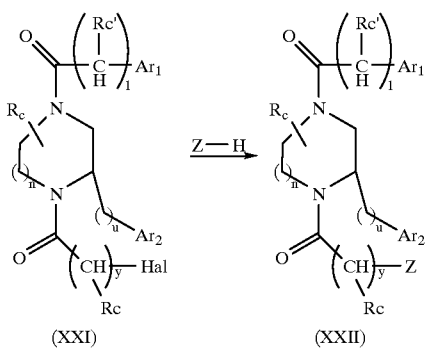

The compounds of formula XXII, in which y=1–3 may be converted to other products of formula XXIII by reduction under controlled conditions.

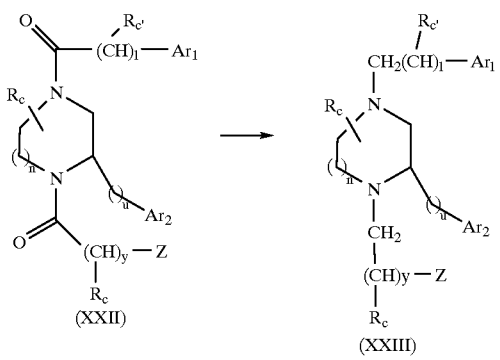

Suitable reducing agents to effect this transformation include the borane-methyl sulfide complex, as well as other less selective reagents, such as LAH, Red-Al®, and diborane in ether or other unreactive solvents, such as THF. Using the borane-methyl sulfide complex in THF, at the reflux temperature of the solution, which is about 80° C., the reaction is complete in about 2 hours to 48 hours depending on the precise substrate.

Some of the substrates Z—H for the alkylation reaction were synthesized from diamino compound (A) by initial conversion to the t-BOC protected derivative(B) followed by removal of the benzyl group by hydrogenolysis over a suitable catalyst such as $Pd(OH)_2$ to yield the t-BOC protected derivative (C). Subsequent elaboration of (C) can be accomplished by either alkylation or reductive alkylation depending on the availability of reagents for these reactions.

Reaction of the intermediate (C) with an aldehyde or ketone (D) under the conditions of reductive amination, such as in methanol and in the presence of $NaBH_3CN$ with sufficient AcOH (acetic acid) present to allow the reaction to proceed at a suitable rate, produces the amine (E) from which the t-BOC group may be removed with 4N—HCl in dioxane followed by basification, for instance, with an aqueous solution of NaOH, to produce the compound of formula (F).

The same product, (Ea), may be prepared from (C) by alkylation with the halide derivative (G) in which "Hal" is Cl, Br, or I. Other activated leaving groups are also possible for this reagent, such as mesylates or tosylates. The reagent is preferably primary but the reaction can also often be made to work acceptably for secondary derivatives.

The product of the alkylation, (Ea), may be treated as described above to produce the reagent (Fa) which represents one of the preferred forms of Z which can be used to convert a compound of formula XXI to a compound of formula XXII.

The intermediate (C) (below) may also be modified by acylation, for instance with an acid halide of formula (H), to produce the intermediate (I), in which $n_3 \ne 0$. Removal of the BOC protecting group, as described previously, leads to the amine (J) which represents one of the preferred forms of Z. This may be used to convert a compound of formula (XXI) to a compound of the invention, as described above.

In addition, other Z structural variations as defined earlier may be carried out through this same sequence of reactions. In the reaction scheme below, in the generic definition of Z, G is represented by the benzyl group in (A), which is subsequently elaborated by the described reaction sequences, and $X_4$ is —$NHR_5$. Thus, the structure (A) may be seen to be a representative of several of the disclosed Z moieties.

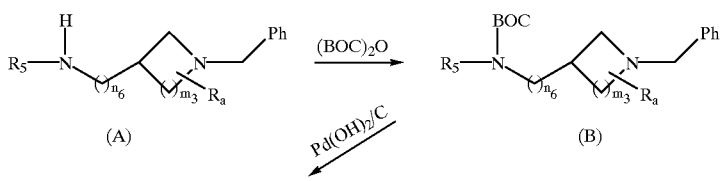

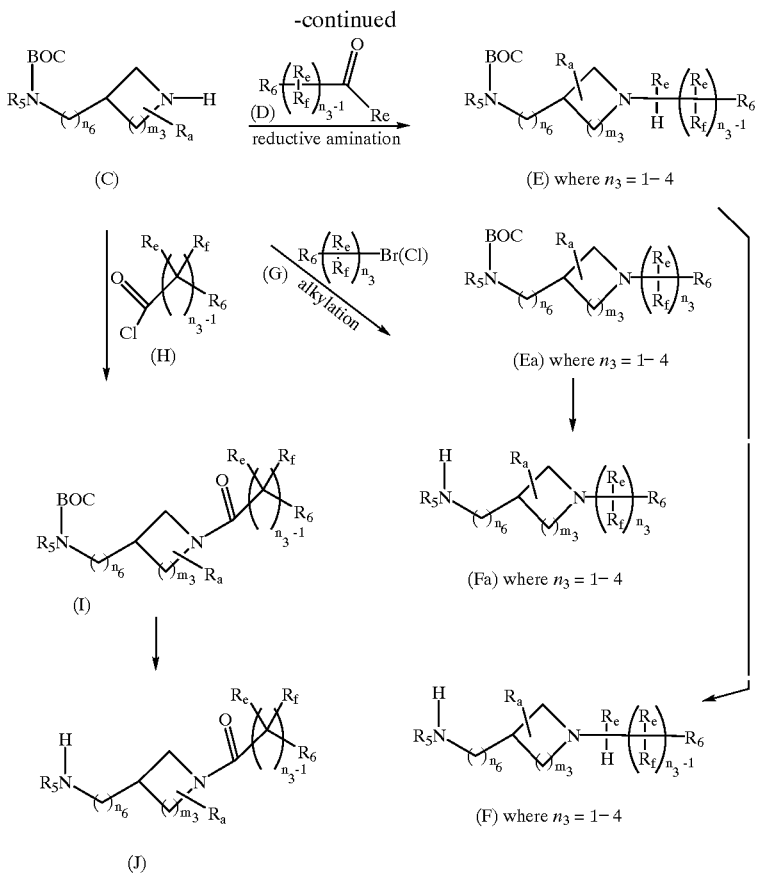

Method 6a

A useful intermediate for certain variations in the group Z is the compound (K). This may be prepared from (XXI) and the protected amine (L). The starting material for this process is the N—BOC protected amine (M) which may be converted to (L) by standard techniques involving formation of the oxime using hydroxylamine hydrochloride in pyridine followed by reduction with hydrogen over Raney nickel in ethanol solution. Removal of the protecting group from (K), under conditions described previously, results in the amine (N).

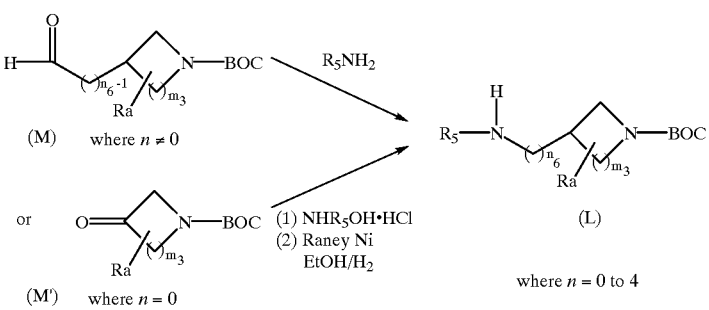

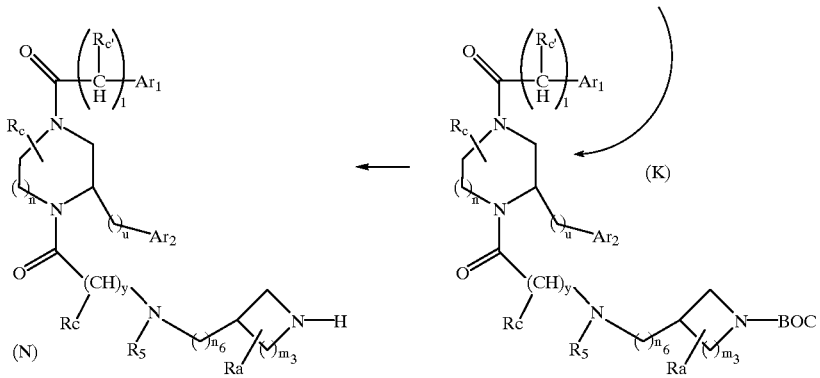

Use of this intermediate under conditions of acylation, under controlled conditions, results in reaction at the ring nitrogen atom to yield products such as (O). Either the acid halide, e.g. chloride (P), may be used, or a coupling reaction with a carboxylic acid may be used under conditions essentially similar to those described earlier using a water-soluble carbodimide reagent, for instance.

Sometimes the starting material (N) is provided as a salt, such as the HCl salt. In this case, it is necessary to add an organic tertiary base, such as Hünig's base to produce the free amine.

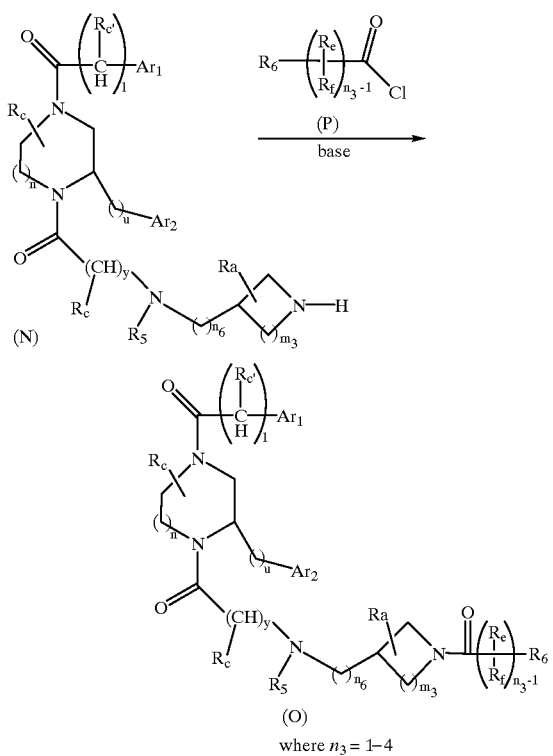

Alkylation of (N) may be accomplished with a suitable halogen-containing reagent, for instance, to produce (Q). Reagents such as (G) may be used for this conversion.

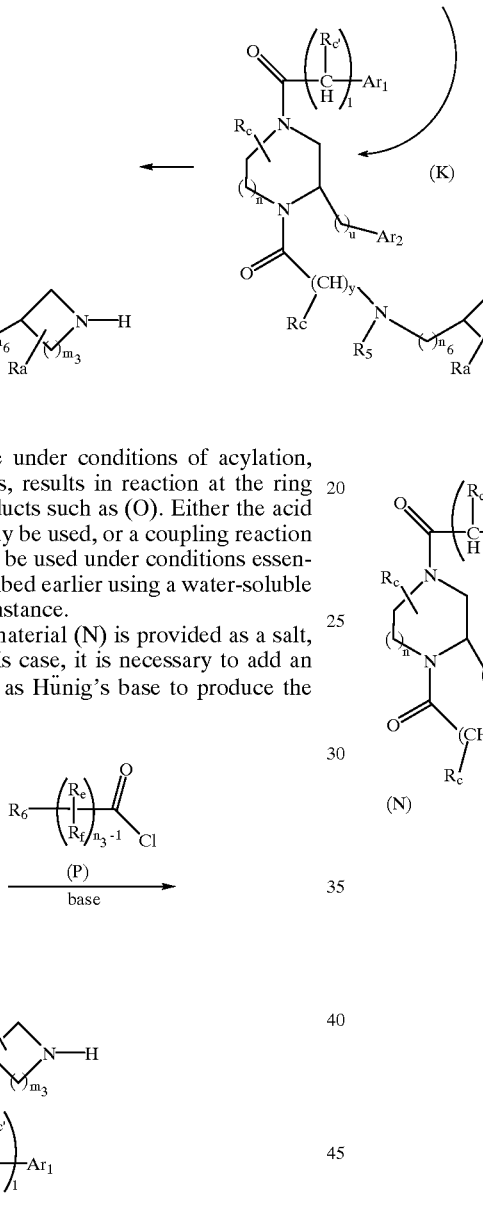

In some cases, one of the —$C(R_e)(R_f)$— groups may be a carbonyl group with the exception that the carbon in the carbonyl can not be directly attached to the nitrogen atom since these products are amides which are described above.

Under certain circumstances, specifically where at least one of the groups $R_e$ and $R_f$ on the carbon atom to be directly attached to the ring nitrogen is H, then a reductive alkylation reaction may be performed, as described previously, to produce the compound of the invention (R). The reagent used for this conversion is (D), an aldehyde (if Re=H) or ketone.

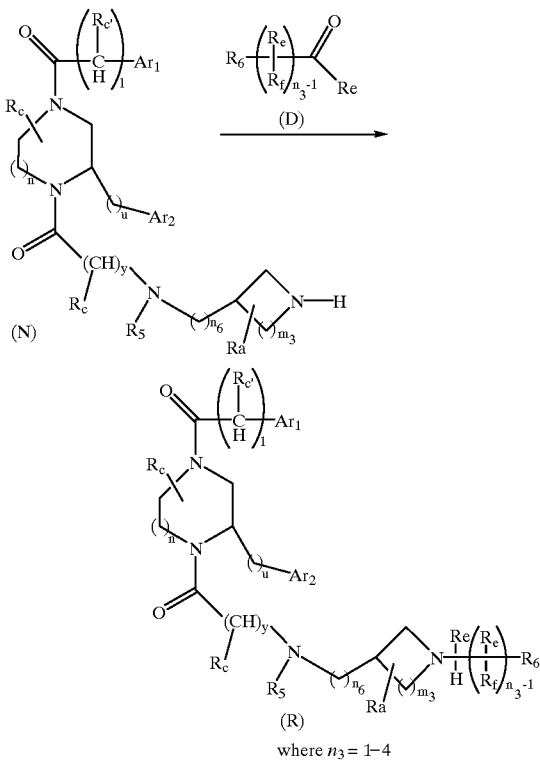

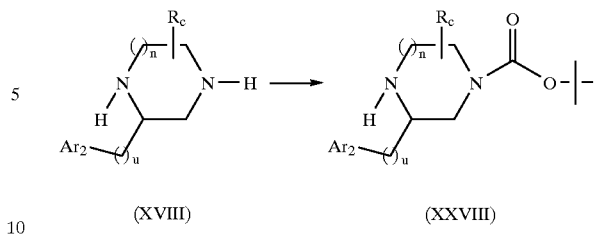

As before, reaction occurs preferentially at the nitrogen atom further away from the Ar$_2$ group. Reaction of this intermediate with a reagent of structure (XIV) as described above, leads to the halo-derivative (XXIX). Reaction of (XXIX) with Z—H, again as described above, produces the intermediate (XXX) which may be de-protected to produce (XXXI). Suitable reagents include trifluoroacetic acid and HCl.

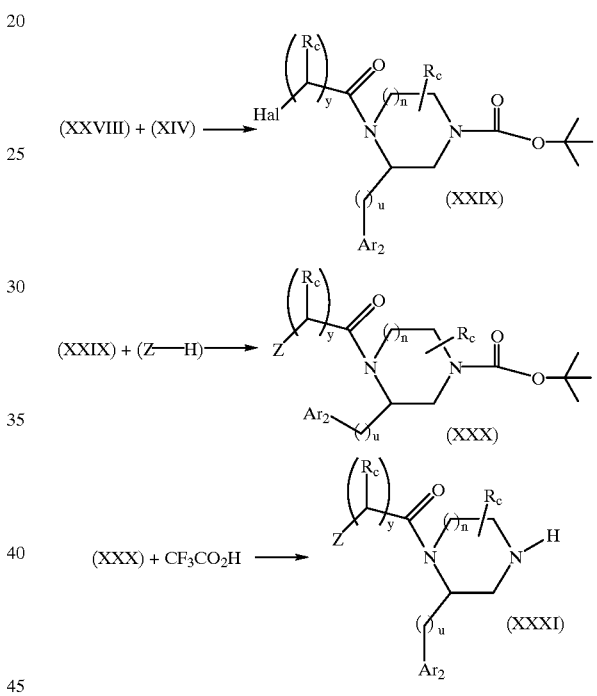

Reaction of (XXXI) with a carboxylic acid (XIX) under such coupling conditions as described above, leads to the products of formula (XXII).

Method 7a

Synthesis of the compounds of the invention wherein the pendant aromatic group Ar$_2$, or the pendant aromatic group Ar$_2$ and its sidechain, are located in the alternate ring position to the compounds of formula XXII (i.e. compounds of formula C below), may be prepared using compounds of formula XXVIII from method 7 as starting materials. Coupling of compounds of formula XXVIII with any of the acids

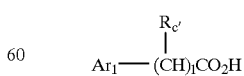

under standard coupling conditions, for instance using HOBT, Et$_3$N and DEC in CH$_2$Cl$_2$, produces the intermediate (A).

Removal of the t-BOC or other protecting group under standard conditions releases the free amine (B). Acylation of In addition, other Z structural variations may be carried through this same reaction sequence. In the reaction scheme above, in the generic definition of Z, G is represented by the BOC group in (M) or (M'), which is subsequently elaborated by the described reaction sequences, and X$_4$ is —NHR$_5$. Thus, the structure (A) may be seen to be a representative of several of the disclosed Z moieties.

Method 7

The acylated derivatives of formula XX from Method 6 may be reduced to the saturated alkyl chain derivatives of formula IVA.

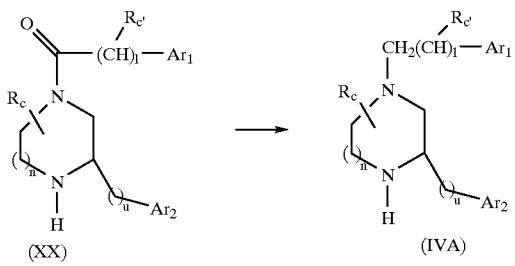

The process to conduct this conversion is the same as described in Method 6 for conversion of a compound of formula XXII to a compound of formula XXIII. The reagent of preference is the borane-methyl sulfide complex.

A compound of formula IVA can be converted to a target compound of formula XVI as described previously.

An alternate route to compounds of structure (XXII) also starts with compound (XVIII). Initial reaction with an amine protecting group reagent, preferably BOC anhydride, preferably at temperatures of about −20° C. to 0° C., produces the N-t-butyloxycarbonyl derivative of the formula XXVIII.

(B) and further reaction with Z—H proceeds as described in Method 6 for the conversion of (XX) via (XXI) to (XXII) to produce compound (C) of the invention.

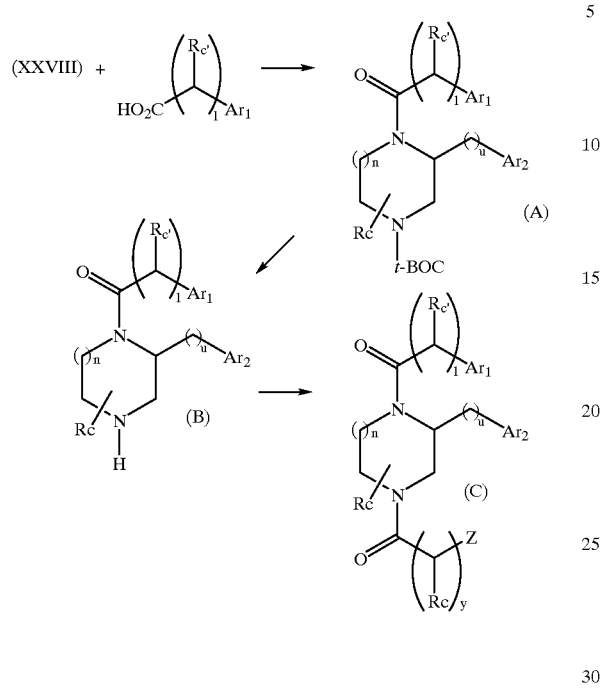

Method 8

A method for introducing a group, $R_c$, into the sidechain of a compound of the invention begins with a previously prepared compound of formula (XX). This may be coupled with a suitably protected amino-acid derivative of formula (XXXII) in which the t-BOC group is used as a representative protecting group. Use of a relatively reactive coupling agent, such as BOP-Cl of formula (XXXIII), is preferred and the reaction is run under standard coupling conditions well known to one skilled in the art. Suitable conditions include the use of $CH_2Cl_2$ and/or DMF as solvent, with triethylamine or Hünig's Base, and a temperature between 0° C. initially and RT. Usual work-up conditions yield the protected intermediate of formula (XXXIV).

In the case of (XXXIV), in which the N-protecting group is t-BOC, the usual conditions for removal of such a group may be used to free the amine function. Various concentrations of $CF_3CO_2H$ in $CH_2Cl_2$ will usually suffice. In some substrates a fairly dilute solution (e.g. 2N) will be sufficient whereas in other cases a more concentrated solution, up to neat TFA, may be necessary. In addition, other N-protecting groups may be employed and removed by methods well known in the art. An example is use of the N—Cbz which may be removed under either acidic or hydrogenolytic conditions. The result of deprotection is the amine intermediate of the formula (XXXV).

Conversion of intermediate of the formula (XXXV) to compounds of the invention is then carried out by a reductive alkylation process.

The group Z, wherein $X_4$ is —$NHR_5$ in the final product, is introduced into the molecule using an aldehyde or ketone in which the aforementioned group is present at the carbon atom that is to be joined to the amino group of the formula (XXXV). An example of such an intermediate is a compound of the formula (XXXVI).

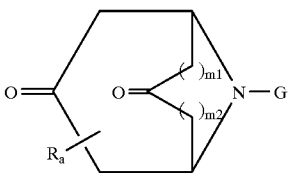

XXXVI although those skilled in the art will recognize that other Z groups can be used in place of XXXVI.

After the reaction this group becomes the Z group of the compounds of the invention, that is, the "Y—NH" group shown in compounds of the formula (XXXVII) just below

XXXVII

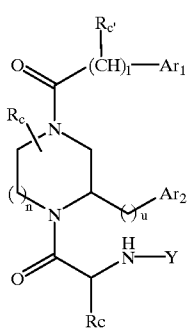

is equivalent to the "Z" group shown in the Summary of the Invention. Conditions for this reductive amination procedure are known in the art and are exemplified by the use of NaBH$_3$CN in MeOH with the addition of several equivalents of acetic acid. Generally, the reaction is performed at RT and is left to react overnight.

Product is isolated by standard means, such as decomposition of excess reagent with H$_2$O and extraction of the product into an organic solvent such as CH$_2$Cl$_2$ or a mixture of Et$_2$O and CH$_2$Cl$_2$.

Using procedures similar to those described in the above or using procedures known to those skilled in the art, one can produce all of the compounds of formula I of the invention. For example, one can obtain compounds of the invention of formula I wherein the R$_c$ moiety is on various carbons of the piperazine ring.

The in vitro and in vivo activity of the compounds of formula I can be determined by the following procedures.

In vitro procedure to identify NK$_1$ activity

Test compounds are evaluated for their ability to inhibit the activity of the NK$_1$ agonist Substance P on the isolated guinea pig vas deferens. Freshly cut vas deferens are removed from male Hartley guinea pigs (230–350 g) and suspended in 25 ml tissue baths containing Kreb's Henseleit solution warmed to 37° C. and constantly aerated with 95% O$_2$ and 5% CO$_2$. Tissues are adjusted to 0.5 g and allowed to equilibrate for a period of 30 minutes. The vas deferens are exposed to an electrical field stimulation (Grass S48 Stimulator) every 60 seconds at an intensity that will cause the tissue to contract 80% of its maximum capacity. All responses are recorded isometrically by means of a Grass force displacement transducer (FT03) and Harvard electronic recorder. Substance P potentiates the electrical field stimulated-induced contractions of the guinea pig vas deferens. In unpaired studies, all tissues (control or drug treated) are exposed to cumulative concentrations of Substance P ($1 \times 10^{-10}$M–$7 \times 10^{-7}$M). Single log-concentrations of the test compounds are given to separate tissues and allowed to equilibrate for 30 minutes before a Substance P concentration-response curve is generated. At least 5 separate tissues are used for each control and individual drug-concentration for every drug assay.

Inhibition of the Substance P is demonstrated by a rightward shift of its concentration-response curve. These shifts are used to determine the pA$_2$ value, which is defined as the negative log of the molar concentration of the inhibitor which would require that twice as much agonist be used to elicit a chosen response. This value is used to determine relative antagonist potency.

Isolated Hamster Trachea NK$_2$ Assay

General methodology and characterization of hamster trachea responses to neurokinin agonists as providing an NK$_2$ monoreceptor assay is found in C. A. Maggi, et al., *Eur. J. Pharmacol.* 166 (1989) 435 and J. L. Ellis, et al., *J. Pharm. Exp. Ther.* 267 (1993) 95.

Continuous isometric tension monitoring is achieved with Grass FT-03 force displacement transducers connected to Buxco Electronics preamplifiers built into a Graphtec Linearcorder Model WR 3310. Male Charles River LAK:LVG (SYR) hamsters, 100–200 g fed weight, are stunned by a sharp blow to the head, loss of corneal reflex is assured, the hamsters are sacrificed by thoractomy and cutting the heart. Cervical trachea segments are removed to room temperature Krebs buffer, pH 7.4, aerated with 95% O$_2$–5% CO$_2$ gas and cleaned of adhering tissue. The segments are cut into two 3–4 mm long ring segments. Tracheal rings are suspended from transducers and anchored in 15.0 ml water jacketed organ baths by means of stainless steel hooks and 6-0 silk. Baths are filled with Krebs buffer, pH 7.4, maintained at 37° C. and continuously aerated with 95% O$_2$–5% CO$_2$ gas. Tracheal rings are placed under 1.0 g initial tension and allowed a 90 min equilibration period with four 1 $\mu$M NKA challenge, wash and recovery cycles at 20 min intervals. 30 min vehicle pretreatment is followed by cumulative additions of rising doses of NKA (3 nM–1 $\mu$M final concentration, 5 min intervals between additions). The final NKA response is followed by a 15 min wash and recovery period. 30 min pretreatment with a test compound or its vehicle is followed by cumulative additions of rising doses of NKA (3 nM–10 $\mu$M final concentration if necessary, 5 minutes intervals between additions). The final NKA response is followed by a 1 mM carbachol challenge to obtain a maximal tension response in each tissue.

Tissue responses to NKA are recorded as positive pen displacements over baseline and converted to grams tension by comparison to standard weights. Responses are normalized as a % of the maximal tissue tension. ED$_{50}$'s are calculated for NKA from the control and treated NKA dose responses and compared. Test compounds resulting in an agonist dose ratio$\geq$2 at a screening concentration of 1 $\mu$M (i.e. pA$_2 \geq$=6.0) are considered actives. Further dose response data is obtained for actives so that an apparent pA$_2$ estimate can be calculated. pA$_2$ is calculated either by estimation of K$_i$ as described by Furchgott (where pA$_2$=−Log K$_i$, R. F. Furchgott, *Pharm. Rev.* 7 [1995] 183) or by Shild Plot Analysis (O. Arunlakshana & H. O. Shild, *Br. J. Pharmacol.* 14[1959] 48) if the data is sufficient.

Effect of NK$_1$ Antagonists on Substance P-Induced Airway Microvascular Leakage in Guinea Pigs Studies are performed on male Hartley guinea pigs ranging in weight from 400–650 g. The animals are given food and water ad libitum. The animals are anesthetized by intraperitoneal injection of dialurethane (containing 0.1 g/ml diallylbarbituric acid, 0.4 g/ml ethylurea and 0.4 g/ml urethane). The trachea is cannulated just below the larynx and the animals are ventilated (V$_T$=4 ml, f=45 breaths/min) with a Harvard rodent respirator. The jugular vein is cannulated for the injection of drugs.

The Evans blue dye technique (Danko, G. et al., *Pharmacol. Commun.*, 1, 203–209, 1992) is used to measure airway microvascular leakage (AML). Evans blue (30 mg/kg) is injected intravenously, followed 1 min later by i.v. injection of substance P (10 $\mu$g/kg). Five min later, the thorax is opended and a blunt-ended 13-guage needle passed into the aorta. An incision is made in the right atrium and blood is expelled by flushing 100 ml of saline through the aortic catheter. The lungs and trachea are removed en-bloc and the trachea and bronchi are then blotted dry with filter paper and weighed. Evans blue is extracted by incubation of the tissue at 37° C. for 18 hr in 2 ml of formamide in stoppered tubes. The absorbance of the formamide extracts of dye is measured at 620 nm. The amount of dye is calculated by interpolation from a standard curve of Evans blue in the range 0.5–10 μg/ml in formamide. The dye concentration is expressed as ng dye per mg tissue wet weight. Test compounds were suspended in cyclodextran vehicle and given i.v. 5 min before substance P.

Measurement of $NK_2$ Activity In Vivo

Male Hartley guinea pigs (400–500 gm) with ad lib. access to food and water are anesthetized with an intraperitoneal injection of 0.9 ml/kg dialurethane (containing 0.1 g/m diallylbarbituric acid, 0.4 g/ml ethylurea and 0.4 g/ml urethane). After induction of a surgical plane of anesthesia, tracheal, esophageal and jugular venous cannulae are implanted to facilitate mechanical respiration, measurement of esophageal pressure and administration of drugs, respectively.

The guinea pigs are placed inside a whole body plethysmograph and the catheters connected to outlet ports in the plethysmograph wall. Airflow is measured using a differential pressure transducer (Validyne, Northridge Calif., model MP45-1, range±2 $cmH_2O$) which measures the pressure across a wire mesh screen that covers a 1 inch hole in the wall of the plethysmograph. The airflow signal is electrically integrated to a signal proportional to volume. Transpulmonary pressure is measured as the pressure difference between the trachea and the esophagus using a differential pressure transducer (Validyne, Northridge, Calif., model MP45-1, range±20 cm $H_2O$). The volume, airflow and transpulmonary pressure signals are monitored by means of a pulmonary analysis computer (Buxco Electronics, Sharon, Conn., model 6) and used for the derivation of pulmonary resistance ($R_L$) and dynamic lung compliance ($C_{Dyn}$).

Bronchoconstriction Due to NKA

Increasing iv doses of NKA are administered at half log (0.01–3 μg/kg) intervals allowing recovery to baseline pulmonary mechanics between each dose. Peak bronchoconstriction occurs within 30 seconds after each dose of agonist. The dose response is stopped when $C_{Dyn}$ is reduced 80–90% from baseline. One dose-response to NKA is performed in each animal. Test compounds are suspended in cyclodextran vehicle and given i.v. 5 min before the initiation of the NKA dose response.

For each animal, dose response curves to NKA are constructed by plotting the percent increase in $R_L$ or decrease in $C_{Dyn}$ against log dose of agonist. The doses of NKA that increased $R_L$ by 100% ($R_L100$) or decreased $C_{Dyn}$ by 40% ($C_{Dyn}40$) from baseline values are obtained by log-linear interpolation of the dose response curves.

Neurokinin Receptor Binding Assay(s)

Chinese Hamster ovary (CHO) cells transfected with the coding regions for the human neurokinin 1 ($NK_1$) of the human neurokinin 2 ($NK_2$) receptors are grown in Dulbecco's minimal essential medium supplemented with 10% fetal calf serum, 0.1 mM non-essential amino acids, 2 mM glutamine, 100 units/ml of penicillin and streptomycin, and 0.8 mg of G418/ml at 37° C. in a humidified atmosphere containing 5% $CO_2$.

Cells are detached from T-175 flasks with a sterile solution containing 5 mM EDTA in phosphate buffered saline. Cells are harvested by centrifugation and washed in RPMI media at 40° C. for 5 minutes. The pellet is resuspended in Tris-HCl(pH7.4) containing 1 uM phosphoramidon and 4 ug/ml of chymostatin at a cell density of $30 \times 10^6$ cells/ml. The suspension is then homogenized in a Brinkman Polytron (setting 5) for 30–45 seconds. The homogenate is centrifuged at 800×g for 5 min at 4° C. to collect unbroken cells and nuclei. The supernatant is centrifuged in a Sorvall RC5C at 19,000 rpm (44,00×g) for 30 min at 4° C. The pellet is resuspended, an aliquot is removed for a protein determination (BCA) and washed again. The resulting pellet is stored at −80° C.

To assay receptor binding, 50 μu of [$^3$H]-Substance P (9-Sar, 11-Met [02]) (specific activity 41 Ci/mmol) (Dupont-NEN) (0.8 nM for the NK-1 assay) or [$^3$H]-Neurokinin A (specific activity 114 Ci/mmole) (Zenca) (1.0 nM for the NK-2 assay) is added to tubes containing buffer (50 mM Tris-HCl(pH 7.4) with 1 mM $MnCl_2$ and 0.2% Bovine Serum Albumin) and either DMSO or test compound. Binding is initiated by the addition of 100 μl of membrane (10–20 μg) containing the human NK-1 or NK-2 receptor in a final volume of 200 μl. After 40 minutes at room temperature, the reaction is stopped by rapid filtration onto Whatman GF/C filters which have been presoaked in 0.3% polyethylenimine. Filters are washed 2 times with 3 ml of 50 mM Tris-HCl (pH7.4). Filters are added to 6 mls of Ready-Safe liquid scintillation cocktail and quantified by liquid scintillation spectrometry in a LKB 1219 RackBeta counter. Nonspecific binding is determined by the addition of either 1 μM of CP-99994 ($NK_1$) or 1 μM SR-48968 ($NK_2$) (both synthesized by the chemistry department of Schering-Plough Research Institute). $IC_{50}$ values are determined from competition binding curves and Ki values are determined according to Cheng and Prusoff using the experimentally determined value of 0.8 nM for the $NK_1$ receptor and 2.4 nM for the $NK_2$ receptor.

For all of the compounds of the invention, the $NK_1$ binding is in a range of about 0–100% inhibition at 1 μM concentration. For all of the compounds of the invention, the $NK_2$ binding is in a range of about 0–100% inhibition at 1 μM concentration. It should be understood that while the NK binding for certain compounds of the invention is as low as 0% at 1 μM concentration, that at higher concentrations these compounds are expected to have NK binding inhibition activity.

The $K_i$ of a compound is that concentration at which the compound caused 50% inhibition of either $NK_1$ or $NK_2$. For those compounds of the invention having higher than 50% inhibition of $NK_1$, $K_i$'s for $NK_1$ were determined. The $K_i$'s for $NK_1$ for such compounds fell within a range of about 0.1 nM to about 1 μM.

For those compounds of the invention having higher than 50% inhibition of $NK_2$, $K_i$'s for $NK_2$ were determined. The $K_i$'s for $NK_2$ for such compounds fell within a range of about 0.1 nM to about 1 μM.

Compounds of formula I exhibit $NK_1$ and $NK_2$ antagonist activity to varying degrees, i.e., certain compounds have strong $NK_1$ antagonist activity, but weaker $NK_2$ antagonist activity. Others are strong $NK_2$ antagonists, but weaker $NK_1$ antagonists. Certain compounds have both strong $NK_1$ and $NK_2$ antagonist activities. Some compounds can also be $NK_3$ antagonists.

Many compounds of formula I have an asymmetric center and therefore exist as a pair of enantiomers. In such cases, one enantiomer can have different biological activity than the other. For example, one enantiomer can have strong $NK_1$ activity and weak $NK_2$ activity while the other enantiomer has weak $NK_1$ activity and strong $NK_2$ activity.

Certain compounds of formula I have been found to be antagonists of both $NK_1$ and $NK_2$ receptors, and are therefore useful in treating conditions caused or aggravated by the activity of $NK_1$ and $NK_2$ receptors.

The present invention also relates to a pharmaceutical composition comprising a compound of formula I and a pharmaceutically acceptable carrier. Compounds of this invention can be administered in conventional oral dosage forms such as capsules, tablets, powders, cachets, suspensions or solutions, or in injectable dosage forms such as solutions, suspensions, or powders for reconstitution. The pharmaceutical compositions can be prepared with conventional excipients and additives, using well known formulation techniques. Pharmaceutically acceptable excipients and additives include nontoxic and chemically compatible fillers, binders, disintegrants, buffers, preservatives, antioxidants, lubricants, flavorings, thickeners, coloring agents, emulsifiers and the like.

The daily dose of a compound of formula I for treating asthma, cough, bronchospasm, inflammatory disease, migraine, nociception and gastrointestinal disorders is about 0.1 mg to about 20 mg/kg of body weight per day, preferably about 0.5 to about 15 mg/kg, more preferably 0.5 to about 5 mg/kg. For an average body weight of 70 kg, the dosage range is therefore from about 1 to about 1500 mg of drug per day, preferably about 50 to about 100 mg, given in a single dose or 2–4 divided doses. The exact dose, however is determined by the attending clinician, and is dependent on the potency of the compound administered, the age, weight, condition and response of the patient.

The invention disclosed herein is exemplified by the following examples, which should not be construed to limit the scope of the disclosure. Alternative mechanistic pathways and analogous structures within the scope of the invention will be apparent to those skilled in the art.

EXAMPLE 1

2-(3,4-dichlorophenyl)piperazine

A. Synthesis of racemic compound 2-(3,4-Dichlorophenyl)piperazine was synthesized according to the method published in *J. Med.Chem.* 9,181, 1966.

A. General method for the synthesis of 2-aryl-piperazine derivatives.

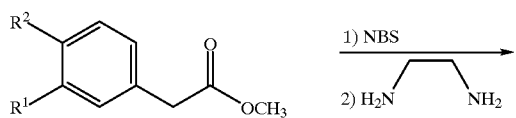

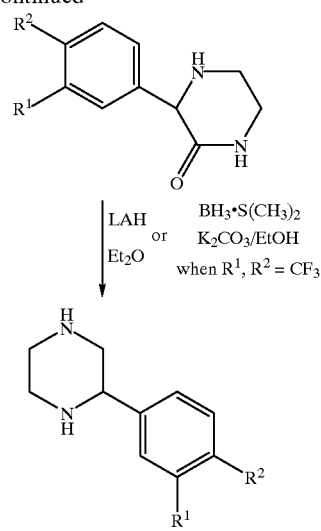

$R^1$=Cl, H or other substituents i.e. $OCH_3$, $CF_3$, Br, I, F, etc.

$R^2$=Cl, H or other substituents i.e. $OCH_3$, $CF_3$, Br, I, F, etc.

B. Resolution of 2-(3,4-dichlorophenyl)piperazine

Step 1

A solution of 2-(3,4-dichlorophenyl)piperazine (36.05 g, 0.156 mol) in $CH_3OH$ (200 mL) was treated with a solution containing two equivalents of N-acetyl-L-leucine (54.02 g, 0.312 mol) and heated until all of the material was dissolved. EtOAc (2.2 L) was added to this solution and allowed to stand at ambient temperature overnight. The solvent phase was decanted from the precipitated salt and concentrated in vacuo. This procedure was repeated using 37.88 g of 2-(3,4-dichloro-phenyl)piperazine (0.164 mol) and 56.68 g of N-acetyl-L-leucine (0.327 mol).

Step 2

The concentrated salts from both solvent phases in step 1 were combined and heated in methanol (550 mL) until all of the material dissolved. EtOAc (2.75 L) was added to this solution and allowed to stand at ambient temperature overnight. The solvent phase was decanted from the precipitated salt and concentrated in vacuo to give ~95 g of piperazine salt (72% ee of enantiomer A).

Step 3

The salt from the solvent phase in step 2 was dissolved in a solution of $H_2O$ (800 mL) and aq. ammonia (400 mL) and extracted with $CH_2Cl_2$ (4×400 mL). The combined organic layers were dried with $MgSO_4$ and concentrated to give 37 g of the piperazine free base. The free base was recrystallized three times from hexane (890, 600 and 450 mL) to give 16 g of piperazine (>99.9% ee of enantiomer A).

$[\alpha]24.7°$ C.=−45.0°(MeOH)

Step 4

The precipitated salts from step 1 were combined and heated in methanol (220 mL) until all of the material dissolved. EtOAc (2.2 L) was added to this solution and allowed to stand at ambient temperature overnight. The solvent phase was decanted from the precipitated salt and dried in vacuo to give ~43 g of piperazine salt (93% ee of enantiomer B).

Step 5

A 12.3 g portion of salt (75% ee of enantiomer B) prepared by an analogous procedure to that in step 4 was dissolved in 0.5M NaOH (400 mL) and extracted with CH₂Cl₂ (4×155 mL). The combined organic layers were dried with MgSO₄ and concentrated to give 3.72 g of the piperazine free base. The free base was recrystallized twice from hexane (90 and 70 mL) to give 2.1 g of piperazine (98% ee of enantiomer B).

C. Analytical procedure for measuring piperazine enantiomeric purity

The enantiomeric purity of the piperazine was measured by chiral HPLC analysis of the di-tert-butoxycarbonyl piperazine derivative. The di-tert-butoxycarbonyl derivative was prepared by adding a small piperazine sample (free base or salt)(~0.2 mg) to di-tert-butyl dicarbonate (~1 mg) and methanol (0.5 mL) and heating at 80° C. for 1 h. If the piperazine sample is a salt, triethylamine (20 μL) is also added. The derivative was analyzed by HPLC using a ChiralPak AD column eluting with 95:5 hexane-isopropyl alcohol.

EXAMPLE 2

(±)-[3,5-dimethylbenzoyl]-3-(3,4-dichlorophenyl) piperazine

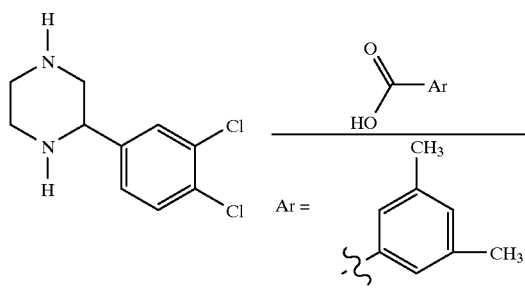

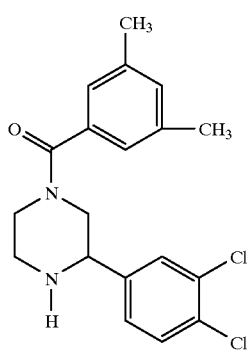

To a cooled solution of CH₂Cl₂ (600 mL) containing 2-(3,4-dichlorophenyl)piperazine (6.934 g, 30 mmol), 3,5-dimethylbenzoic acid (4.55 g, 30 mmol), and N-hydroxybenzotriazole monohydrate (4.05 g, 30 mmol) at −20° C. were added Et₃N (4.2 mL, 30 mmol) and N,N-dimethylaminopropylethylcarbodimide (DEC) (5.86 g, 30 mmol) under nitrogen. The reaction was kept at −20° C. for an hour and gradually warmed to RT overnight. After stirring 22 hours, the reaction was complete and CH₂Cl₂ (200 mL) was added. The organic solution was washed with brine (150 mL, 3×), dried over MgSO₄, filtered and concentrated under vacuum to give 8.2 g of crude product. The product was crystallized from CH₂Cl₂/Hexane to give a light yellow solid (6.3 g, 17.34 mmol, 57.8%). Mm.p.139–141° C.; FAB MS [M+1]⁺³⁵Cl 363.1.

EXAMPLE 3

(±)-bromoacetyl-2-(3,4-dichlorophenyl)-4-(3,5-dimethylbenzoyl)piperazine

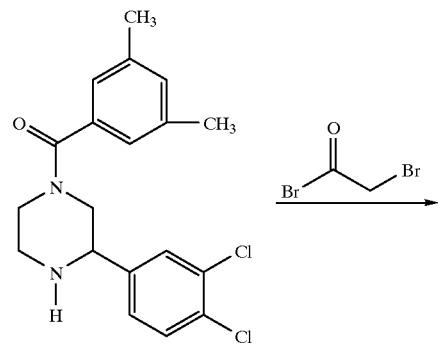

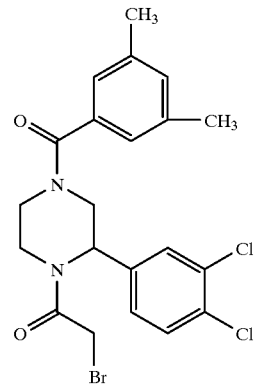

To a cooled solution of (±)-[3,5-dimethylbenzoyl]-3-(3,4-dichlorophenyl)piperazine (11.5 g, 31.65 mmol) in CH₂Cl₂ (200 mL) at 0° C. was added Hünig's base (4.5 g, 35 mmol) and bromoacetyl bromide (6.4 g, 31.65 mmol). The solution was stirred at 0° C. overnight under N₂. After completion the reaction was diluted with CH₂Cl₂ (400 mL) and washed with brine (300 mL, 2×), dried over MgSO₄, filtered and concentrated. The crude material was purified by flash grade silica gel chromatography, eluting with 2% [NH₄OH/MeOH (1:9)]/98% CH₂Cl₂ to give the title compound as a light yellow solid (7.1 g, 47.3%), m.p. 77–79° C., FAB MS [M+1]⁺³⁵Cl, ⁷⁹Br 482.9, 484.9.

EXAMPLE 4

(+)-[3,5-dimethylbenzoyl]-3(R)-(3,4-dichlorophenyl) piperazine (Enantiomer B)

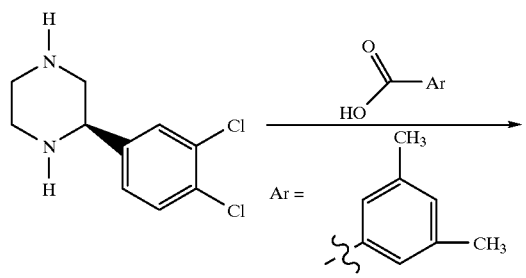

-continued

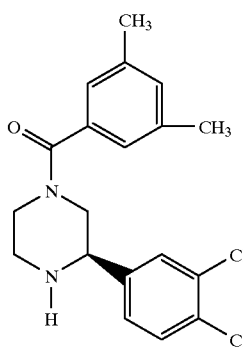

The title compound was prepared by an analogous method to that described in Example 2 using (−)2(R)-(3,4-dichlorophenyl)piperazine in place of (±)-2-(3,4-dichlorophenyl)piperazine, m.p. 97–100° C.; FAB MS [M+1]$^{+35}$Cl 363.1; [α]$_D^{22.5°\ C.}$=+87.2°(MeOH).

EXAMPLE 5

(−)-bromoacetyl-2(R)-(3,4- dichlorophenyl)-4-(3,5-dimethylbenzoyl)piperazine (Enantiomer B)

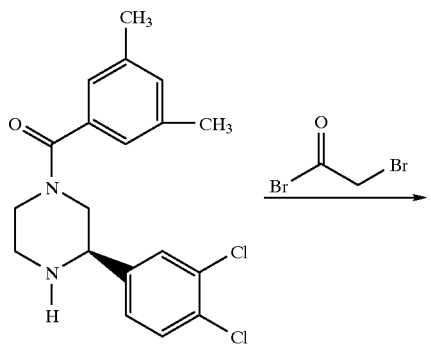

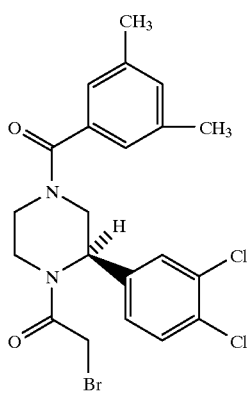

The title compound was prepared by an analogous method to that described in Example 3 using (+)-[3,5-dimethylbenzoyl]-3(R)-(3,4-dichlorophenyl)piperazine (Enantiomer B) (Example 4) in place of (±)-[3,5-dimethylbenzoyl]-3-(3,4-dichlorophenyl)piperazine, m.p. 68–71° C., FAB MS [M+1]$^{+35}$Cl $^{79}$Br 482.9, 484.8; [α]$_D^{21.9°\ C.}$=−45.6°(MeOH).

EXAMPLE 6

1,1-Dimethylethyl 5-amino-2-azabicyclo[2.2.1]heptane-2-carboxylate (F)

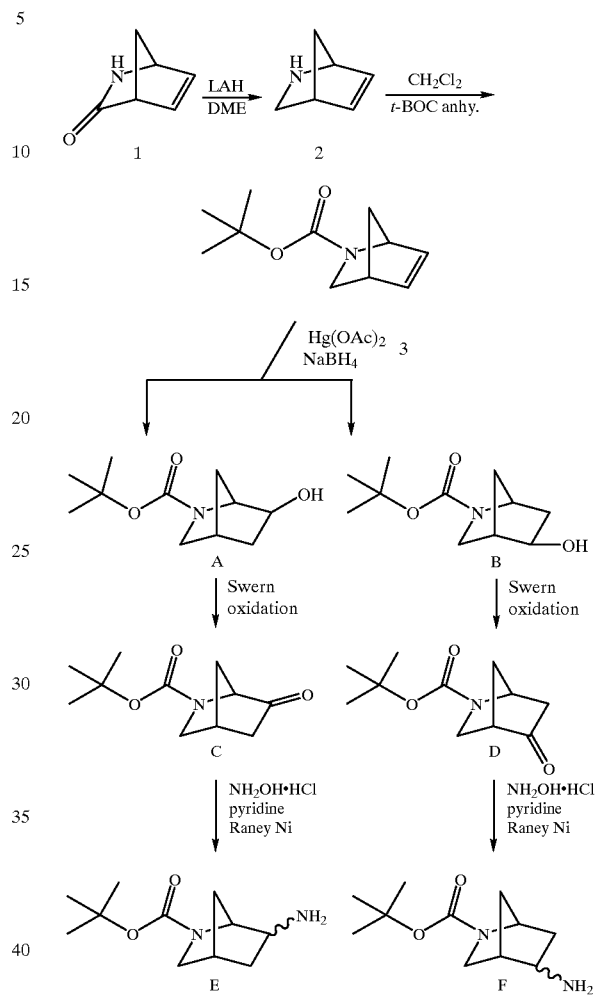

Step 1

To a solution of (±)-2-azabicyclo[2.2.1.]hept-5-en-3-one (3.9 g, 35.7 mmol) in DME (100 mL) at 0° C. was slowly added a1M solution of LAH/THF (180 mL, 180 mmol) under N$_2$. After addition, the mixture was refluxed for 2 h then cooled to RT. Excess LAH was quenched slowly with saturated Na$_2$SO$_4$ solution (50 mL) while keeping the reaction vessel under N$_2$ in a dry-ice acetone bath at −78° C. After stirring overnight, white solid was filtered off and the filtrate was acidified with 1M HCl in ether, then concentrated to give compound 2 as a brown solid (3.5 g, 26.6 mmol, 75%) as HCl salt, FAB MS [M+1]$^+$96.

Step 2

To a suspension of compound 2 (3.93 g, 29.8 mmol) (obtained from two batches) in CH$_2$Cl$_2$ (40 mL) was added Hünig's base (5.6 g, 29.8 mmol). To this solution of compound 2 was slowly added a solution of t-BOC anhydride (6.5 g, 29.8 mmol) in CH$_2$Cl$_2$ (30 mL) at RT under N$_2$. After stirring at RT overnight, the reaction was washed with water (100 mL, 2×), dried with Na$_2$SO$_4$, and filtered. The filtrate was evaporated to dryness under vacuum to give compound 3 (5.5 g, 28.17 mmol, 94.5%) as a brown liquid. FAB MS [M+1]$_+$196.4.

Step 3*

To a cooled yellow suspension of Hg(OAc)$_2$ (9 g, 28.2 mmol) in H$_2$O (30 mL) and THF (23 mL) at 0° C. was added dropwise compound 3 (5.5 g, 28.17 mmol). The mixture was stirred at RT for 16 h and followed by the addition of 0.5M NaBH$_4$ in 3N NaOH (30 mL). The mixture turned black and Hg was allowed to settle. The supernatant liquid was decanted and extracted with ether (70 mL, 2×), dried (Na$_2$SO$_4$), filtered and concentrated to give a light brown oil (5.5 g). The crude material was separated by flash chromatography on silica gel, eluting with 30% EtOAc/Hexane to give compound (A) as an oil (2 g, 9.37 mmol, 33%), FAB MS [M+1]$^+$214.4 and compound (B) as an oil (1.5 g, 7 mmol, 25%), FAB MS [M+1]$^+$214.4.

*H. Firouzubadi, *Bull.Chem.Soc. Jpn.*, 56, 1983), p.914

Step 4

To a solution of oxalyl chloride (2.1 g, 16.2 mmol) in dry CH$_2$Cl$_2$ (90 mL) at −78° C. was added DMSO (1.9 g, 24.3 mmol). After stirring for 1 h, a solution of compound (B) (1.73 g, 8.1 mmol) and Et$_3$N (8.2 g, 81 mmol) in dry CH$_2$Cl$_2$ (50 mL) was added by cannulation. The mixture was stirred at −78° C. for 2 h then allowed to warm to RT. After reaction was complete, EtOAc (300 mL) was added and the resultant solution was washed with saturated NaHCO$_3$ (2×200 mL), brine (200 mL), dried (MgSO$_4$), filtered, and evaporated to give compound (D) as a brown oil, FAB MS [M+1]$^+$212.3.

Step 5

A mixture of compound (D) (1.7 g, 8 mmol) and hydroxylamine hydrochloride (0.56 g, 8 mmol) in pyridine (6 mL) was heated at 100° C. (oil bath temperature) for 8 h. After reaction was complete, excess pyridine was removed to give a residue which was redissolved in CH$_2$Cl$_2$ (100 mL), washed with brine (50 mL,3×), dried (MgSO$_4$), filtered, and evaporated to give the oxime derivative of compound (D) as a brown gum (1.6 g, 7 mmol), FAB MS [M+1]$^+$227.3.

Step 6

To a suspension of Raney Nickel (5 g, washed with abs. EtOH 3×) in abs. EtOH (40 mL) was added the oxime derivative of compound (D) (1.56 g, 6.89 mmol). The mixture was hydrogenated at 49 psi in a Parr shaker for 24 h. After completion, Raney Nickel was filtered off (caution; risk of fire) and the filtrate was concentrated to give an oil which was redissolved in CH$_2$Cl$_2$ (50 mL), washed with sat'd NaHCO$_3$ (50 mL, 2×), dried (Na$_2$SO$_4$), filtered, and concentrated to give the title compound (F) as an oil (1.0 g, 0.47 mmol), FAB MS [M+1]$^+$213.2.

EXAMPLE 7

1,1-Dimethylethyl 5-[[2(R)-[2-(3,4-dichlorophenyl)-4-(3,5-dimethylbenzoyl)-1-piperazinyl]-2-oxoethyl] amino]-2-azabicyclo[2.2.1]heptane-2-carboxylate, diastereomers

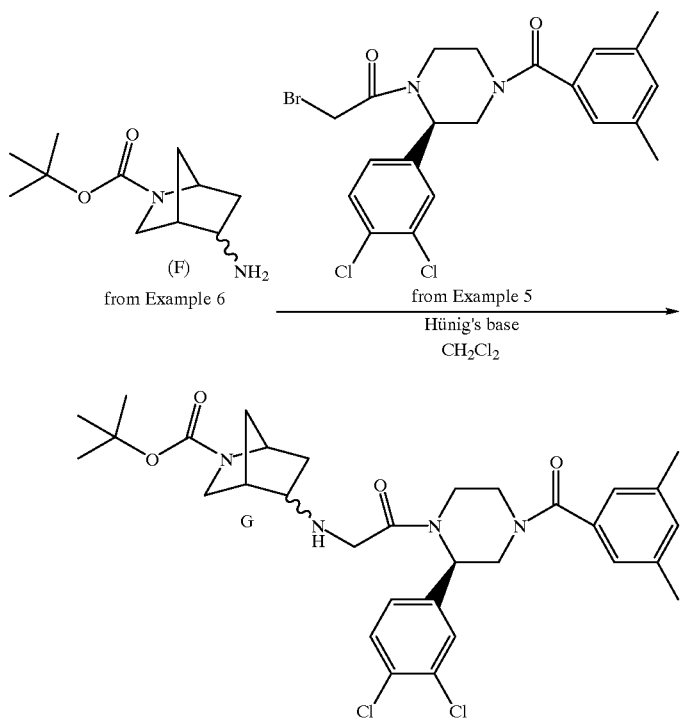

To a solution of bromoacetamide intermediate (from Example 5) (0.8 g, 1.65 mmol) in dry CH$_2$Cl$_2$ (10 mL) was added a solution of compound (F) (Example 6) (0.9 g, 4.24 mmol) in dry CH$_2$Cl$_2$ (10 mL) and Hünig's base (0.21 g, 1.65 mmole). After stirring at RT overnight, the reaction was diluted with CH$_2$Cl$_2$ (100 mL) and washed with brine (50 mL ×3), dried (MgSO$_4$), filtered, and concentrated to yield a brown solid (1 g). The crude material was purified by flash chromatography on silica gel (120 g), eluting with 4% [(1:9) NH$_4$OH/MeOH]/96% CH$_2$Cl$_2$ to give the title compound (G) as a tan solid (0.73 g, 1.18 mmol, 72%), FAB MS [M+1]$^{+35}$Cl 615.1

EXAMPLE 8

2(R)-(3,4-Dichlorophenyl)-4-(3,5-dimethylbenzoyl)-1-[[[2-azabicyclo[2.2.1]heptan-5-yl]amino]acetyl]piperazine, diastereomers

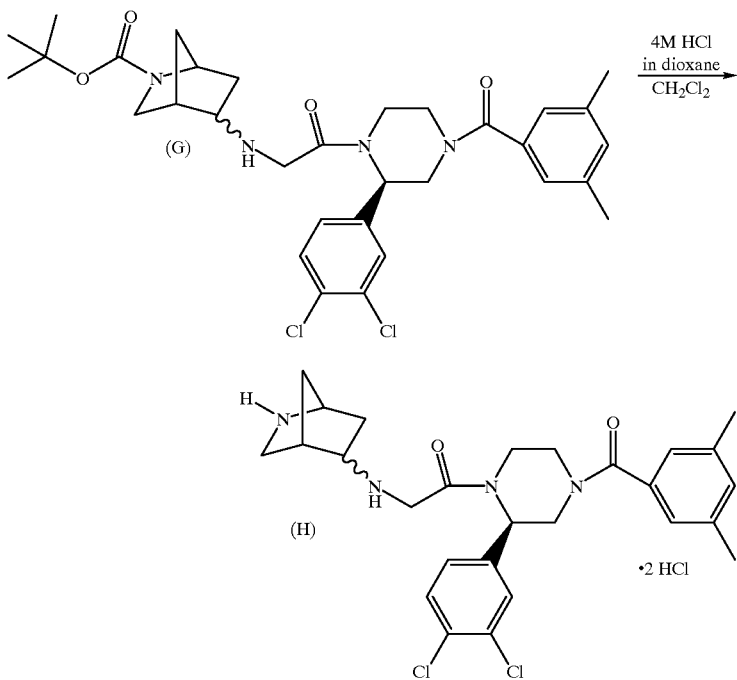

To a solution of compound (G) (Example 7) (0.54 g, 0.88 mmole) in dry $CH_2Cl_2$ (2 mL) was added 4M HCl/dioxane (2.2 mmol) solution. The mixture was stirred at RT for 2 h and excess HCl and solvents were evaporated to give the title compound (H) as its 2 HCl salt (0.51 g, 0.88 mmol), FAB MS $[M+1]^{+35}Cl$ 515.4.

EXAMPLE 9

2(R)-(3,4-Dichlorophenyl)-4-(3,5-dimethylbenzoyl)-1-[[[2-(phenylmethyl)-azabicyclo[2.2.1]heptan-5-yl]amino]acetyl]piperazine, diastereomers

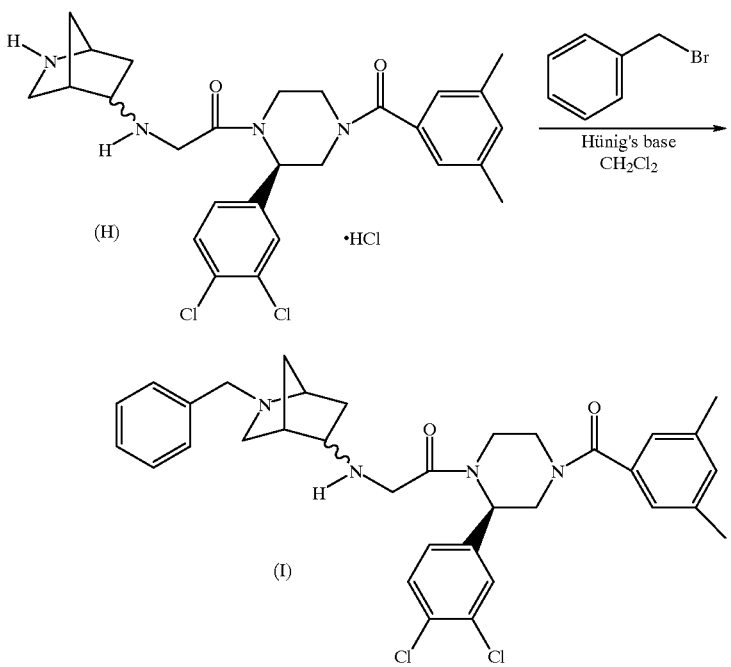

A mixture of compound (H) (Example 8) (0.2 g, 0.34 mmol), Hünig's base (0.15 g, 1.2 mmol) and benzyl bromide (58 mg, 0.34 mmole) in $CH_2Cl_2$ (3 mL) was stirred at RT for 2 days. After reaction was complete, CH$_2$Cl$_2$ (30 mL) was added and the mixture was washed with water (30 mL, 2×), dried (MgSO$_4$), filtered, and concentrated to give a brown gummy solid (0.2 g). The crude material was purified by flash chromatography on silica gel (50 g), eluting with 5% [(1:9) (NH$_4$OH/CH$_3$OH)]/95% CH$_2$Cl$_2$ to give the title compound as a white solid, m.p. 69–71° C., FABMS [M+1]$^{+35}$Cl 605.0; HR MS [M+H]$^+$calc'd for C$_{34}$H$_{39}$N$_4$O$_2$Cl$_2$ 605.2450; Found 605.2449.

EXAMPLE 10

2(R)-(3,4-Dichlorophenyl)-4-(3,5-dimethylbenzoyl)-1-[[[2-(phenylmethyl)-azabicyclo[2.2.1]heptan-5-yl]amino]acetyl]piperazine, diastereomers A and B The compound obtained from Example 9 was separated on a YMC phenyl column, eluting with CH$_3$OH:H$_2$O:TFA (60:40:0.1%) with a flow rate of 0.8 mL/min. It was resolved into two compounds with retention times of 7.78 min (diastereomer A) and 9.35 min (diastereomer B). Both diastereomers are white solids after evaporating solvent.

EXAMPLE 11

2(R)-(3,4-Dichlorophenyl)-4-(3,5-dimethylbenzoyl)-1-[[[2-(phenylmethyl)-azabicyclo[2.2.1]heptan-5-yl]amino]acetyl]piperazine, enantiomers 1 and 2

Diastereomer B obtained from Example 10 was separated on a ChiralPak AD (Daicel) column, eluting with hexane:CH$_3$OH:EtOH:Et$_2$N (20:40:40:0.1), with a flow rate of 0.6 mL/min. It was resolved into two enantiomers with retention times of 10.97 min (enantiomer 1) and 12.49 min (enantiomer 2). Both enantiomers are solids after evaporating solvent.

EXAMPLE 12

2(R)-(3,4-Dichlorophenyl)-4-(3,5-dimethylbenzoyl)-1-[[[2-(phenylmethyl)-azabicyclo[2.2.1]heptan-5-yl]amino]acetyl]piperazine, enantiomers 3 and 4

Diastereomer A obtained from Example 10 was separated on a ChiralPak AD (Daicel) column, eluting with hexane:CH$_3$OH:EtOH:Et$_2$N (20:40:40:0.1), with a flow rate at 0.6 mL/min. It was resolved into two enantiomers with retention times of 14.91 min (enantiomer 3) and 17.98 min (enantiomer 4). Both enantiomers are white solids after evaporating solvent.

EXAMPLE 13

2(R)-(3,4-Dichlorophenyl)-4-(3,5-dimethylbenzoyl)-1-[[[2-(4-acetyamino-phenylmethyl)-azabicyclo[2.2.1]heptan-5-yl]amino]actyl]piperazine, diastereomers

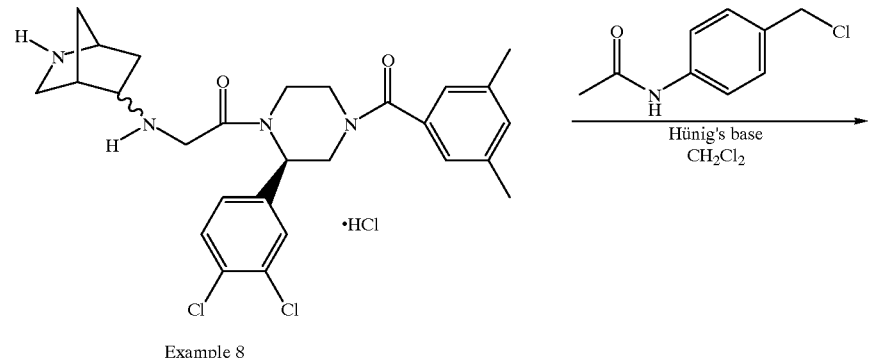

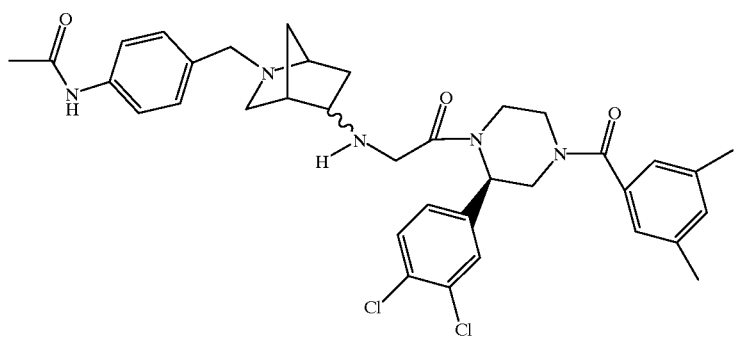

By an analogous method to that described in Example 9, using the compound from Example 8, and with 4-acetamidobenzyl chloride replacing benzyl bromide, the title compound was obtained as a white solid after silica gel chromatography purification. M.p. 110–112° C.; High Res MS Calc'd for [M+H]⁺ $C_{36}H_{42}N_5O_3Cl_2$ 662.2665, Found 662.2674.

EXAMPLE 14

N-[4-[[5-[[2-[2(R)-(3,4-Dichlorophenyl)-4-(3,5-dimethylbenzoyl)-1-piperazinyl]-2-oxoethyl]amino]-2-azabicyclo[2.2.1]heptan-2-yl]methyl-2-thiazolyl]acetamide (diastereomers)

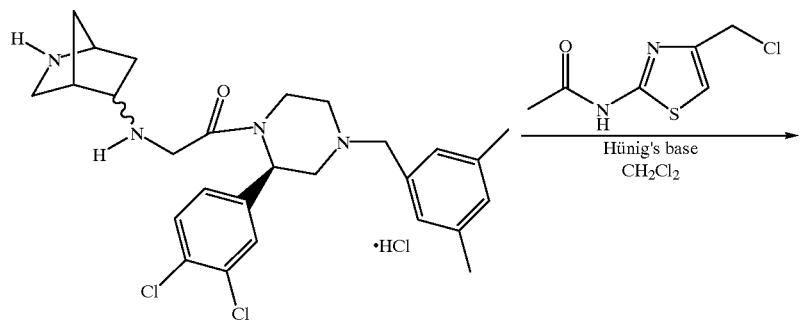

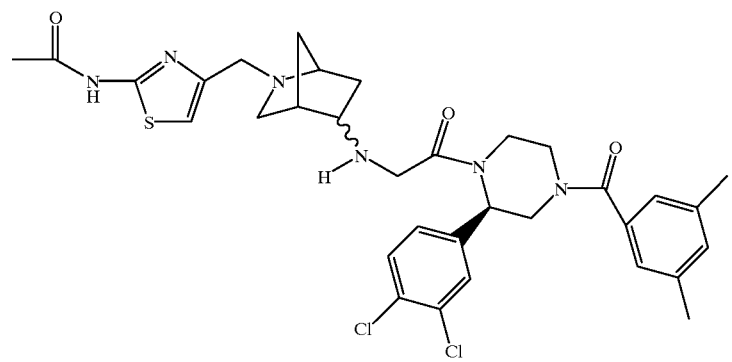

By an analogous method to that described in Example 9, using the compound from Example 8, and with 2-acetamido-4-chloromethyl-thiazole replacing benzyl bromide, the title compound was obtained as a white solid after silica gel chromatography. M.p. 135–137° C.; High Res MS [M+H]⁺ Cacl'd for $C_{33}H_{39}N_6O_3SCl_2$ 669.2181, Found 669.2186.

EXAMPLE 15

(−)-1,1-Dimethylethyl 2-[3-[2(R)-(3,4-dichlorophenyl)-4-(dimethylbenzoyl)-1-piperazinyl]-3-oxopropyl]-1(S), 4(S)-2,5- diazabicyclo[2.2.1]heptane-5-carboxylate

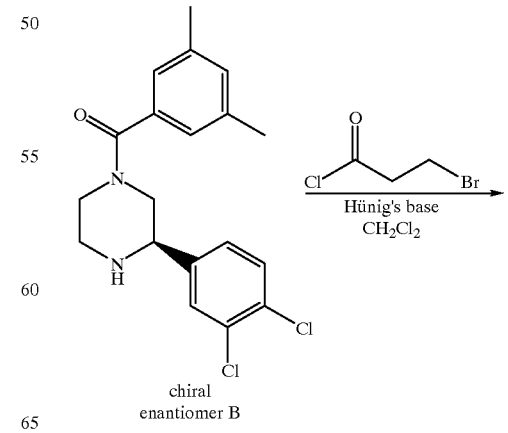

-continued

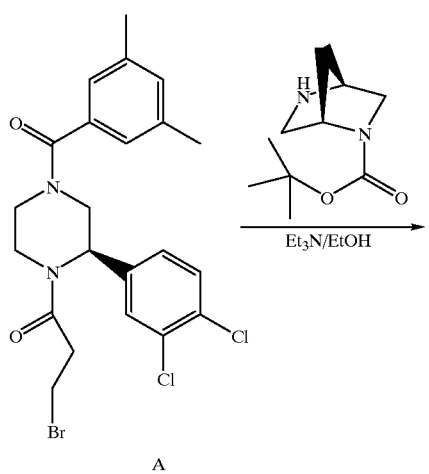

A

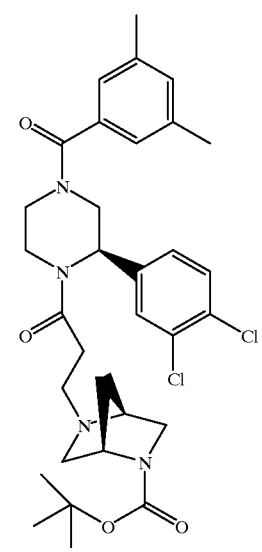

Part 1

To a solution of (+)-[3,5-dimethylbenzoyl]-3(R)-(3,4-dichlorophenyl)-piperazine (Enantiomer B) (Example 4) (20.7 g, 57 mmol) in dry $CH_2Cl_2$ (320 mL) at $-78°$ C. was added 3-bromopropionyl chloride (9.8 g, 57 mmol) and $Et_3N$ (5.76 g, 57 mmole). After stirring at $-78°$ C. for 4 h, additional 3-bromopropionyl chloride (0.5 ml, 4.96 mmol) and $Et_3N$ (0.5 ml, 4 mmol) were added. A portion of the material (40 mL) was worked up by diluting with $CH_2Cl_2$ (100 mL) and washing with water, similar to the procedures described in Example 4, to give the bromopropionyl intermediate A as shown above. FAB MS $[M+1]^{+35}Cl$, $^{79}Br$ 498.9, 500.9.

Part 2

The remainder of the above reaction product was evaporated without water washing to give a brown solid (25 g, 50.5 mmole) which was redissloved in absolute EtOH (200 mL) and cooled to 0° C. To this cooled solution was added (1S,4S)-N-t-BOC-2,5-diazabicyclo[2.2.1]-heptane (9.0 g, 45.5 mmol) and $Et_3N$ (4.1 g, 40.4 mmol). The solution was stirred overnight at RT. After the reaction was complete, EtOH was evaporated off, the residue was redissolved in $CH_2Cl_2$ (500 mL) and washed with brine (300 mL, 3×), dried ($MgSO_4$), filtered and concentrated to give a tan crude product (30 g). The crude material was purified by flash chromatography on flash grade silica gel (400 g), eluting with 3% [(1:9) ($NH_4OH:CH_3OH$)]/97% $CH_2Cl_2$ to give the title compound as an off white solid (15.5 g, 25.1 mmol, 55%), m.p. 78–82° C.; FAB Mass $[M+1]^{+35}Cl$ 615.1; $[\alpha]_D^{22°}$ c. (MeOH)=−51.1°

EXAMPLE 16

(−)-1-[3-[(1S), 4(S)-2,5-Diazabicyclo[2.2.1]heptan-2-yl]-1-oxopropyl]-2(R)-(3,4-dichlorophenyl)-4-(3,5-dimethylbenzoyl)piperazine hydrochloride salt

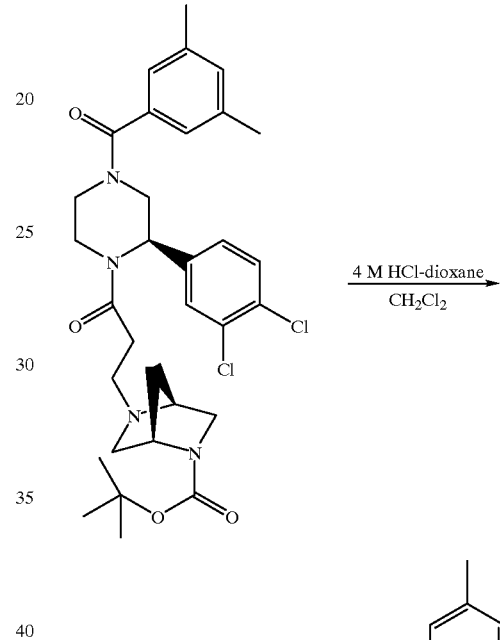

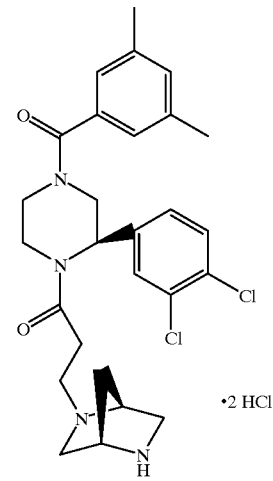

To a solution of the compound obtained from Example 15 (14.5 g, 23.55 mmol) in $CH_2Cl_2$ (25 mL) at RT was added 4M HCl/dioxane (58.8 mL, 235.2 mmol) solution. The mixture was stirred at RT for 2 hours and excess acid and solvents were evaporated off to give the title compound as a light yellow solid, 15.5 g; m.p.60–64° C.; FAB MS $[M1]^{+35}Cl$ 515.2 ; $[\alpha]_D^{22°\ c.}$ (MeOH) =−34.4°

EXAMPLE 17

1,1-Dimethylethyl [2-[5-[3-[2(R)-(3,4-dichlorophenyl)-4-(3,5-dimethylbenzoyl)-1-piperazinyl]-3-oxopropyl]-1(S), 4(S)-2,5-diazabicyclo[2.2.1]heptan-2-yl]-2-oxo-1(R)-phenylethyl] carbamate (Enantiomer B)

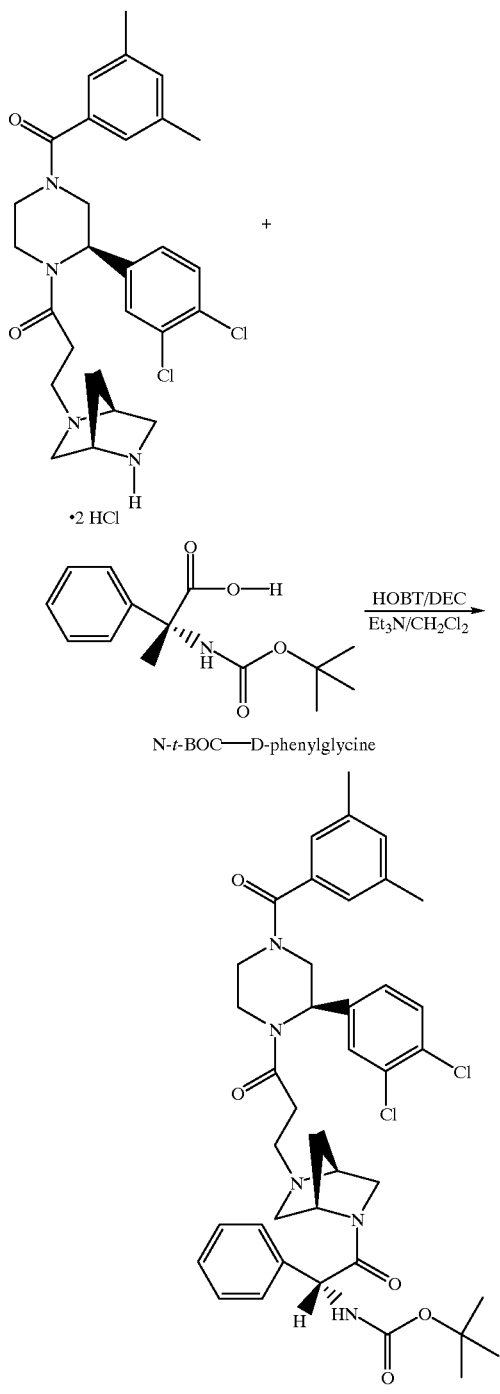

To a solution of the compound from Example 16 (0.3 g, 0.51 mmol) in CH$_2$Cl$_2$ (5 mL) was added Hünig's base (0.23 g, 1.8 mmol), N-t-BOC-D-phenylglycine (0.13 g, 0.51 mmol), HOBT (69 mg, 0.51 mmol) and DEC (98 mg, 0.51 mmol). After stirring overnight at RT, the reaction was diluted with CH$_2$Cl$_2$ (50 mL), washed with water (30 mL, 3×), dried (MgSO$_4$), filtered, and concentrated to give a crude product (0.4 g). The crude material was purified by flash chromatography on silica gel (40 g), eluting with 3% [(NH$_4$OH-CH$_3$OH) (1:9)]/97% CH$_2$Cl$_2$ to give the title compound as a white solid (0.25 g, 0.33 mmol, 65%), m.p. 120–122° C.; FAB MS [M+1]$^{+35}$Cl 748.3.

EXAMPLE 18

2-[(R)-Amino(phenyl)acetyl]-5-[3-[2(R)-(3,4-dichlorophenyl)-4-(3,5-dimethylbenzoyl)-1-piperazinyl]-3-oxopropyl]-1(S), 4(S)-2,5-diazabicyclo[2.2.1]heptane, dihydrochloride (Enantiomer B)

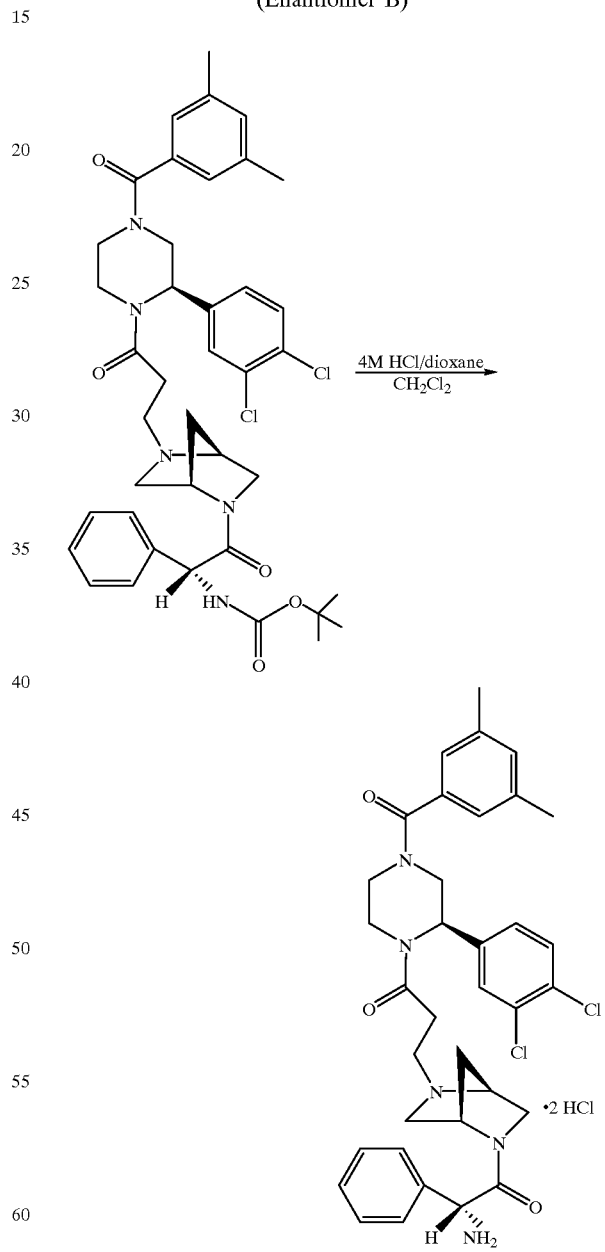

To a solution of the compound from Example 17 (0.20 g, 0.267 mmol) in CH$_2$Cl$_2$ (1 mL) was added 4M HCl-dioxane (3 mL, 12 mmol) solution. The mixture was stirred at RT for one hour. Solvents and excess HCl were evaporated to give the title compound as a white solid (0.19 g, 0.267 mmol), m.p. >210° C.; FAB MS [M+1]$^{+35}$Cl 721.56.

EXAMPLE 19

A number of N-t-BOC-D-or L- amino acid derivatives of the product from Example 16 were prepared according to the method described in Example 17, using N-t-BOC-D-amino acids or N-t-BOC-L-amino acids in place of N-t-BOC-D-phenylglycine.

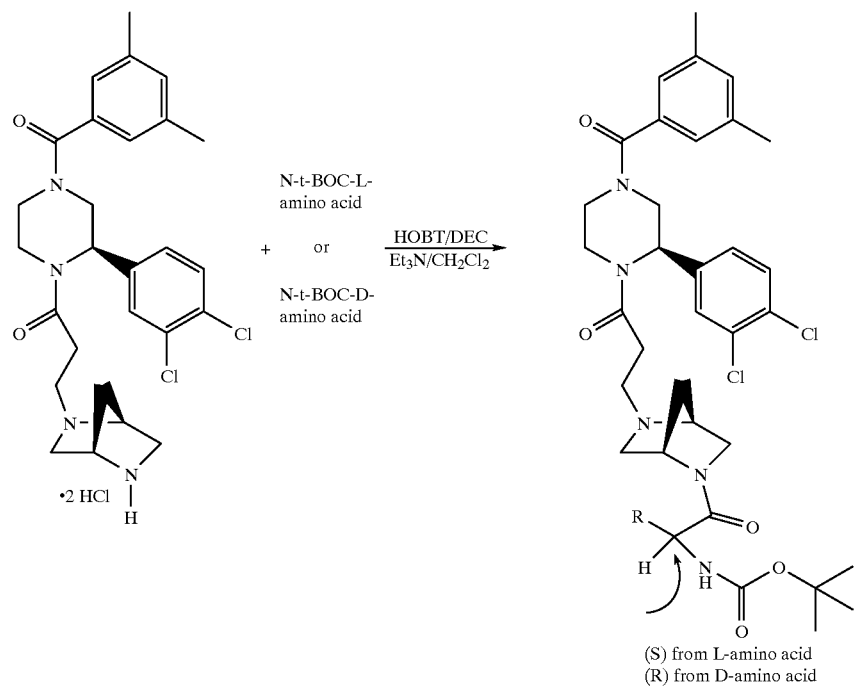

| Amino Acid | R | m.p. ° C. | FAB MS [M + 1]$^{+35}$ Cl |
|---|---|---|---|
| N-t-BOC-L-phenylalanine | —CH$_2$Ph | 105–110 | 762.2 |
| N-t-BOC-L-tyrosine | —CH$_2$—C$_6$H$_4$—OH | 134–136 | 778.4 |
| N-t-BOC-L-phenylglycine | —Ph | 109–112 | 748.4 |
| N-t-BOC-D-phenylalanine | —CH$_2$Ph | 103–105 | 762.4 |
| N-t-BOC-D-phenylglycine | —Ph | 120–122 | 748.3 |
| N-t-BOC-β-2-thienyl-D-alanine | —CH$_2$-(2-thienyl) | 146–150 | 768.3 |

| | | | |
|---|---|---|---|
| -continued | | | |
| N-t-BOC-β-2-thienyl-L-alanine | 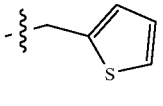 β | 106–108 | 768.3 |
| N-t-BOC-D-tyrosine | 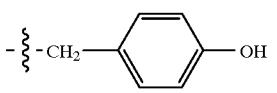 | 165–169 | 778.2 |
| N-t-BOC-β-(3-pyridyl)-D-alanine | 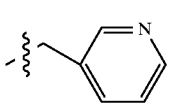 β | 132–135 | 763.1 |
| N-t-BOC-β-(2-pyridyl)-D-alanine | 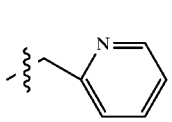 β | 156–159 | 763.4 |

EXAMPLE 20

The N-t-BOC-D-or L-amino acid derivatives listed in Example 19 were converted to the corresponding D- or L-amino acid derivatives according to the method described in Example 18.

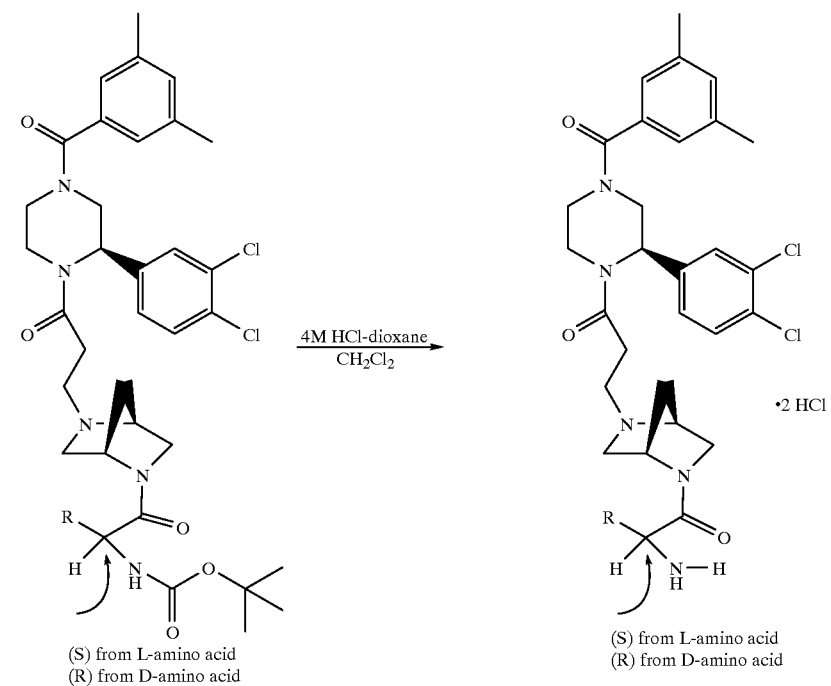

| Amino Acid | R | m.p. °C. | FAB MS [M + 1]$^{+35}$ Cl |
|---|---|---|---|
| N-t-BOC-L-phenylalanine |  -CH$_2$Ph | 205–207 | 662.2 |
| N-t-BOC-L-tyrosine | 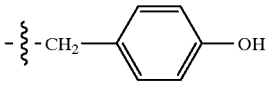 -CH$_2$-⌬-OH | >210 | 678.3 |

-continued

| | | | |
|---|---|---|---|
| N-t-BOC-L-phenylglycine | -§-Ph | 215–220 | 648.3 |
| N-t-BOC-D-phenylalanine | -§-CH₂Ph | 195–203 | 662.4 |
| N-t-BOC-D-phenylglycine | -§-Ph | >210 | 648.1 |
| N-t-BOC-β-2-thienyl-D-alanine | -§-CH₂-(2-thienyl) β | 200–205 | 668.0 |
| N-t-BOC-β-2-thienyl-L-alanine | -§-CH₂-(2-thienyl) β | 197–198 | 668.1 |
| N-t-BOC-D-tyrosine | -§-CH₂-C₆H₄-OH | 210–220 | 678.2 |
| N-t-BOC-β-(3-pyridyl)-D-alanine | -§-CH₂-(3-pyridyl) β | 215–220 | 663.1 |
| N-t-BOC-β-(2-pyridyl)-D-alanine | -§-CH₂-(2-pyridyl) β | 195–198 | 663.1 |

EXAMPLE 21

Preparation of N-[2-[5-[3-[2(R)-(3,4-Dichlorophenyl)-4-(3,5-dimethylbenzoyl)-1-piperazinyl]-3-oxopropyl]-1(S), 4(S)-2,5-diazabicyclo[2.2.1]heptan-2-yl]-2-oxo-1-phenylethyl]acetamide (Enantiomer B)

By a method analogous to that described in Example 17, but using N-acetyl-D,L-phenylglycine in place of N-t-BOC-D-phenylglycine, the title compound was obtained as a white foam, m.p.115–119° C.; FAB MS [M+1]$^{+35}$Cl 690.3.

EXAMPLE 22

(±)-1,1-Dimethylethyl-4-[[2-[2-(3,4-dichlorophenyl)-1-(3,5-dimethylbenzoyl)-1-piperazinyl]-2-oxoethyl]amino]-1-piperidine carboxylate

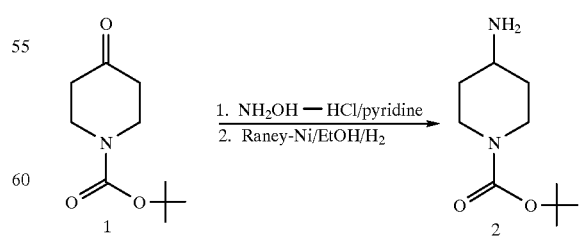

1. NH₂OH—HCl/pyridine
2. Raney-Ni/EtOH/H₂

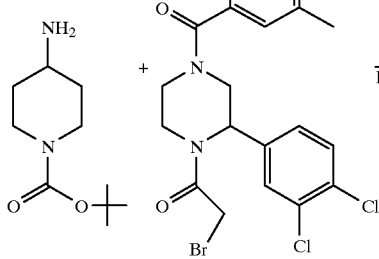

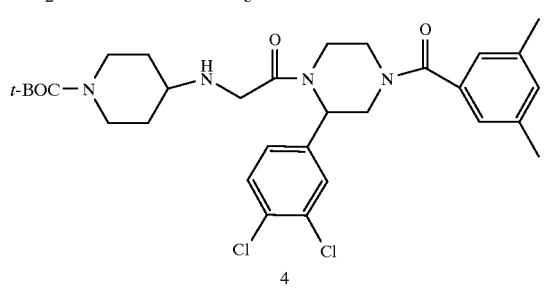

To a solution of N-t-butoxycarbonyl-4-piperidone 1 (15 g, 75.3 mmol) in pyridine (50 mL) was added hydroxylamine • HCl (5.23 g, 75.3 mmol). The mixture was heated in an oil bath at 65° C. for 1 h. After cooling, pyridine was removed under reduced pressure and the residue was dried under high vacuum overnight to give a solid. To this solid was added water (100 mL) and the mixture was sonicated. The precipitate was filtered and washed with water then dried under high vacuum to give the oxime derivative of compound 1 (10.5 g, 65%); FAB MS [M+1]$^+$215.3. The oxime (10 g, 46.67 mmol) was dissolved in absolute EtOH (100 mL) followed by the addition of Raney Ni (29 g, washed with absolute EtOH). The mixture was hydrogenated in a Parr shaker at 50 psi overnight. After reaction was complete, the Raney Ni was filtered off (caution; risk of fire) and the filtrate was concentrated to give compound 2 (9.2 g, 46 mmol,98% yield) as an oil which solidified under high vacuum drying. FAB MS [M+1]$^+$201.3.

To a solution of the bromoacetamide derivative 3 (3.0 g,6.2 mmol) (prepared in Example 3) in $CH_2Cl_2$ (62 mL) at −10° C. were added Hünig's base (1.2 mL, 6.82 mmol) and compound 2 (2.48 g, 12.39 mmol). The solution was gradually warmed to RT overnight. After reaction was complete, $CH_2Cl_2$ (300 mL) was added and the mixture was washed with brine (100 mL, 3x), dried over $MgSO_4$ and filtered. The filtrate was evaporated to dryness to give a light yellow solid which was purified by flash chromatography on silica gel (200 g), eluting with 5% [$NH_4OH$/MeOH (1:9)]/ $CH_2Cl_2$ to give a 71% yield of the title compound 4 as a white solid (2.66 g, 4.4 mmol), m.p. 78–81° C.; FAB MS [M+1]$^{+35}$Cl 603.1; Calcd. for $C_{31}H_{40}N_4O_4Cl_2$, C, 61.69; H, 6.68; N, 9.28; Cl, 11.74. Found: C, 61.33; H, 6.94; N, 9.17; Cl, 11.27.

EXAMPLE 23

(−)-1,1-Dimethylethyl 4-[[2-[2(R)-(3,4-dichlorophenyl)-1-(3,5-dimethylbenzoyl)-1-piperazinyl]-2-oxoethyl]amino]-1-piperidinecarboxylate (Enantiomer B)

By employing methods analogous to those described in Example 22, using the chiral bromoacetamide compound (prepared in Example 5), the title compound was obtained as a white solid, m.p.72–75° C.; FAB MS [M+1]$^{+35}$Cl 603.2; $[\alpha]_D^{22° C.}$=−32.8°(MeOH).

EXAMPLE 24

(±)-2-(3,4-Dichlorophenyl)-4-[3,5-dimethylbenzoyl]-1-[(4-piperidinylamino)acetyl] piperazine, dihydrochloride

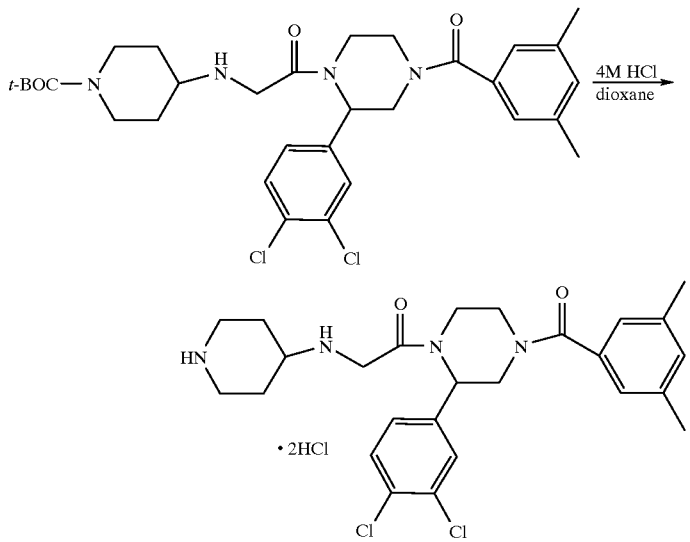

To a solution of (±)-1,1-dimethylethyl-4-[[2-[2-(3,4-dichlorophenyl)-1-(3,5-dimethylbenzoyl)-1-piperazinyl]-2-oxoethyl]amino]-1-piperidine-carboxylate (Example 22) (2.5 g, 4.14 mmol) in $CH_2Cl_2$ (20 mL) at 0° C. was added 4M HCl-dioxane (10.35 mL, 41.4 mmol). The mixture was stirred at 0° C. for 1 h, then it was gradually warmed to RT over 3 h. After reaction was complete, excess HCl and solvent were evaporated to give a pale yellow solid which was used without further purification. FAB MS [M+1]$^{+35}$Cl 503.1

EXAMPLE 25

(−)-2(R)-(3,4-Dichlorophenyl)-4-[3,5-dimethylbenzoyl]-1-[(4-piperidinyl-amino)acetyl]piperazine, dihydrochloride (Enantiomer B)

By employing a method analogous to that described in Example 24, but using chiral material obtained from Example 23, the title compound was obtained as a pale yellow solid, FAB MS [M+1]$^{+35}$Cl 503.2; $[\alpha]_D^{22.1°C.}=-38°$ (MeOH)

EXAMPLE 26

A number of N-t-BOC-D-or L- amino acid derivatives of the product from Example 25 were prepared according to the methods described in Example 17, using the compound from Example 25 and N-t-BOC-D-amino acids or N-t-BOC-L-amino acids in place of N-t-BOC-D-phenylglycine.

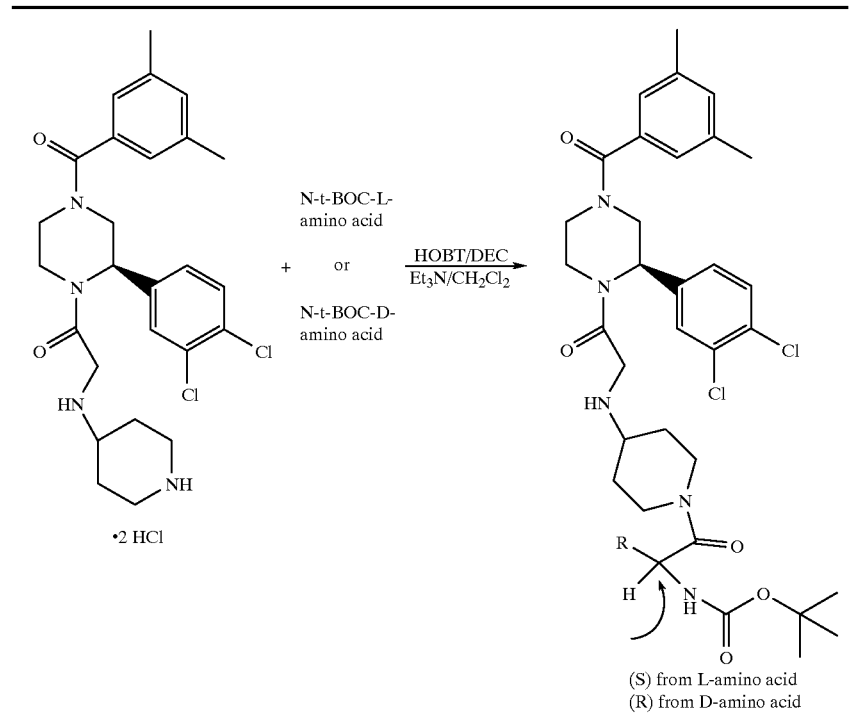

| Amino Acid | R | m.p. °C. | FAB MS [M + 1]$^{+35}$ Cl |
|---|---|---|---|
| N-t-BOC-L-phenylalanine | −CH$_2$Ph | 94–98 | 750.1 |
| N-t-BOC-L-tyrosine | −CH$_2$−⟨C$_6$H$_4$⟩−OH | 150–153 | 766.0 |
| N-t-BOC-L-phenylglycine | −Ph | 110–113 | 736.3 |
| N-BOC-L-histamine | −CH$_2$-(imidazole) | 126–129 | 740.1 |
| N-BOC-L-tryptophan | (indol-3-yl) | 153–156 | 789.0 |

| | | -continued | | |
|---|---|---|---|---|
| N(a)-t-BOC-L-asparagine | -$\xi$-CH$_2$CONH$_2$ | | 85–90 | 717.1 |
| N-t-BOC-L-serine | -$\xi$-CH$_2$OH | | 105–108 | 690.1 |
| N-t-BOC-D-phenylalanine | -$\xi$-CH$_2$Ph | | 98–101 | 750.4 |
| N-t-BOC-D-phenylglycine | -$\xi$-Ph | | 92–99 | 736.2 |

EXAMPLE 27

The N-t-BOC-D-or L-amino acid derivatives listed in Example 26 were converted to the corresponding D- or L-amino acid derivatives according to the method described in Example 18.

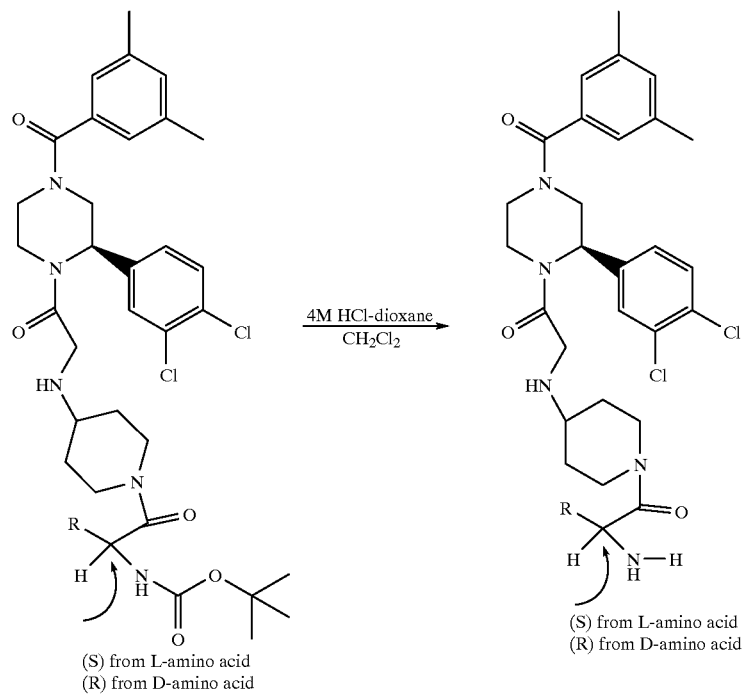

| Amino Acid | R | m.p. °C. | FAB MS [M+ 1]$^{+35}$ Cl or HRMS [M +H]$^{+35}$ Cl |
|---|---|---|---|
| L-phenylalanine | -$\xi$-CH$_2$Ph | 200–210 | calc'd 650.2665 found 650.2672 |
| L-tyrosine | -$\xi$-CH$_2$-⟨⟩-OH | 215–218 | calc'd 665.2536 found 665.2537 |
| L-phenylglycine | -$\xi$-Ph | 200–210 | 636.3 |

| | | | |
|---|---|---|---|
| -continued | | | |
| L-histamine | {CH2-imidazole} | 222–226 | calc'd 640.2570 found 640.2578 |
| L-tryptophan | {CH2-indole} | 218–222 | calc'd 689.2774 found 689.2766 |
| L-asparagine | -CH$_2$CONH$_2$ | 190–200 | calc'd 617.2410 found 617.2405 |
| L-serine | -CH$_2$OH | 200–210 | calc'd 590.2301 found 590.2205 |
| D-phenylalanine | -CH$_2$Ph | 210–220 | 650.3 |
| D-phenylglycine | -Ph | >210 | 636.1 |

EXAMPLE 28

2(R)-(3,4-Dichlorophenyl)-4-(3,5-dimethylbenzoyl)-1-[1-oxo-3-[5-phenylsulfonyl)-2,5-diazabicyclo[2.2.1]heptan-2-yl]propyl]piperazine

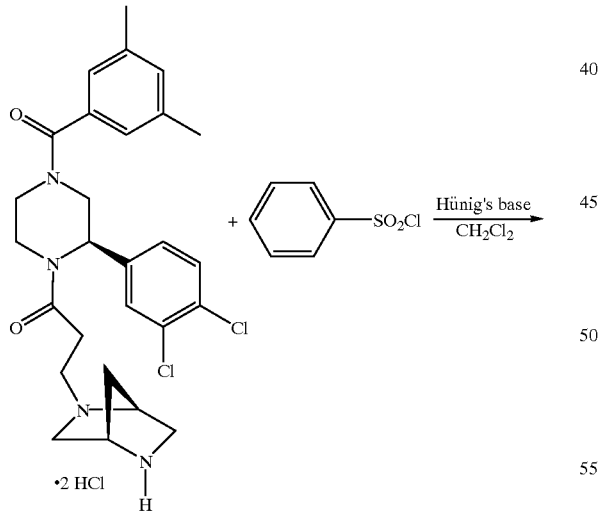

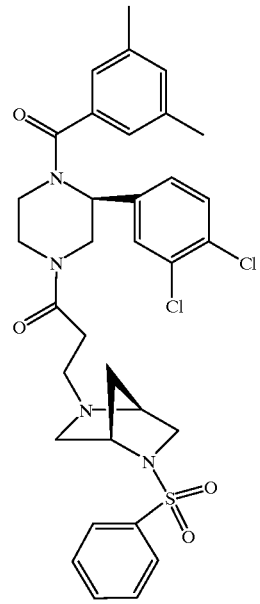

To a solution of the compound obtained from Example 16 (206 mg, 0.35 mmole) in CH$_2$Cl$_2$ (4 mL) was added Hünig's base (0.18 g, 1.4 mmol) and phenylsulfonyl chloride (70 mg, 0.39 mmol). The solution was stirred at RT under N$_2$. After reaction was complete, the reaction was diluted with CH₂Cl₂ (40 mL) and washed with water (30 mL, 3×), dried (Na₂SO₄), filtered, and concentrated to give a white solid. The crude material was purified by flash chromatography on silica gel (40 g), eluting with 4% [NH₄OH:CH₃OH (1:9)]/ 96% CH₂Cl₂ to give the title compound as a white solid. m.p. 93–95° C.; FAB MS [M+1]$^{+35}$Cl 655.2

EXAMPLE 29

5-[1-Cyanoimino)-1-methylthio]-2-[3-[2(R)-(3,4-dichlorophenyl)-4-(3,5-dimethylbenzoyl)-1-piperazinyl]-3-oxopropyl-2,5-diazabicyclo[2.2.1]heptane

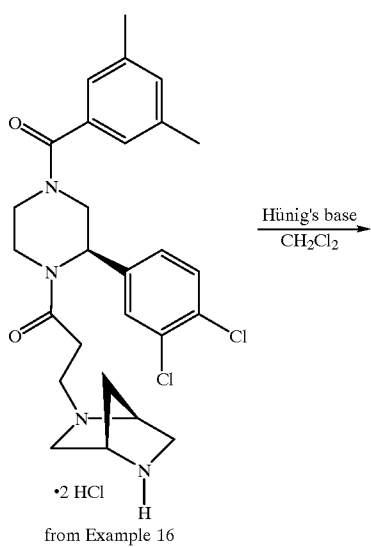

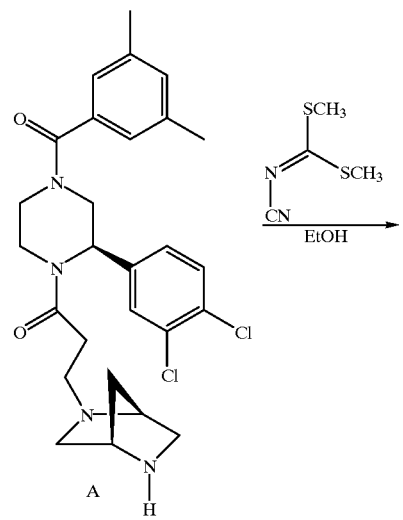

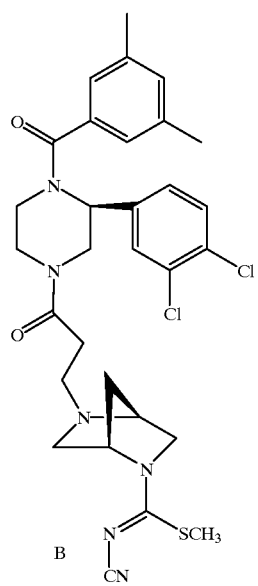

Step 1

To a solution of compound from Example 16 (1.0 g, 1.7 mmol) in CH₂Cl₂ (100 mL) was added Hünig's base (0.621 mL, 3.57 mmol). After stirring at RT for 15 min, the reaction was diluted with CH₂Cl₂ (100 mL), washed with brine (30 mL, 3×), dried (MgSO₄), filtered, and concentrated to give compound A (0.7 g, 11.9 mmol, 70%) as a white solid.

Step 2

A mixture of compound A (0.5 g, 0.85 mmol) in absolute EtOH (5 mL) and dimethyl-N-cyanodithioimine (150 mg, 0.93 mmol) was heated under N₂ in an oil bath at 80° C. overnight. After completion, N₂ was bubbled through the reaction solution and EtOH was evaporated off under reduced pressure to give an oil which was purified by flash chromatography on silica gel (100 g), eluting with 5% [NH₄OH:CH₃OH (1:9)]/95% CH₂Cl₂ to give the title compound as a white solid, m.p. 91–93° C.; FAB MS [M+1]⁺ ₃₅Cl 613.2.

EXAMPLE 30

5-[1-(cyanoimino)-1-phenylaminomethyl]-2-[3-[2(R)-(3,4-dichlorophenyl)-4-(3,5-dimethylbenzoyl)-1-piperazinyl]-3-oxopropyl-2,5-diazabicyclo[2.2.1]heptane

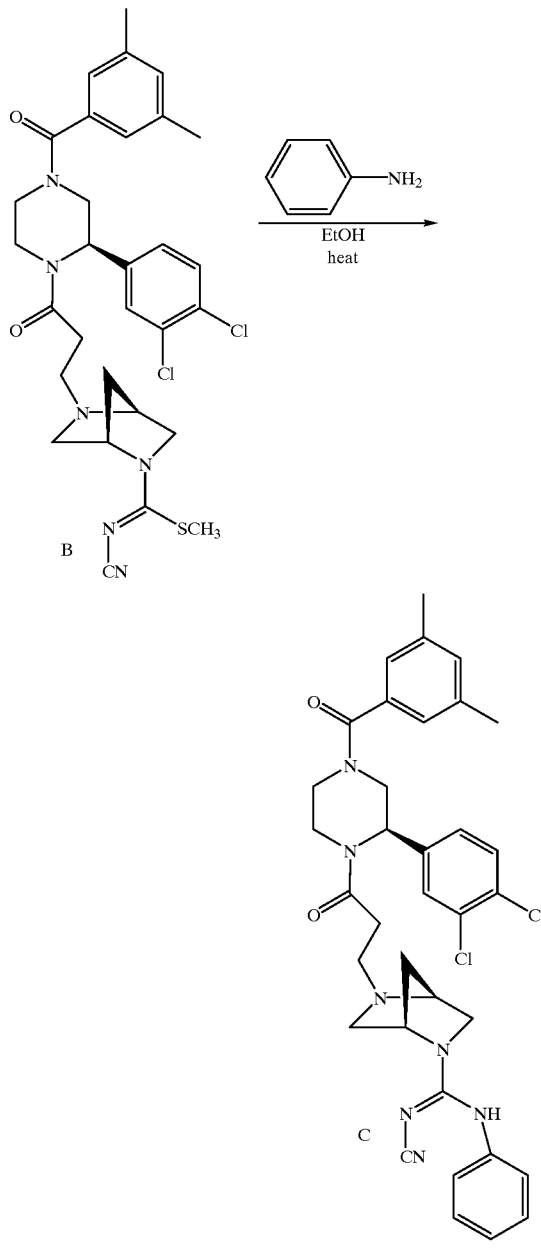

EXAMPLE 31

5-[1-(Cyanoimino)-1-phenylmethylaminomethyl]-2-[3-[2(R)-(3,4-dichlorophenyl)-4-(3,5-dimethylbenzoyl)-1-piperazinyl]-3-oxopropyl-2,5-diazabicyclo[2.2.1]heptane

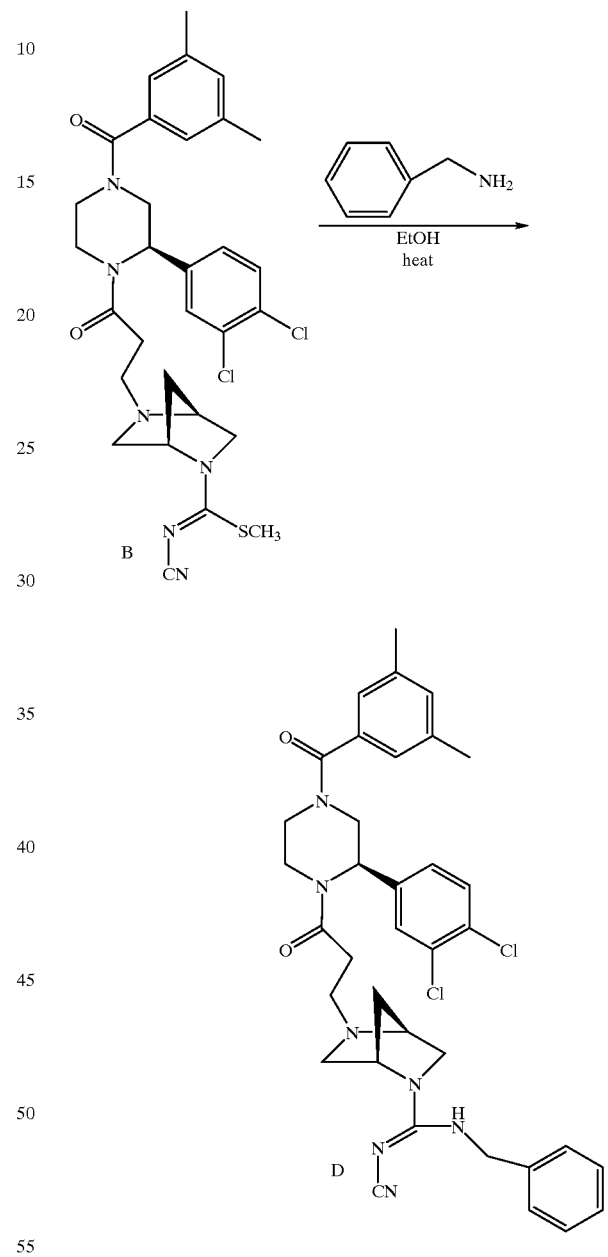

A mixture of compound B (Example 29) (0.2 g, 0.326 mmol) in $K_2CO_3$ in DMF and aniline (0.06 mL, 0.652 mmol) is heated under $N_2$ at 80° C. in an oil bath. The product is purified.

A mixture of compound B (Example 29) (0.2 g, 0.326 mmol) in $K_2CO_3$ in DMF and benzylamine (0.071 mL, 0.652 mmol) is stirred under $N_2$ at 80° C. The product is purified.

EXAMPLE 32
2(R)-(3,4-dichlorophenyl)-4-(3,5-dimethylbenzoyl)-
1-[[6-(phenylmethyl)-2-azabicyclo[2.2.2]octan-6-yl]
methylamino]acetyl]piperazine
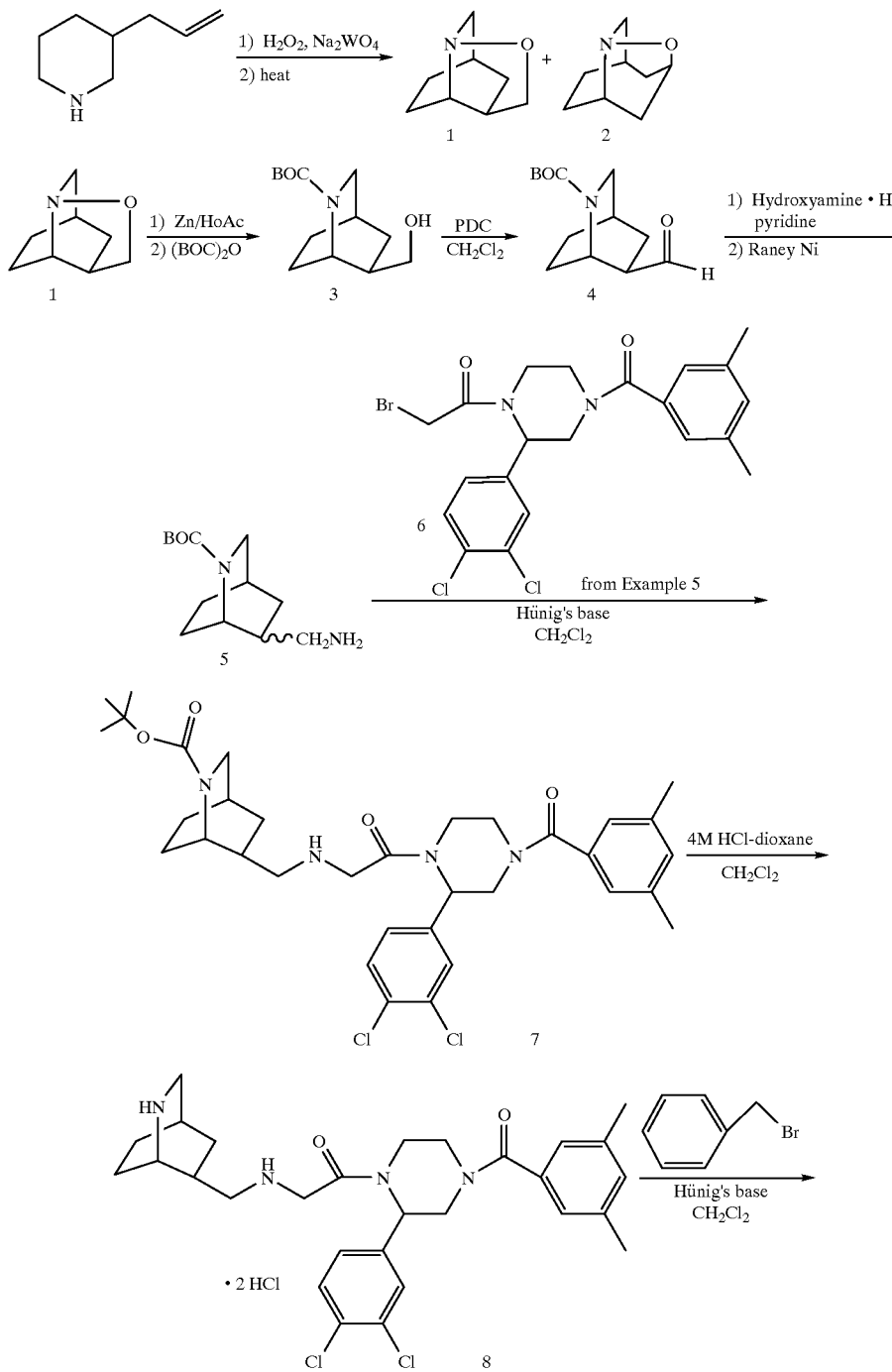

-continued

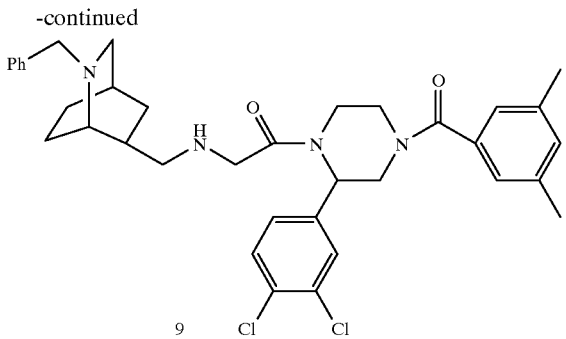

The title compound is prepared according to the scheme shown above by using the intramolecular 1,3-dipolar cycloaddition of nitrones to olefins (Chem. Comm., 874 (1984)) yielding polycyclic isovazolidines 1 and 2. Compound 1 is converted to compound 3 by hydrogenation of compound 1 and protection of the nitrogen with t-BOC anhydride. Convert compound 3 to the title compound 9 using methods analogous to those described in Examples 6, 7, 8 and 9.

EXAMPLE 33
2(R)-(3,4-Dichlorophenyl)-4-(3,5-dimethylbenzoyl)-1-[[6-(phenylmethyl)-6-azabicyclo[3.2.2.]nonan-3-yl]amino]acetyl]piperazine

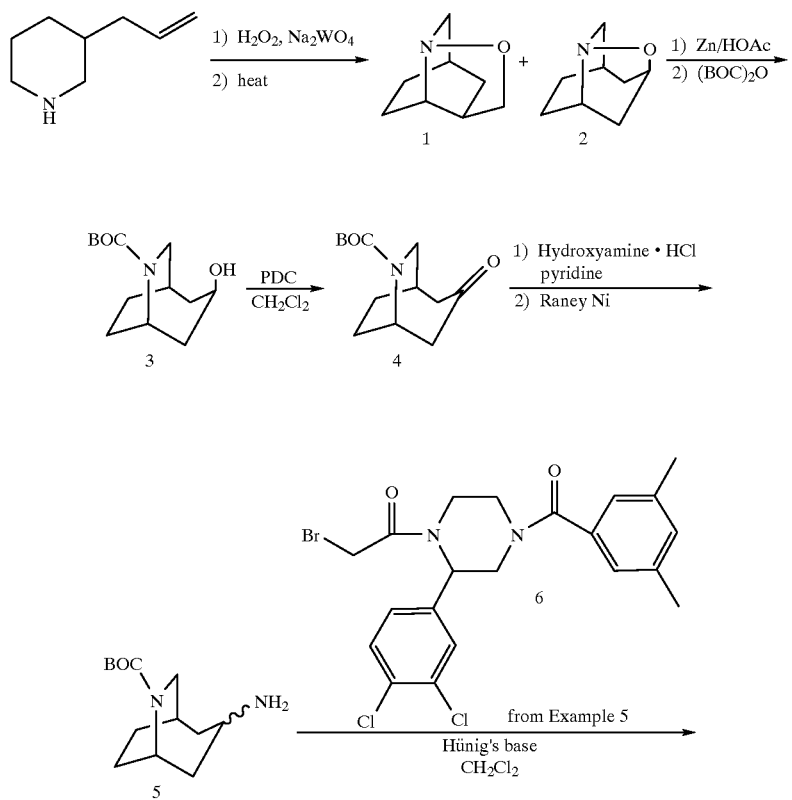

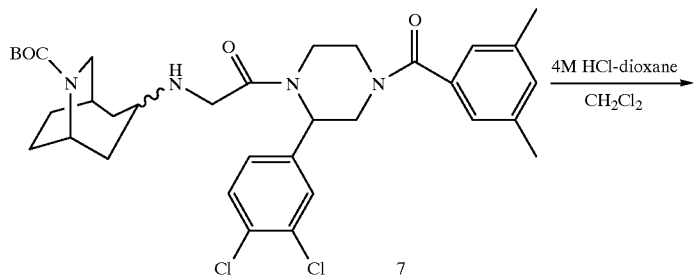

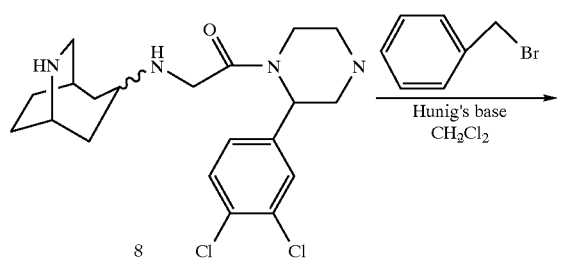

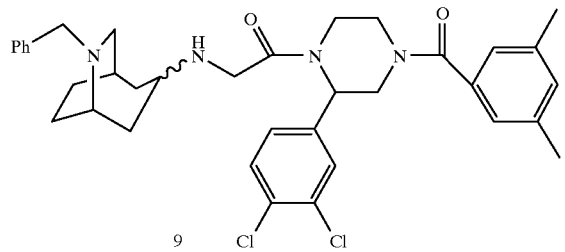

The title compound is prepared according to the scheme shown above by using the intramolecular 1,3-dipolar cycloaddition of nitrones to olefins (Chem. Comm., 874 (1984)) yielding polycyclic isovazolidines 1 and 2. Compound 2 is converted to compound 3 by hydrogenation and protection of the nitrogen with t-BOC anhydride. Convert compound 3 to the title compound 9 using methods analogous to those described in Examples 6, 7, 8 and 9.

EXAMPLE 34

Methyl [1(R)-[[5-[3-[2(R)-(3,4-dichlorophenyl)-4-(3,5-dimethylbenzoyl)-1-piperazinyl]-3-oxopropyl]-1(S),4(S)-2,5-diazabicyclo[2.2.1]heptan-2-yl]carbonyl-2-phenyl]carbamate (enantiomer B)

To a solution of compound (1) from Example 20 (74 mg, 0.1 mmol) in $CH_2Cl_2$ (2 mL) was added Hünig's base (56 μL, 0.32 mmol) and methyl chloroformate (8 μL, 0.103 mmol). The mixture was stirred at RT overnight. After reaction was complete, $CH_2Cl_2$ (5 mL) was added and washed with brine (2 mL, 3×), dried ($MgSO_4$), filtered and evaporated to dryness. Crude material was purified by flash chromatography on silica gel, eluting with 5% (1:9) [$NH_4OH$:$CH_3OH$]/95% $CH_2Cl_2$. The title compound was obtained as a white solid. All other analogs were prepared by the method just described, using appropriate chloroformate reagents. The physical data of these compounds are listed below.

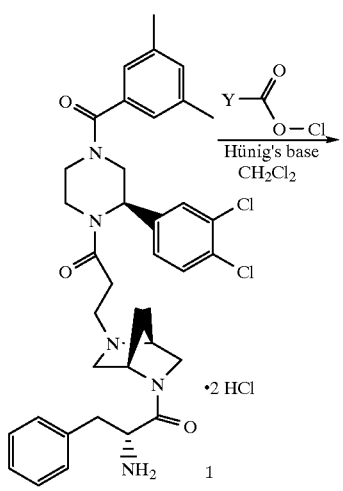

| Y | m.p. °C. | HR MS [M+1]$^{+35}$ Cl calculated | found |
|---|---|---|---|
| -$\xi$-CH$_3$ | 102–105 | 720.2720 | 720.2710 |
| -$\xi$-CH$_2$CH$_3$ | 95–98 | 734.2876 | 734.2870 |
| -$\xi$-CH(CH$_3$)$_2$ | 94–97 | 748.3033 | 748.3049 |
| -$\xi$-C(=CH$_2$)CH$_3$ | 94–96 | 746.2876 | 746.2888 |
| -$\xi$-CH$_2$CH(CH$_3$)$_2$ | 95–97 | 762.3189 | 762.3175 |

EXAMPLE 35

N-[1(R)-[(5-[3-[2(R)-(3,4-dichlorophenyl)-4-(3,5-dimethylbenzoyl)-1-piperazinyl]-3-oxopropyl]-1(S),4(S)-2,5-diazabicyclo[2.2.1]heptan-2-yl]carbonyl-2-phenylethyl]-N'-methylurea (enantiomer B)

By an analogous method to that described in Example 34, using methylisocyanate in place of methylchloroformate, the title compound was obtained as a white solid. All other analogs were prepared by the method according to that described in Example 34, using appropriate isocyanate reagents. The physical data of these compounds are listed in the following table.

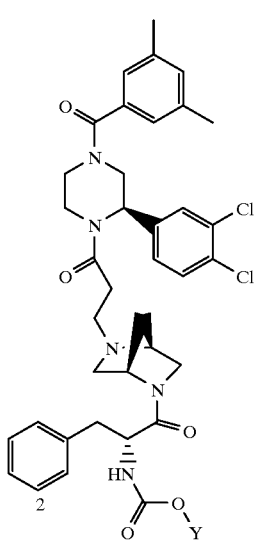

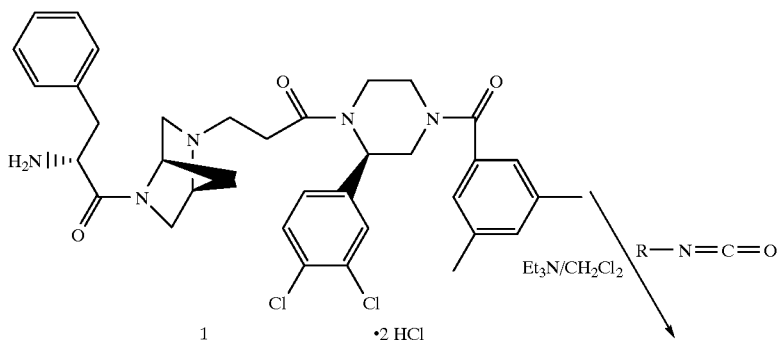

-continued
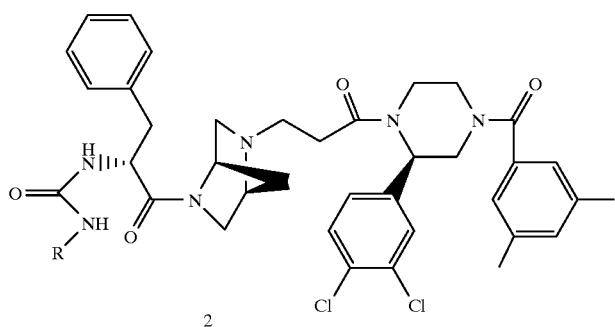
| R | m.p. °C. | HR MS [M +1]$^{+35}$ Cl calculated | found |
|---|---|---|---|
| -§-CH$_3$ | 156–160 | 719.2879 | 719.2872 |
| -§-CH$_2$CH$_3$ | 112–115 | 733.3036 | 736.3028 |
| -§-propyl | 145–148 | 747.3192 | 747.3198 |
| -§-isopropyl | 160–165 | 747.3192 | 747.3182 |
| -§-butyl | 150–154 | 761.3349 | 761.3346 |
| -§-isobutyl | 125–128 | 761.3349 | 761.3339 |
| -§-CH(iPr)C(O)OEt | 112–114 | 833.3560 | 833.3547 |
| -§-CH(iPr)C(O)OEt | 140–143 | 847.3717 | 847.3716 |
| -§-CH$_2$CH$_2$C(O)OEt | 125–128 | 805.3247 | 805.3248 |
| -§-cyclohexyl | 125–127 | 787.3505 | 787.3505 |

EXAMPLE 36

5-[3-[2(R)-(3,4-Dichlorophenyl)-4-(3,5-dimethylbenzoyl)-1-piperazinyl]-3-oxopropyl]-2-[2(R)-[[(methylamino)carbonyl]amino]-1-oxo-3-(2-thienyl)propyl]-1(S),4(S)-2,5-diazabicyclo[2.2.1]heptane (enantiomer B)

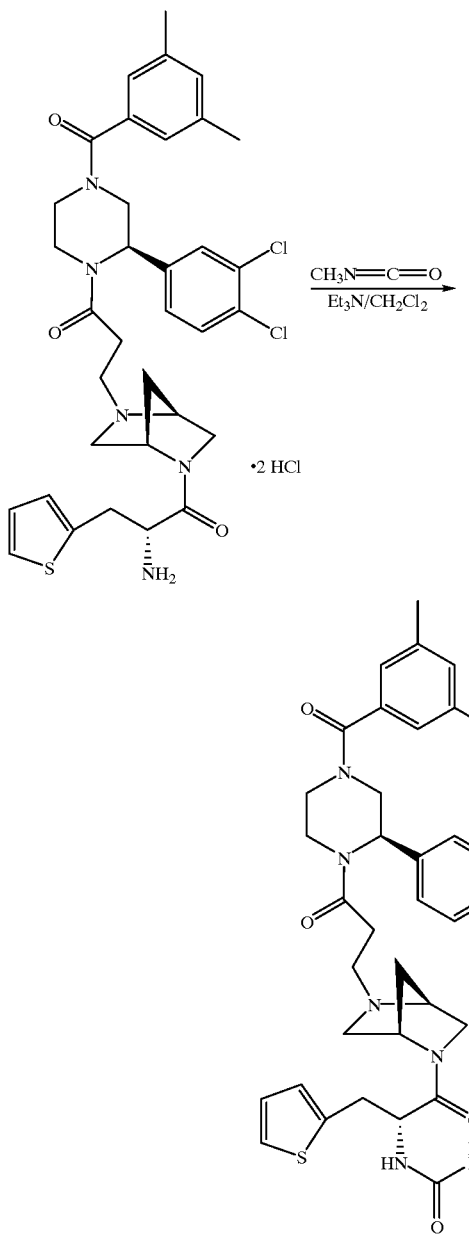

By employing methods analogous to those described for Examples 17, 18, 19 and 35 using N-t-BOC-D-thienylalanine replacing N-t-BOC-D-phenylglycine in Example 17, the title compound was obtained as a white solid after flash silica gel chromatography, m.p. 120–130° C.; HR MS [M+1]$^{+25}$Cl calculated: 725.2444, found 725.2452.

EXAMPLE 37

2-[3-[2-(R)-(3,4-Dichlorophenyl)-4-(3,5-dimethylbenzyoyl)-1-piperazinyl]-3-oxopropyl]-5-[2-[[imino(methylamino)methyl]amino]-1-oxo-3-phenylpropyl]-1(S),4(S)-2,5-diazobicyclo[2.2.1]heptane

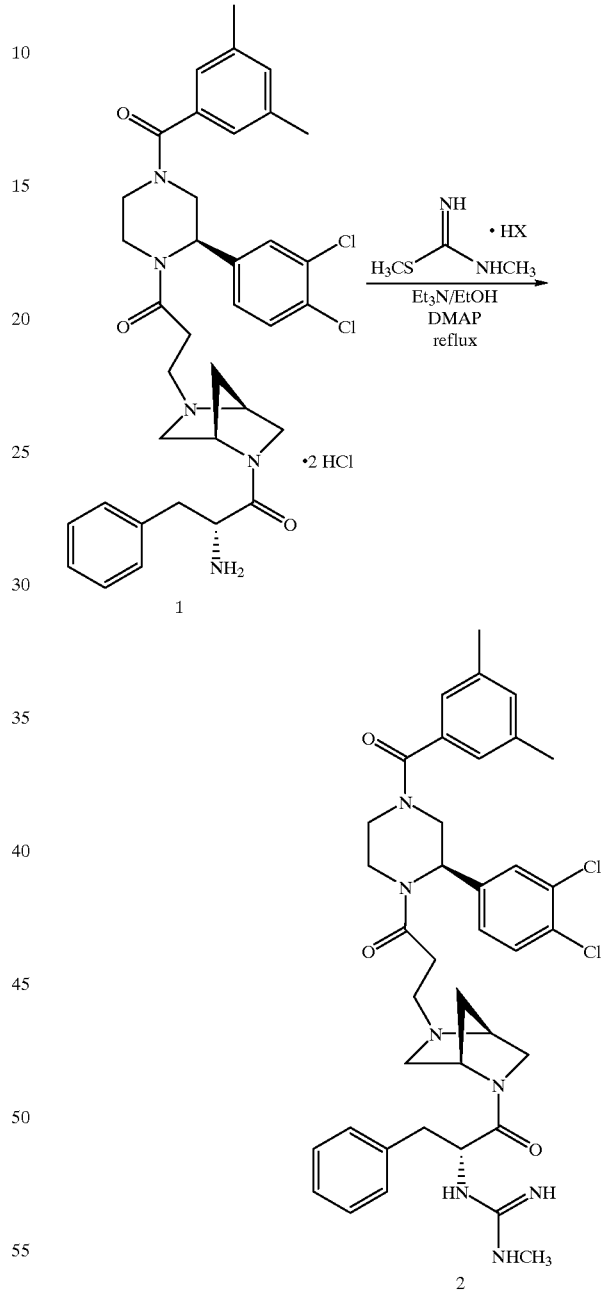

To a solution of compound 1 (from Example 20) (200 mg, 0.301 mmol) in absolute ethanol (EtOH) (2 mL) were added 1,2-dimethyl-2-thiopseudourea hydroiodide (77 mg, 0.33 mmol), Et$_3$N (126 μl, 0.9 mmol) and N,N-dimethylpyridine (5 mg). The mixture was refluxed for 7 days. After reaction was complete, EtOH was evaporated and the residue was diluted with CH$_2$Cl$_2$ and washed with brine (30 mL, 3×), dried (MgSO$_4$), filtered and evaporated to dryness. Crude material was purified by flash chromatography on silica gel, eluting with 9% (1:9) [NH$_4$OH:CH$_3$OH]/91% CH$_2$Cl$_2$. The title compound was obtained as a light yellow solid, M.P. 74–78° C.; FABMS $^{35}$Cl [M+1]$^+$690.2.

EXAMPLE 38

5-[3-[2(R)-(3,4-dichlorophenyl)-4-(3,5-dimethylbenzoyl)-1-piperazinyl]-3-oxopropyl]-2-(2(R)-hydroxy-1-oxo-3-phenylpropyl)-1(S),4(S)-2,5-diazabicyclo-[2.2.1]heptane (Enantiomer B)

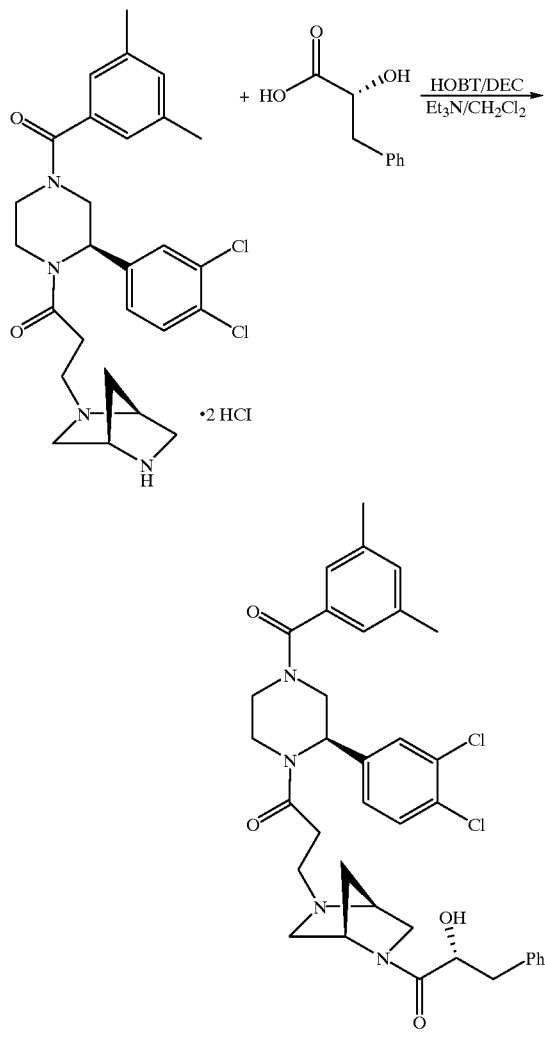

EXAMPLE 39

5-[3-[2(R)-(3,4-dichlorophenyl)-4-(3,5-dimethylbenzoyl)-1-piperazinyl]-3-oxopropyl]-2-(2(S)-hydroxy-1-oxo-3-phenylpropyl)-1(S),4(S)-2,5-diazabicyclo-[2.2.1]heptane (Enantiomer B)

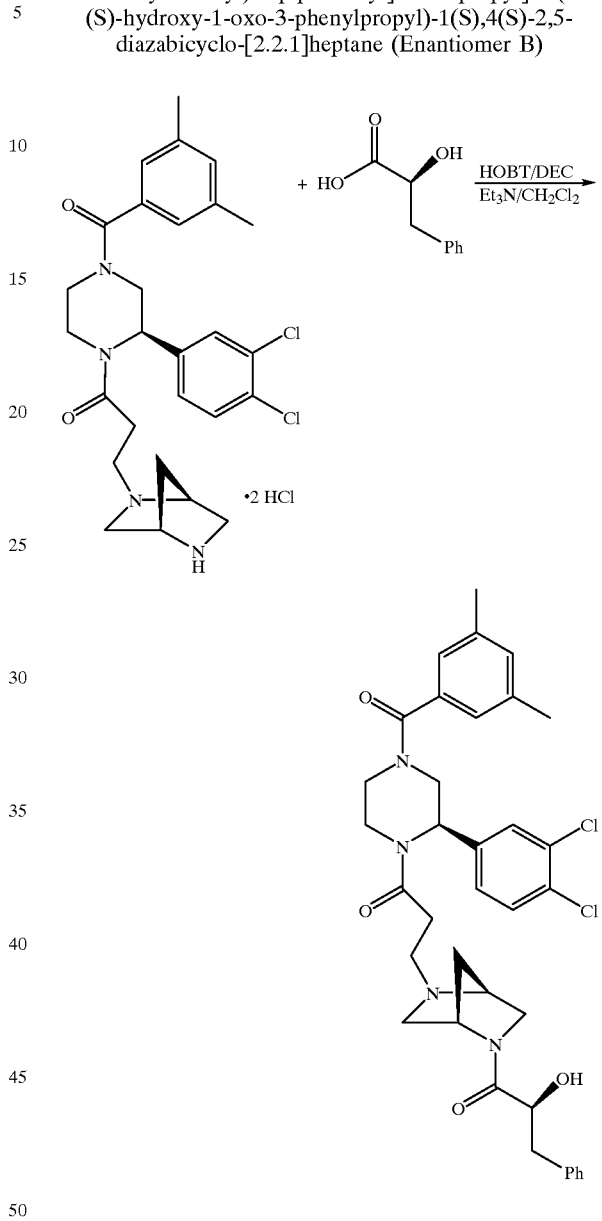

By an analogous method to that described in Example 17, using D-(+)-3-phenyllactic acid in place of N-t-BOC-D-phenylalanine, the title compound was obtained as a white solid, m.p. 90–95° C.; FAB MS $^{35}$Cl [M+1]$^+$ 663.

By an analogous method to that described in Example 17, using L-(−)-3-phenyllactic acid in place of N-t-BOC-D-phenylalanine, the title compound was obtained as a white solid, m.p. 100–105° C.; FAB MS $^{35}$Cl [M+1]$^+$663.

EXAMPLE 40

2-[2(S)-(Cyanomethoxy)-1-oxo-3-phenylpropyl]-5-[3-[2(R)-(3,4-dichlorophenyl)-4-(3,5-dimethylbenzoyl)-1-piperazinyl]-3-oxopropyl]-1(S),4(S)-2,5-diazabicyclo-[2.2.1]heptane (Enantiomer B)

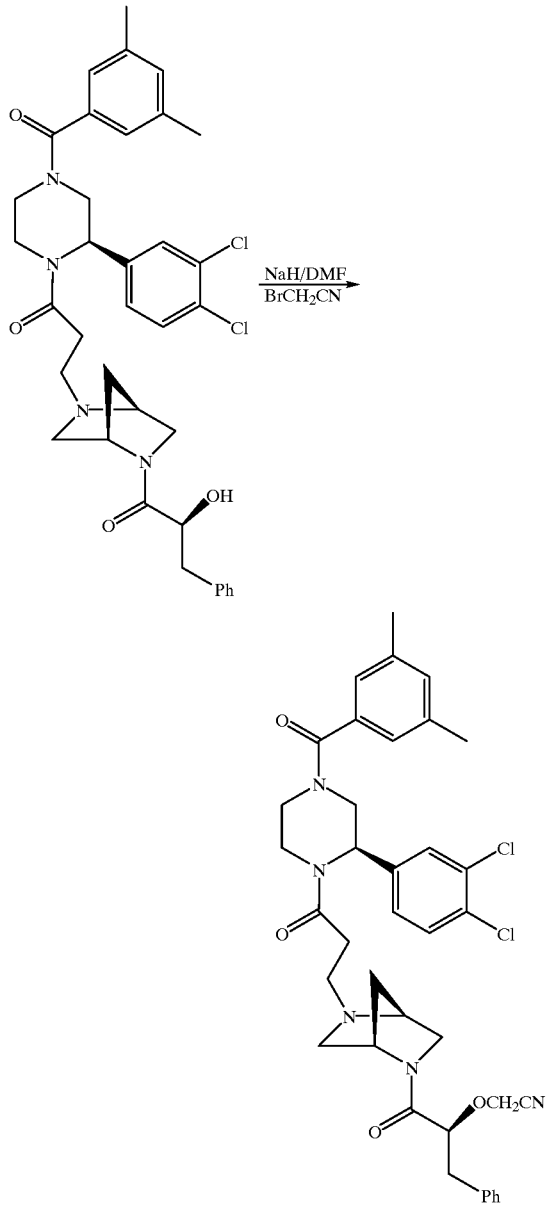

To a solution of the product of Example 39 (129 mg, 0.195 mmol) in dry DMF (1.0 mL) at 0° C. was added 60% NaH (8.6 mg, 0.211 m mol). After stirring at 0° C. for 20 min, bromoacetonitrile (15 mL, 0.211 mmol) was added. After stirring at RT for 2 h, the reaction was quenched with water (2 mL). The mixture was diluted with EtOAc (200 mL) and extracted with brine (50 mL, 3×), dried (MgSO$_4$), filtered and evaporated to give a yellow solid. The crude product was purified by flash chromatography on silica gel, eluting with 6% (1:9) [NH$_4$OH—CH$_3$OH]/94% CH$_2$Cl$_2$ to afford the title compound as a white solid, m.p.70–73° C.; FAB MS [M+1]$^{+35}$Cl 702.

EXAMPLE 41

2-[2(R)-(Cyanomethoxy)-1-oxo-3-phenylpropyl]-5-[3-[2(R)-(3,4-dichlorophenyl)-4-(3,5-dimethylbenzoyl)-1-piperazinyl]-3-oxopropyl]-1(S),4(S)-2,5-diazabicyclo-[2.2.1]heptane (Enantiomer B)

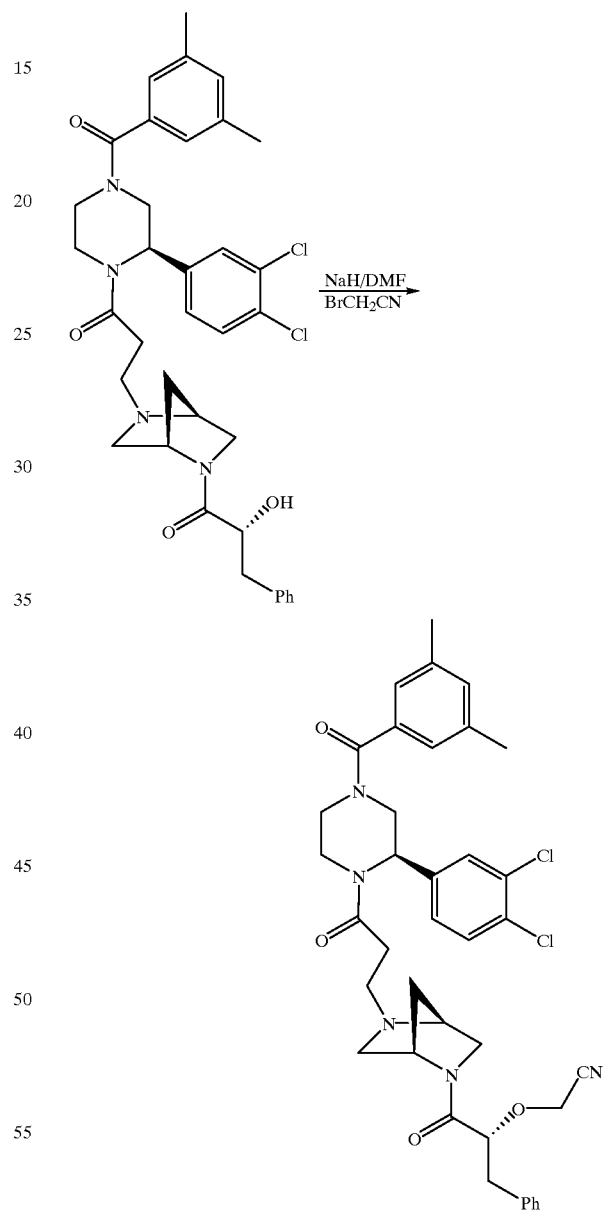

By an analogous method to that described in Example 40, using compound from Example 38 in place the compound from Example 39, the title compound was obtained as a light yellow solid, m.p. 50–53° C.; FAB MS $^{35}$Cl [M+1]$^+$663.

EXAMPLE 42

2-[2(R)-2-(Aminohydroxyimino)ethoyl]-1-oxo-3-phenylpropyl]-5-[3-[2(R)-(3,4-dichlorophenyl)-4-(3,5-dimethylbenzoyl)-1-piperazinyl]-3-oxopropyl]-1(S),4(S)-2,5-diazabicyclo[2.2.1]heptane

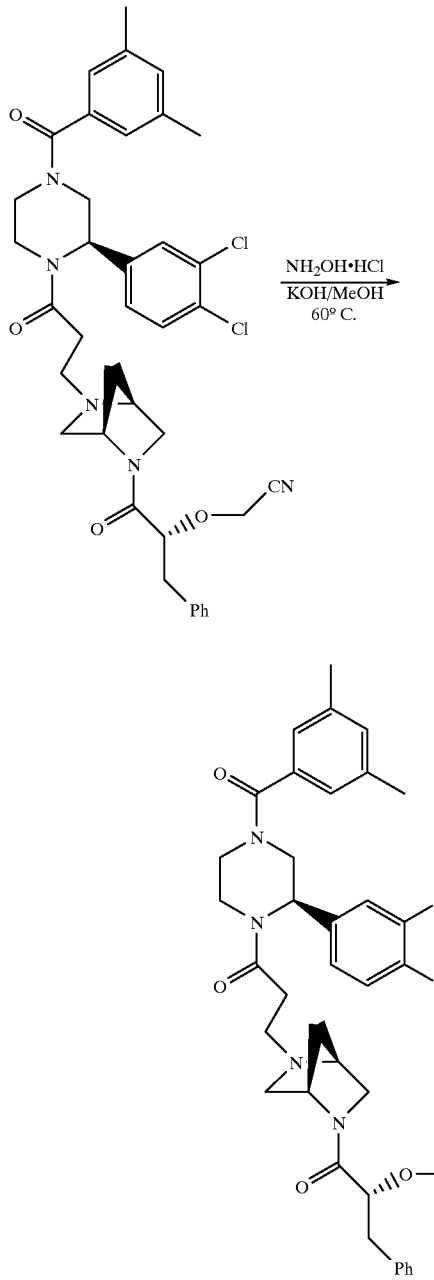

To a solution of the product of Example 41 (98.0 mg, 0.113 mmol) in absolute EtOH (3.5 mL) was added 1N KOH—CH₃OH (0.566 mL, 0.569 mmol) and followed by the addition of H₂NOH.HCl (39.2 mg, 0.569 mmol). The mixture was heated at 60° C. for 4 hours under N₂. After cooling, solvents were evaporated and the residue was redissolved in CH₂Cl₂ (100 mL), washed with saturated NaHCO₃ (30 mL, 2×), dried (MgSO₄), filtered and evaporated to dryness. The crude material was purified by flash chromatography on silica gel, eluting with 5% (1:9) [NH₄OH—CH₃OH]/95% CH₂Cl₂ to afford the title compound (40 mg, 0.054 mmol, 48% yield) as a white solid, m.p. 100–105° C.; FAB MS [M+1]⁺³⁵Cl 735.

EXAMPLE 43

[1 (R)-[[5-[3-[2(R)-(3,4-dichlorophenyl)-4-(3,5-dimethylbenzoyl)-1-piperazinyl]-3-oxopropyl]-1(S),4(S)-2,5-diazabicyclo[2.2.1]heptan-2-yl]carbonyl]-2-phenylethyl]methylcarbamate (enantiomer B)

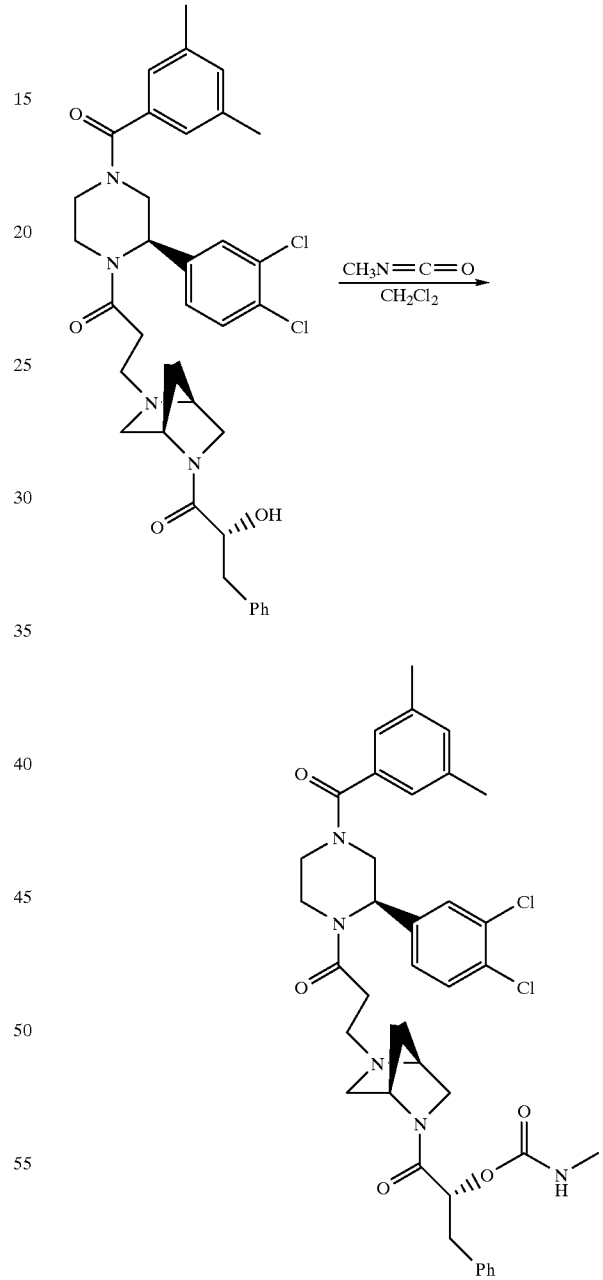

To a solution of the product of Example 38 (100 mg, 0.15 mmol) in CH₂Cl₂ (2 mL) were added methylisocyanate (12.5 μL, 0.21 mmol) and N,N-dimethylaminopyridine (4.5 mg, 0.037 mmol). The mixture was stirred at RT for a few days. After the reaction was complete, solvent was evaporated and the residue purified by flash chromatography on silica gel, eluting with 5% (1:9) [NH$_4$OH—CH$_3$OH]/95% CH$_2$Cl$_2$ to give the title compound (85 mg, 0.118 mmol, 79%) as a white solid, 60–62° C.; FAB MS[M+1]$^{+35}$Cl 720.

EXAMPLE 44

[1(S)-[[5-[3-[2(R)-(3,4-dichlorophenyl)-4-(3,5-dimethylbenzoyl)-1-piperazinyl]-3-oxopropyl]-1(S),4(S)-2,5-diazabicyclo[2.2.1]heptan-2-yl]carbonyl]-2-phenylethyl]methylcarbamate (enantiomer B)

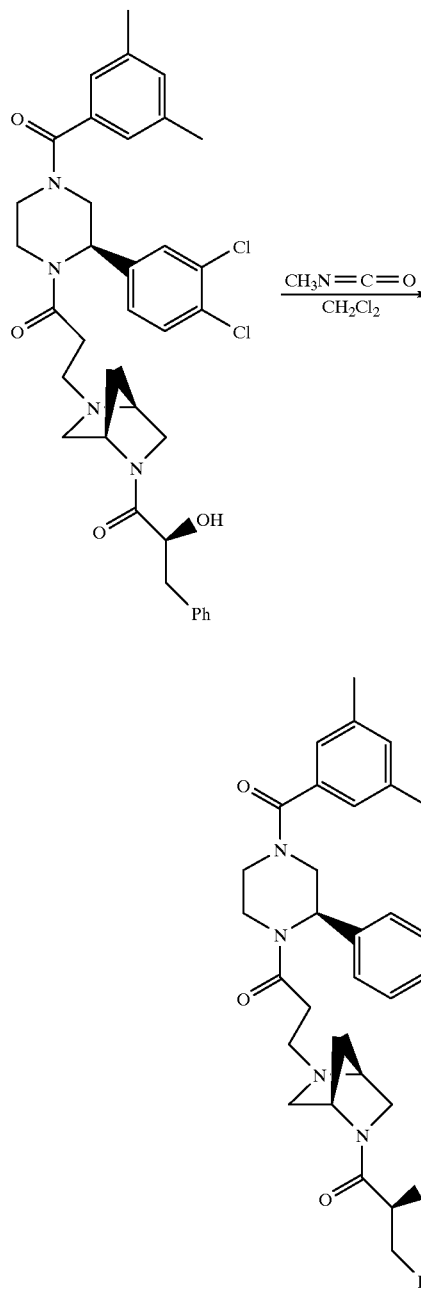

By an analogous method to that described for Example 43, using compound from Example 39 in place of compound from Example 38, the title compound was obtained as a white solid in 42% yield after purification by silica gel chromatography, m.p. 87–90° C.; HRMS [M+1]$^+$35Cl, calculated for C$_{38}$H$_{44}$N$_5$O$_5$Cl$_2$ 720.2720; found, 720.2716.

EXAMPLE 45

2-[2(S)-Methoxy-1-oxo-3-phenylpropyl]-5-[3-[2(R)-(3,4-dichlorophenyl)-4-(3,5-dimethylbenzoyl)-1-piperazinyl]-3-oxopropyl]-1(S),4(S)-2,5-diazabicyclo-[2.2.1]heptane (Enantiomer B)

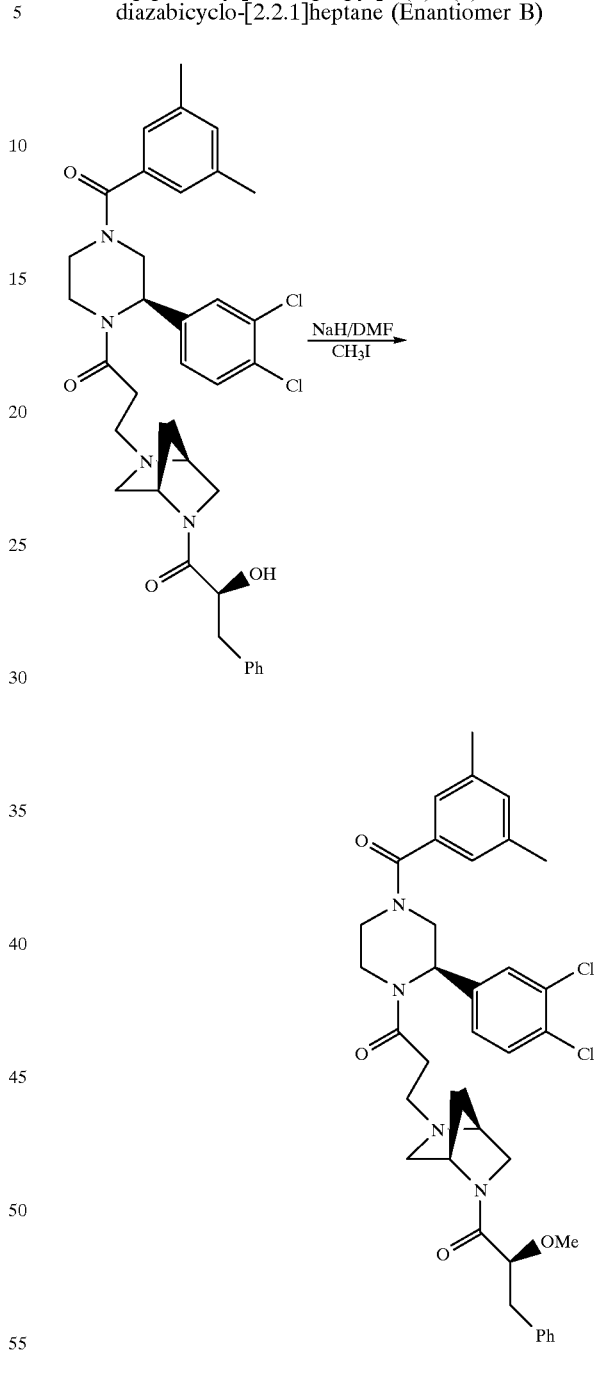

To a solution of the product of Example 39 (100 mg, 0.15 mmol) in DMF (1 mL) at 0° C. was added 60% NaH in mineral oil (7.2 mg, 0.18 mmol). After stirring at 0° C. for 20 minutes, CH$_3$I (11 μL, 0.18 mmol) was added and stirring was continued at 0° C. for 30 min. The reaction was diluted with EtOAc (100 mL) and washed with brine (30 mL, 2×), dried(MgSO$_4$), filtered and evaporated to give a solid. Product was purified by flash chromatography on silica gel, eluting with 6%(1:9) [NH$_4$OH—CH$_3$OH]/95% CH$_2$Cl$_2$. M.p. 102–104° C.; HRMS [M+1]$^{+35}$Cl, calculated for C$_{37}$H$_{43}$N$_4$O$_4$Cl$_2$ 677.2661; found, 677.2662.

EXAMPLE 46

(1R,4R)-1,1-Dimethylethyl 5-hydroxy-2-azabicyclo[2.2.1]heptane-2-carboxylate (5) and (1S,4S)-1,1-dimethylethyl 5-hydroxy-2-azabicyclo[2.2.1]heptane-2-carboxylate (7)

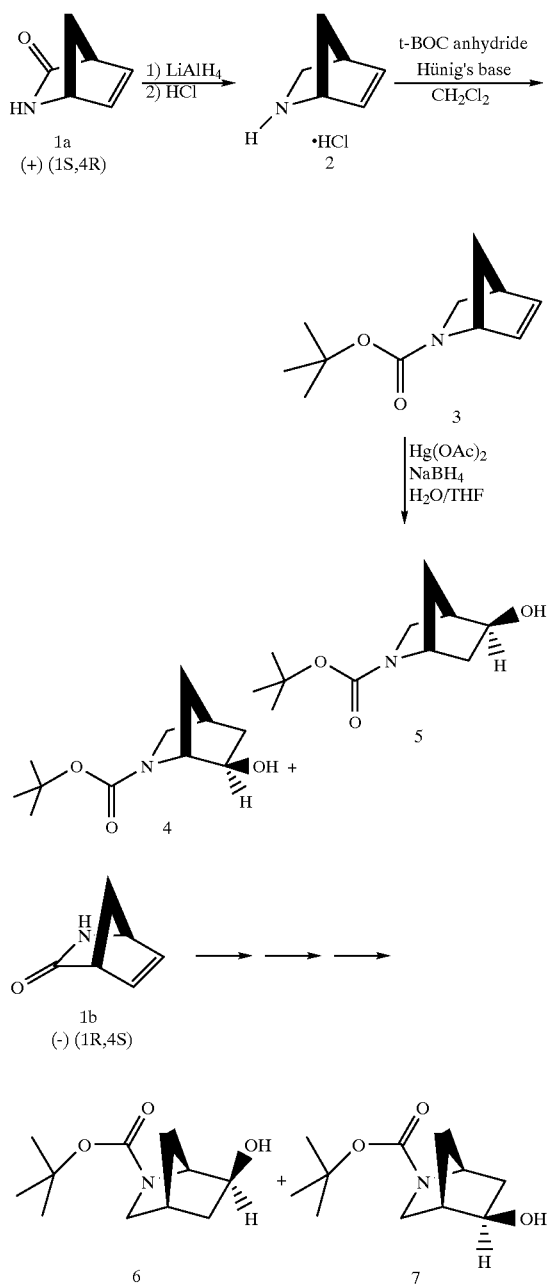

Preparation of compounds (5) and (7) have been described in Example 6 (steps 1, 2 and 3) except for using the chiral (1S,4R) or (1R,4S)-2-azabicyclo[2.2.1]hept-5-en-3-one (1a) or (1b) as starting materials.

EXAMPLE 47

(Exo)-1,1-dimethylethyl 5-[2-[2(R)-(3,4-dichlorophenyl)-4-(3,5-dimethylbenzoyl)-1-piperazinyl]-2-oxoethoxy]-1-(R),4(R)-2-azabicyclo[2.2.1]heptane-2-carboxylate (enantiomer B)

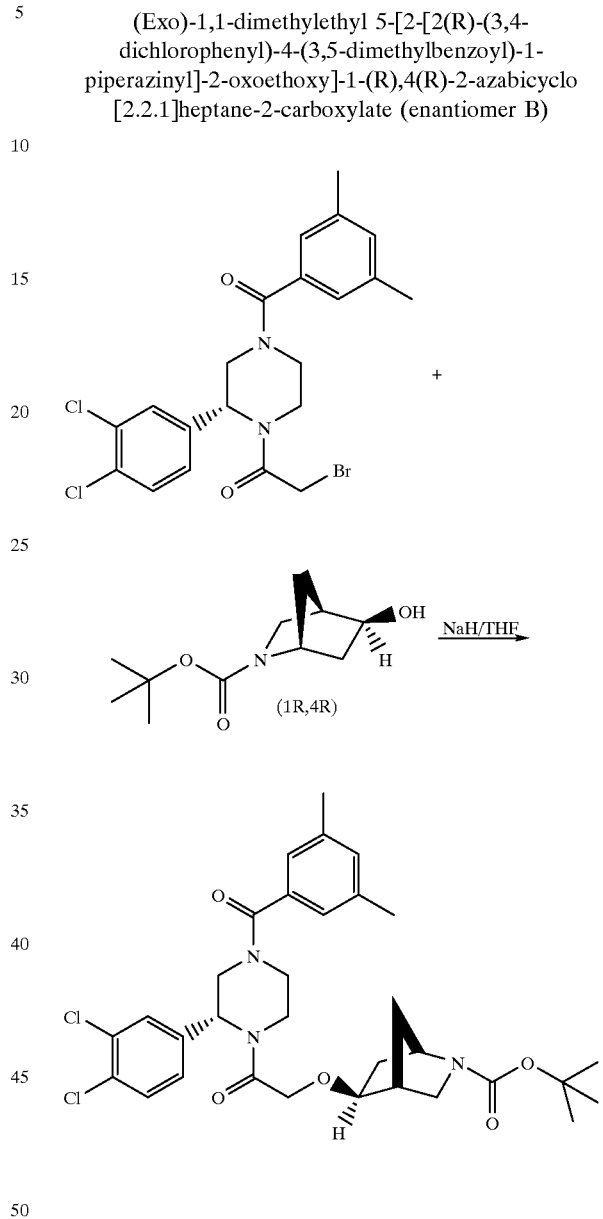

To a solution of compound (5) from Example 46 (1.1 g, 5.2 mmol) in THF (20 mL) was added 60% NaH in mineral oil (0.23 g, 5.7 mmol). The mixture was stirred at RT for 2 hours and a solution of bromo intermediate (from Example 5) in THF (5 mL) was added dropwise under nitrogen. After stirring at RT overnight, the reaction was quenched with saturated $NH_4Cl$ (100 mL) and extracted with $CH_2Cl_2$ (70 mL, 3×), dried ($Na_2SO_4$), filtered and concentrated under vacuum to give a light brown oil (3.8 g). The crude product was separated by flash chromatography on silica gel (150 g), eluting with 2.5% (1:9) [$NH_4OH/CH_3OH$]/97.5% $CH_2Cl_2$ to give the title compound (2.6 g) as a light yellow solid, m.p. 91–93° C., FAB MS [M+1]$^{+35}$Cl 616, HRMS Cal'd for $C_{32}H_{40}N_3O_5Cl_2$ [M+1]$^{+35}$Cl 616.2345; found, 616.2340.

EXAMPLE 48

2(R)-(3,4-Dichlorophenyl)-4-(3,5-dimethylbenzoyl)-1-[[[exo-1(R),4(R)-2-azabicyclo[2.2.1]heptan-5-yl]oxy]acetyl]piperazine (enantiomer B) hydrochloride salt

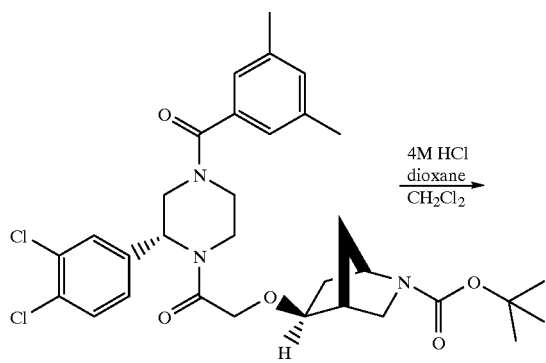

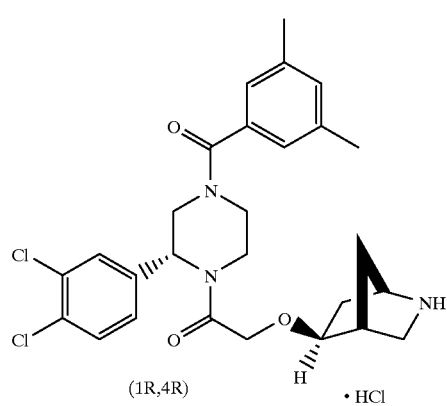

To a solution of the product of Example 47 (2.5 g, 4.05 mmol) in CH$_2$Cl$_2$ (3 mL) was added 4M HCl/dioxane (10 mL). After stirring at RT for 1 h, the reaction mixture was evaporated to give the title compound (HCl salt) as a light yellow solid (2.2 g, 4.05 mmol), FAB MS [M+1] $^{35}$Cl 516.

EXAMPLE 49

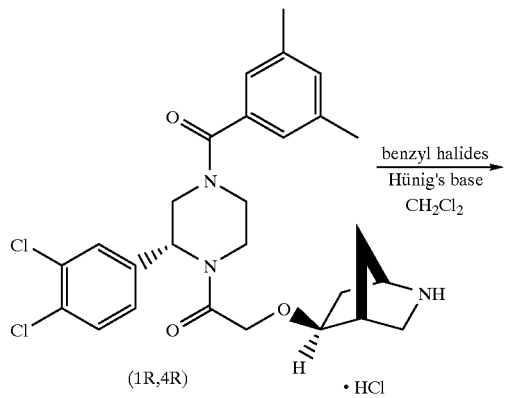

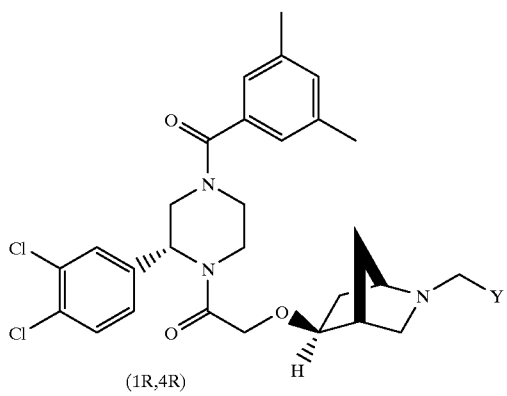

By an analogous method to that described in Example 9, using the compound from Example 48, and benzyl bromide or substituted benzyl chloride, the following compounds were prepared as solids.

| Y | m.p. ° C. | Cal'd MS | High Res MS [M + 1]Cl$^{35}$ |
|---|---|---|---|
| phenyl | 67–69 | 606.2290 | 606.2298 |
| 4-(NHCOCH$_3$)phenyl | 114–116 | 663.2505 | 663.2502 |
| 4-(CONHCH$_3$)phenyl | 107–109 | 663.2505 | 663.2496 |

EXAMPLE 50

2(R)-(3,4-Dichlorophenyl)-4-(3,5-dimethylbenzoyl)-
1-[[[exo-2-(3-thienylmethyl)-1(S),4(S)-2-azabicyclo
[2.2.1]heptan-5-yl)oxy]acetyl]piperazine
(enantiomer B)

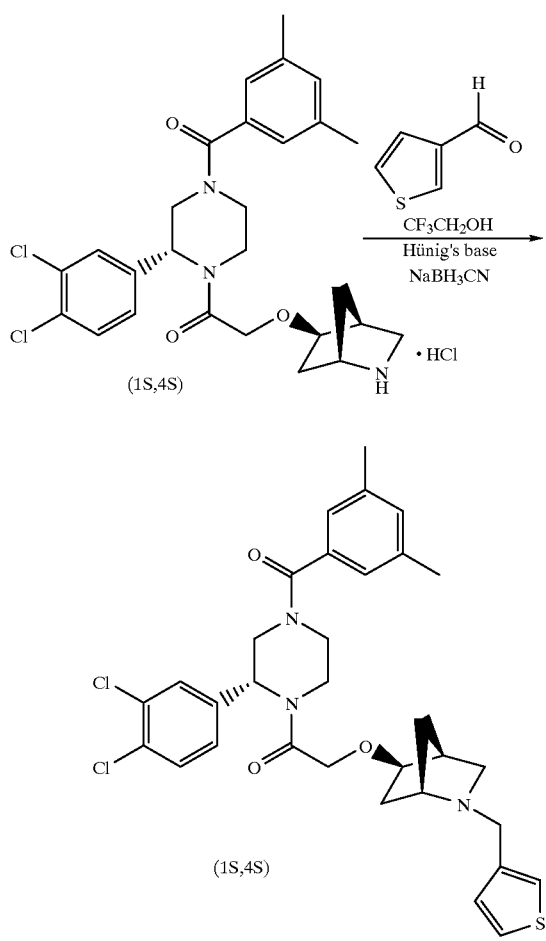

The chiral (1S,4S) analog [2(R)-(3,4-dichlorophenyl)-4-(3,5-dimethylbenzoyl)-1-[[[exo-1(S),4(S)-2-azabicyclo[2.2.1]heptan-5-yl]oxy]acetyl]piperazine (enantiomer B) hydrochloride salt] was prepared by analogous methods to those described in Examples 47 and 48, using compound (7) from Example 46. To a solution of this (1S,4S) compound (0.17 g, 0.3 mmol) in CF$_3$CH$_2$OH (3 mL) were added Hünig's base (35 mg) and 3-thiophenecarboxaldehyde (50 mg, 0.45 mmol). After stirring at RT for 2 h, NaBH3CN (37 mg, 0.6 mmol) was added. The reaction was continued stirring for 2 h at RT then quenched with saturated NaHCO$_3$ (30 mL) and extracted with CH$_2$Cl$_2$ (30 mL, 2×). The combined CH$_2$Cl$_2$ extracts were dried (Na$_2$SO$_4$), filtered and evaporated to give a crude gummy solid (0.17 g). After purification by flash chromatography on silica gel (30 g), eluting with 3% (1:9) [NH$_4$OH/CH$_3$OH]/97% CH$_2$Cl$_2$, the title compound was obtained as an off white solid, m.p. 72–74° C., HR MS $^{35}$Cl (M+1)$^+$ cal'd for C$_{32}$H$_{36}$N$_3$O$_3$Cl$_2$S 612.1854; found, 612.2502.

EXAMPLE 51

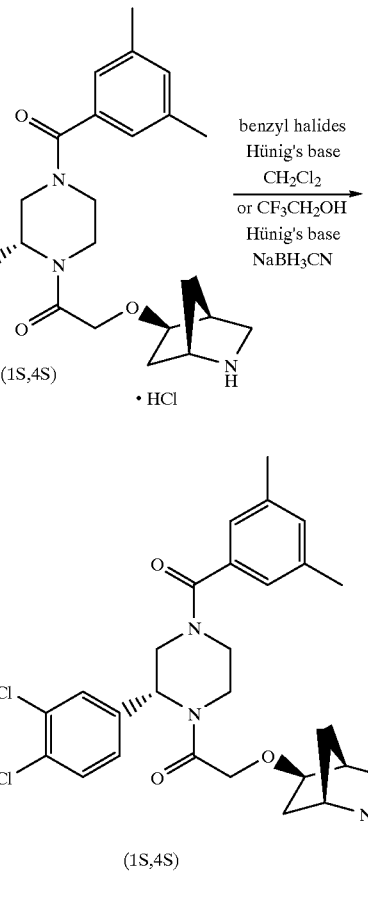

By employing analogous methods to those described in Examples 9, 49 or 50, but using chiral (1S,4S) HCl salt in place of (1R,4R) HCl salt from Example 48, the following compounds were obtained as solids. All of the compounds were purified by flash chromatography on silica gel.

| Y | m.p. ° C. | Cal'd MS | High Res MS [M + 1]Cl$^{35}$ |
|---|---|---|---|
| (benzyl) | 70–72 | 606.2290 | 606.2288 |
| (4-acetamidophenyl) | 116–118 | 663.2505 | 663.2502 |

117
-continued

| Y | m.p. °C. | Cal'd MS | High Res MS [M + 1]Cl$^{35}$ |
|---|---|---|---|
| (3,5-dimethylisoxazolyl) | 71–73 | 625.2348 | 625.2357 |
| (2-thienyl) | 72–74 | 612.1854 | 612.1862 |

EXAMPLE 52

1,1-Dimethylethyl 3-exo-hydroxy-8-azabicyclo[3.2.1]octane-8-carboxylate (3) and 1,1-dimethylethyl 3-endo-hydroxy-8-azabicyclo[3.2.1]octane-8-carboxylate (4)

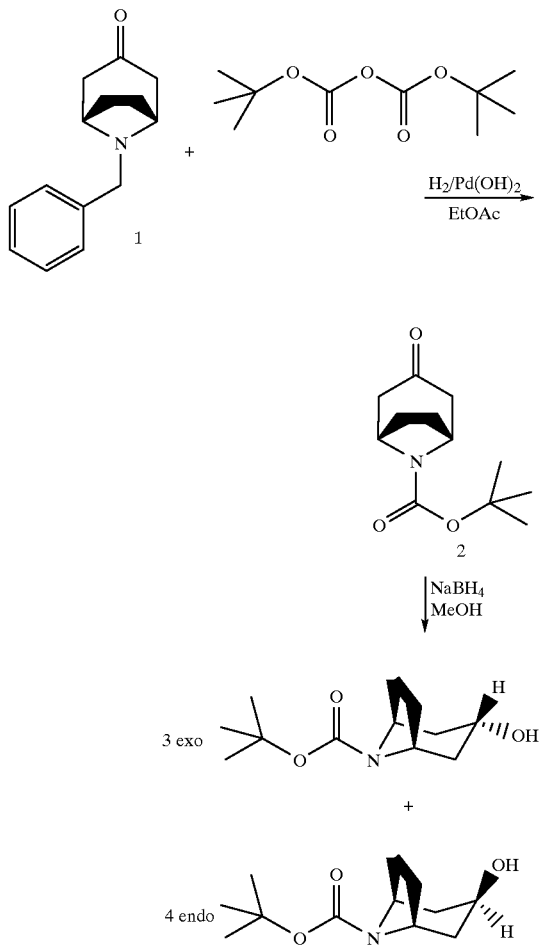

To a solution of N-benzyl-3-oxo-8-azabicyclo[3.2.1]-octane (20 g, 93 mmol) in EtOAc (220 mL) were added t-BOC anhydride (24.2 g, 112 mmol) and 20% Pd(OH)$_2$/C (4 g). The mixture was hydrogenolyzed at 38.5 psi. After the reaction was complete, catalyst was filtered and filtrate was evaporated to give a solid crude product (21 g). The crude

118 material (19 g, 84 mmol) was dissolved in CH$_3$OH (100 mL) and NaBH$_4$ (4.8 g, 127 mmol) was added portion wise at 0° C. The reaction was stirred at 0° C. and gradually warmed to RT. After 3 h, the reaction was quenched with acetic acid (8 mL) and CH$_3$OH was evaporated. The residue was redissolved in CH$_2$Cl$_2$ (300 mL) and washed with saturated NaHCO$_3$ solution, dried (Na$_2$SO$_4$), filtered and evaporated to give a solid. The crude material was purified by flash chromatography (400 g silica gel), eluting with 25% EtOAc/hexane to give exo compound 3 (9.8 g, 43.1 mmol, 51.4%) and endo compound 4 (5 g, 22 mmol, 26.2%) as white solids.

EXAMPLE 53

(Exo)-1,1-dimethylethyl 3-[2-[2(R)-(3,4-dichlorophenyl)-4-(3,5-dimethylbenzoyl)-1-piperazinyl]-2-oxoethoxy]-8-aza[3.2.1]octane-8-carboxylate (enantiomer B)

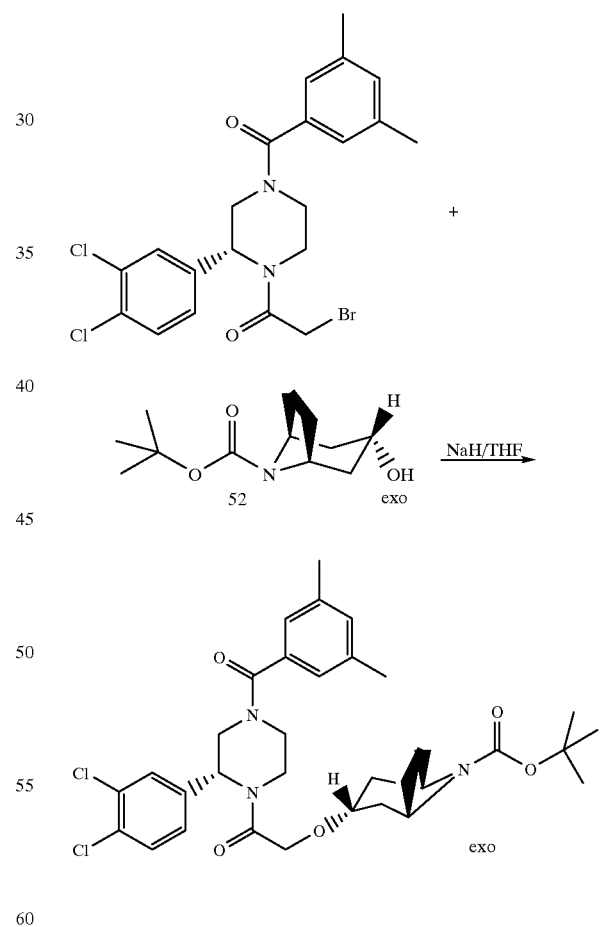

By an analogous method to that described in Example 47, but using compound (3) from Example 52 in place of compound (5) from Example (46), the title compound was obtained as a white foam after flash chromatography on silica gel, m.p. 85–87° C., FAB MS $^{35}$Cl [M+1]$^+$ 630.

EXAMPLE 54

2(R)-(3,4-Dichlorophenyl)-4-(3,5-dimethylbenzoyl)-1-[[[exo-8-aza-[3.2.1]octan-3-yl]oxy]acetyl] piperazine (enantiomer B) hydrochloride salt

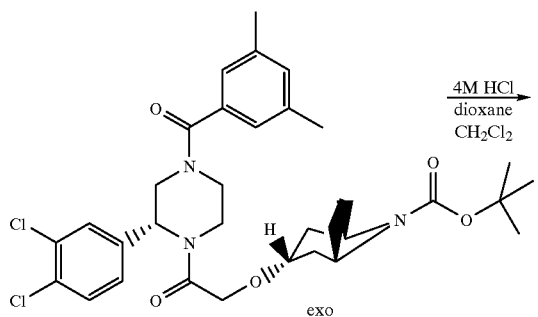

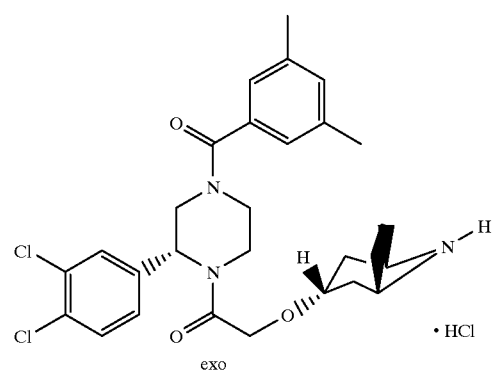

By an analogous method to that described in Example 48, but using compound from Example 53 in place of the product of Example 47, the title compound was obtained as a white foam hydrochloride salt, FAB MS $^{35}$Cl [M+1]$^+$530.

EXAMPLE 55

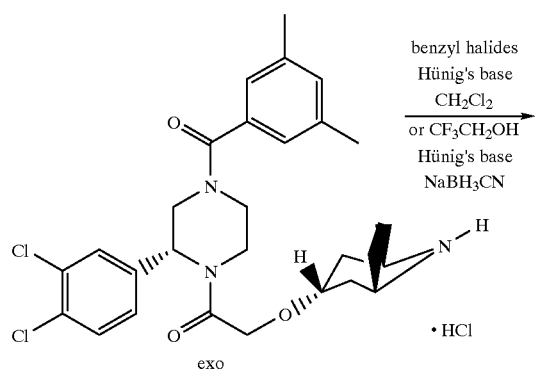

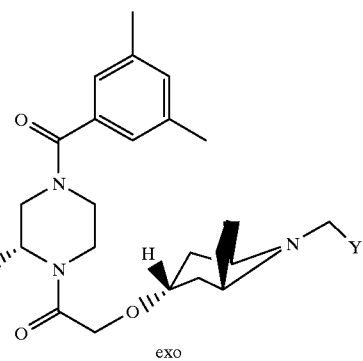

By using methods analogous to those described in Examples 9, 49 or 50 but using the product of Example 54 in place of the product of Example 48, the following compounds were obtained. All compounds listed below were purified by flash chromatography on silica gel.

| Y | m.p. ° C. | Cal'd MS | High Res MS [M + 1]Cl$^{35}$ |
|---|---|---|---|
| phenyl | 79–81 | 620.2447 | 620.2439 |
| 4-acetamidophenyl | 115–117 | 677.2661 | 677.2648 |
| thiophene | 75–77 | 626.2011 | 626.2008 |
| 3,5-dimethylisoxazole | 78–80 | 639.2505 | 639.2500 |
| 4-(N-methylcarbamoyl)phenyl | 115–117 | 677.2661 | 677.2676 |

EXAMPLE 56

(Endo)-1,1-dimethylethyl 3-[2-[2(R)-(3,4-dichlorophenyl)-4-(3,5-dimethylbenzoyl)-1-piperazinyl]-2-oxoethoxy]-8-aza[3.2.1]octane-8-carboxylate (enantiomer B)

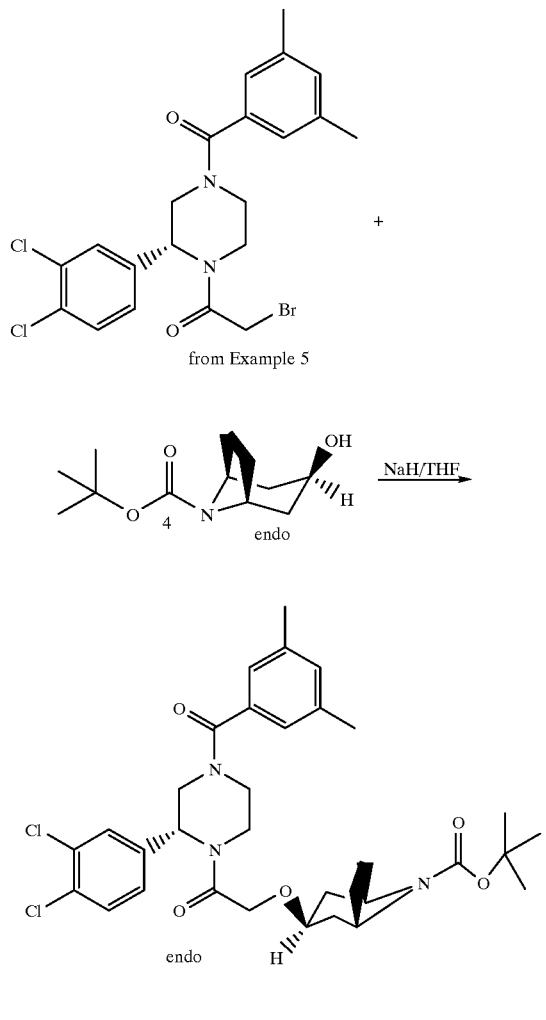

By analogous methods to those described in Examples 47 and 53, using endo compound (4) (Example 52) in place of exo compound (3) (Example 52), the title compound was prepared as a solid by flash chromatography purification on silica gel, m.p. 85–87° C., FAB MS [M+1]⁺35Cl 630.

EXAMPLE 57

2(R)-(3,4-Dichlorophenyl)-4-(3,5-dimethylbenzoyl)-1-[[[endo-8-aza-[3.2.1]octan-3-yl]oxy]acetyl] piperazine (enantiomer B) hydrochloride salt

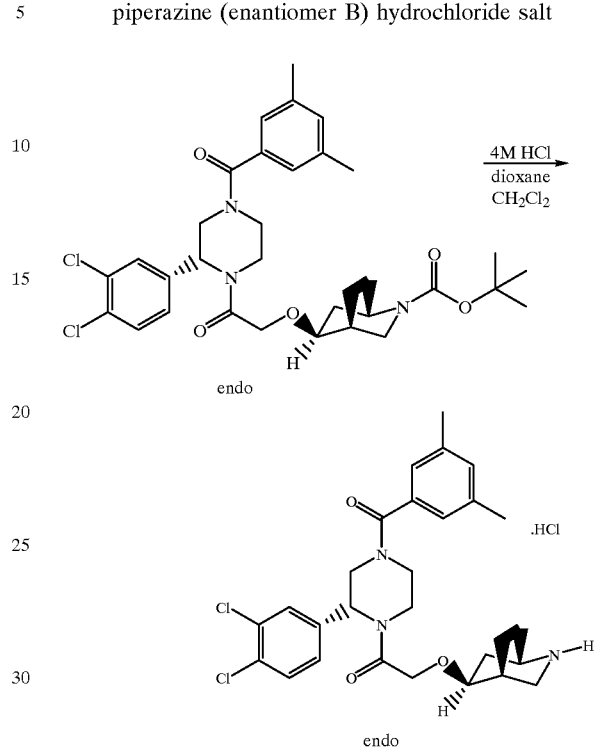

By an analogous method to that of Example 48, using endo compound prepared in Example 56 in place of exo compound (Example 47), the title compound was prepared as a solid, FAB MS [M+1]⁺35Cl 530.

EXAMPLE 58

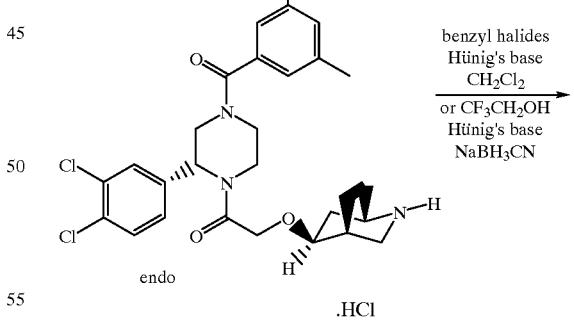

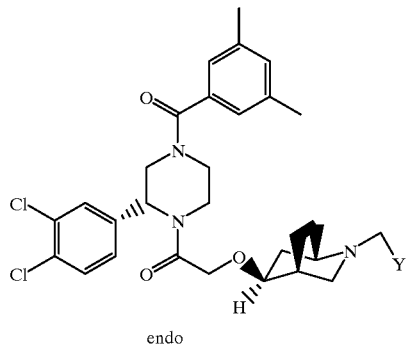

endo

By analogous methods to those described in Examples 9, 49 and 50, using endo compound prepared in Example 57 in place of exo compound (Example 54), the following compounds were prepared as solids and purified by flash chromatography on silica gel.

| Y | m.p. ° C. | Cal'd MS | High Res MS [M + 1]Cl$^{35}$ |
|---|---|---|---|
|  | 79–81 | 620.2447 | 620.2439 |
| 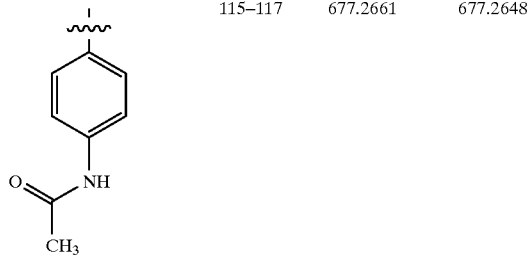 | 115–117 | 677.2661 | 677.2648 |
| 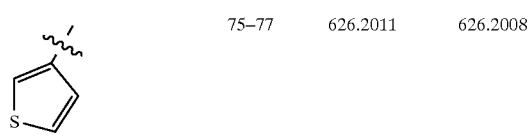 | 75–77 | 626.2011 | 626.2008 |
|  | 78–80 | 639.2505 | 639.2500 |

| Y | m.p. ° C. | Cal'd MS | High Res MS [M + 1]Cl$^{35}$ |
|---|---|---|---|
| 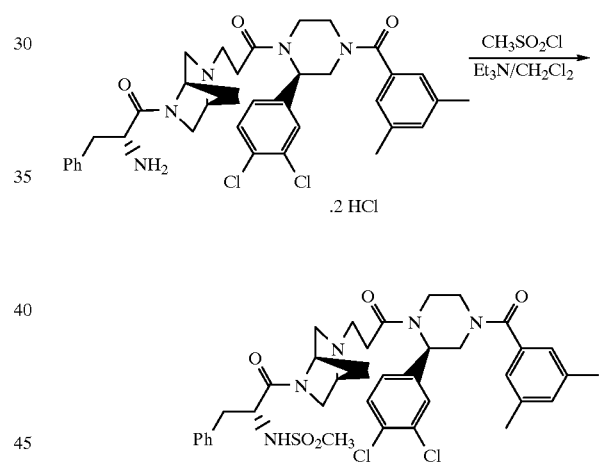 | 115–117 | 677.2661 | 677.2676 |

EXAMPLE 59

N-1(R)-[[5-[3-[2(R)-(3,4-Dichlorophenyl)-4-(3,5-dimethylbenzoyl)-1-piperazinyl]-3-oxopropyl]-1(S), 4(S)-2,5-diazabicyclo[2.2.1]heptan-2-yl]carbonyl]-2-phenylethyl]methylsulfonamide (enantiomer B)

To a solution of the product of Example 16 (130 mg, 0.176 mmol) in $CH_2Cl_2$ (3.5 mL) was added Hünig's base (0.1 mL, 0.58 mmol) followed by the addition of $CH_3SO_2Cl$ (15 μL, 0.194 mmol). The reaction was stirred at RT for 1.4 h, diluted with $CH_2Cl_2$ (200 mL) and washed with brine (50 mL, 3×), dried ($MgSO_4$), filtered and concentrated to give a solid. Product was purified by flash chromatography on silica gel, eluting with 5% (1:9) [$NH_4OH/CH_3OH$]/95% $CH_2Cl_2$, to obtain the title compound as a white solid, m.p. 110–115° C., HR MS $^{35}$Cl [M+1]$^+$cal'd for $C_{37}H_{44}N_5O_5Cl_2S$ 740.2440; found, 740.2443

EXAMPLE 60

2-[2(R)-(Cyanomethylamino)-1-oxo-3-phenylpropyl]-5-[3-[2-(R)-(3,4-dichlorophenyl)-4-(3,5-dimethylbenzoyl)-1-piperazinyl]-3-oxopropyl]-1(S),4(S)-2,5-diazabicyclo[2.2.1]heptane

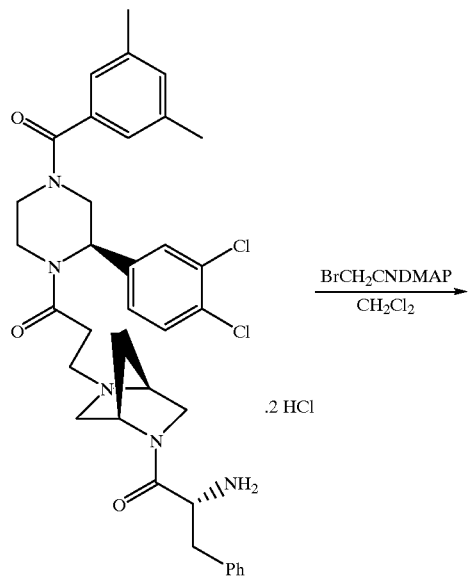

To a solution of the product of Example 16 (300 mg, 0.408 mmol) in THF (6 mL) was added Et₃N (0.199 mL, 1.43 mmol) followed by the addition of BrCH₂CN (30 μL, 0.428 mmol) and 4 Å molecular sieves. The reaction was heated at 60° C. for 4 days. After cooling, the molecular sieves were filtered off and the filtrate was evaporated. The residue was diluted with CH₂Cl₂ (200 mL), washed with brine (50 mL, 3×), dried (MgSO₄), filtered and concentrated to give a solid. Product was purified by flash chromatography on silica gel, eluting with 5% (1:9) [NH₄OH/CH₃OH]/95% CH₂Cl₂, and the title compound was obtained as a light yellow solid, m.p. 87–90° C., FABMS $^{35}$Cl [M+1]$^{+}$701.

EXAMPLE 61

2-[2(R)-[[2-(Aminohydroxyimino)ethyl]amino]-1-oxo-3-phenylpropyl]-5-[3-[2(R)-(3,4-dichlorophenyl)-4-(3,5-dimethylbenzoyl)-1-piperazinyl]-3-oxopropyl]-1(S),4(S)-2,5-diazabicyclo[2.2.1]heptane

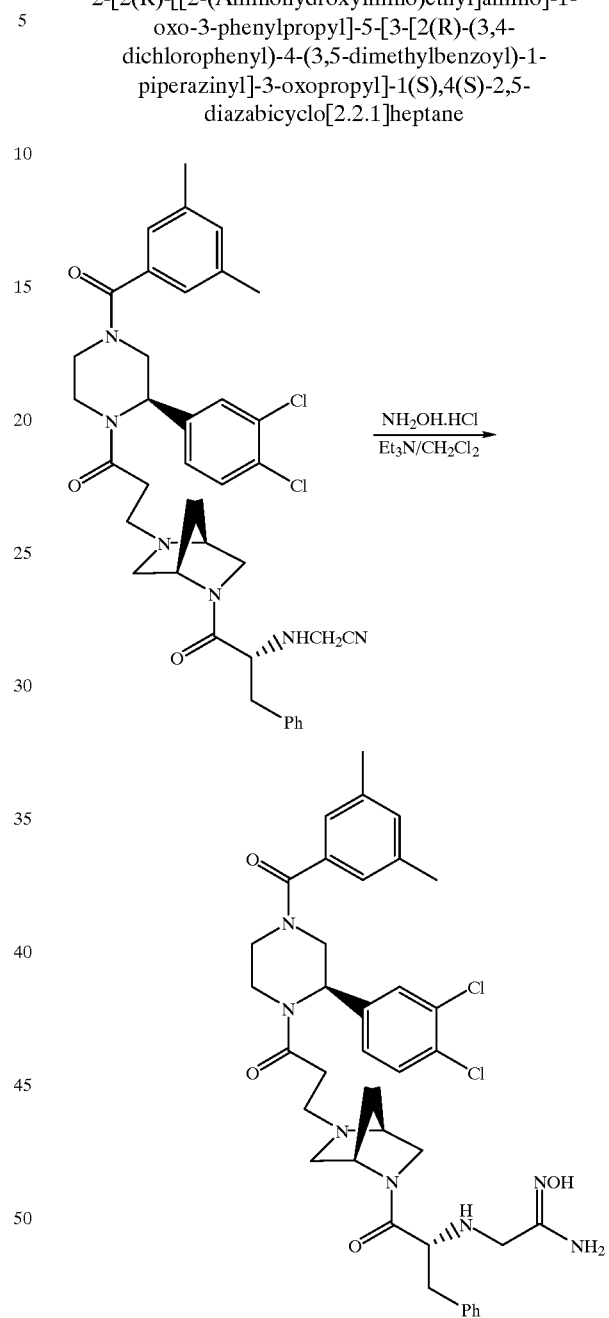

By employing an analogous method to that described for Example 42, using the compound from Example 60 in place of the product of Example 41, the title compound was obtained as a white solid after flash chromatography, m.p. 75–78° C., HR MS $^{35}$Cl [M+1]$^{+}$ cal'd for $C_{38}H_{46}N_7O_4Cl_2$ 734.2988; found, 34.2989.

EXAMPLE 62

(±)-2(R)-(3,4-Dichlorophenyl)-4-(3,5-dimethylbenzoyl)-1-[[[endo-2-[(3,5-dimethyl-4-isoxazoyl)methyl]-2-azabicyclo[2.2.1]heptan-5-yl]amino]-acetyl]piperazine (from enantiomer B)

Step 1

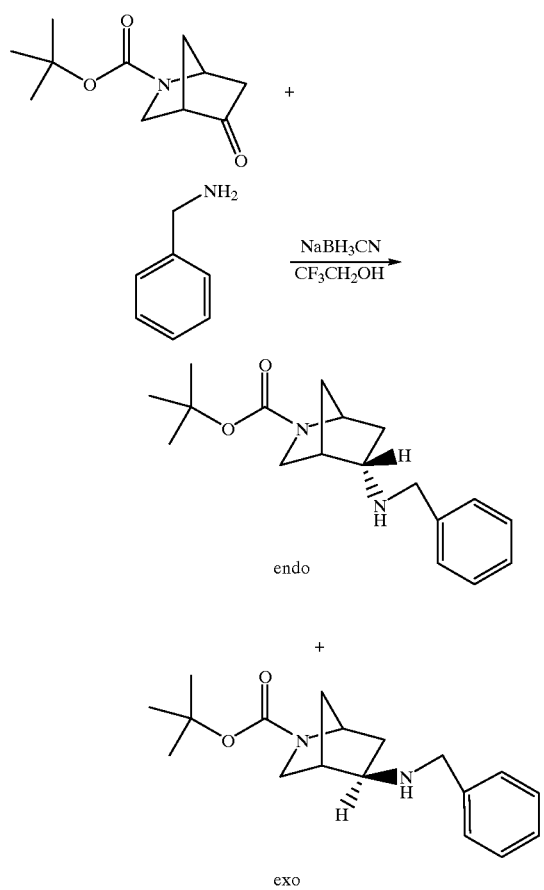

A mixture of compound (D) from Example 6 (3.01 g, 14 mmol), benzyl amine (1.56 mL, 14 mmol), and NaBH₃CN (1.76 g, 24 mmol) in CF₃CH₂OH (16 mL) was stirred at RT overnight under N₂. After reaction was complete, solvent was evaporated and the residue was dissolved in EtOAc (150 mL), washed with saturated NaHCO₃ solution (150 mL, 2×), dried (Na₂SO₄), filtered and evaporated to give the product as a brown oil. Products were purified by flash silica gel chromatography, eluting with 2% NH₃—CH₃OH in CH₂Cl₂ to give endo FABMS ³⁵Cl[M+1] 303.3 and exo products FABMS ³⁵Cl[M+1] 303.3.

Step 2

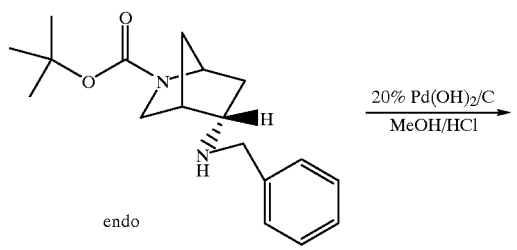

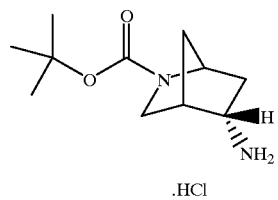

A solution of endo compound from step1 (1.73 g, 5.4 mmol) in CH₃OH (40 mL)was mixed with 0.8M HCl (2 mL, 1.6 mmol) and 20% Pd(OH)₂/C (0.6 g) and hydrogenolyzed at 50 psi for 4 days. After reaction was complete, catalyst was filtered and filtrate was evaporated to give the product as a light green oil (1.2 g) which was used in next step without purification, FABMS ³⁵Cl[M+1] 212.8.

Step 3

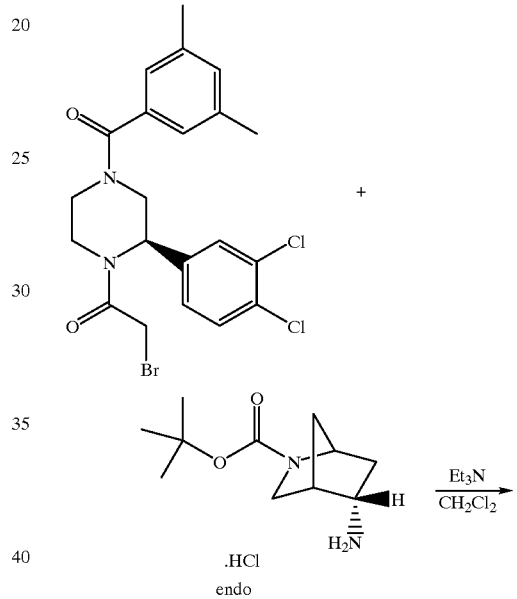

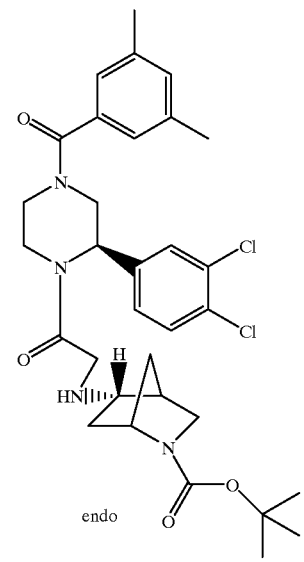

To a solution of bromoacyl derivative from Example 5 (1.94 g, 4 mmol) in CH₂Cl₂ (5 mL) was added the endo compound from step 2 (1.14 g, 5 mmol). The mixture was stirred at RT overnight. After reaction was complete, the mixture was diluted with CH$_2$Cl$_2$ (100 mL), washed with brine (50 mL,4×), dried (Na$_2$SO$_4$), filtered and evaporated to give the product as a brown oil. Product was purified by flash silica gel chromatography, eluting with 3.5% [(1:9) NH$_4$OH—CH$_3$OH]/96.5% CH$_2$Cl$_2$ to give the product as a yellow solid (1.4 g), m.p. 96–98° C.; FABMS $^{35}$Cl[M+1] 615.3.

Step 4

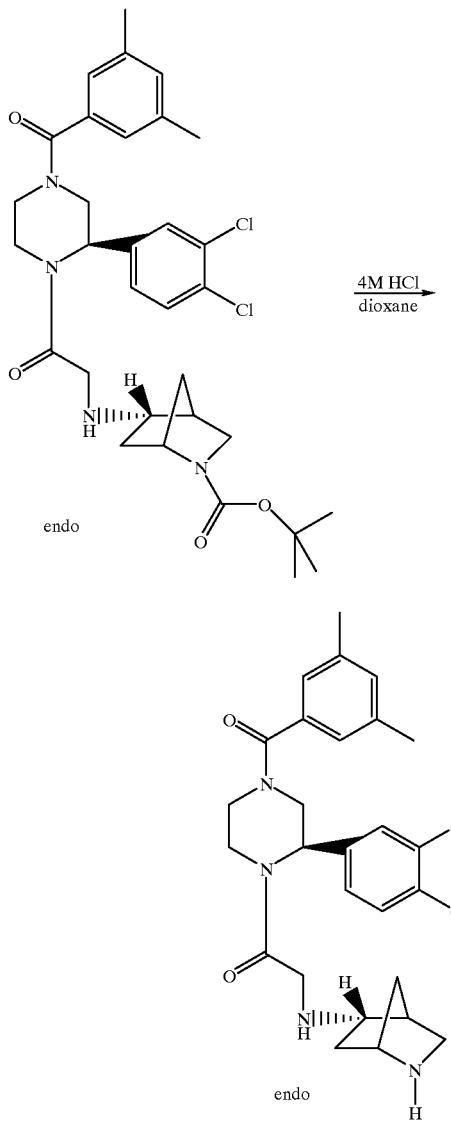

To a solution of the product of step 3 (1.25 g, 2.03 mmol) in CH$_2$Cl$_2$ (2 mL) was added 4M HCl-dioxane solution (6 mL, 24 mmol). The mixture was stirred at RT for 2 h, then excess HCl was evaporated to give a yellow solid (1.2 g), FABMS $^{35}$Cl[M+1] 515.1.

Step 5

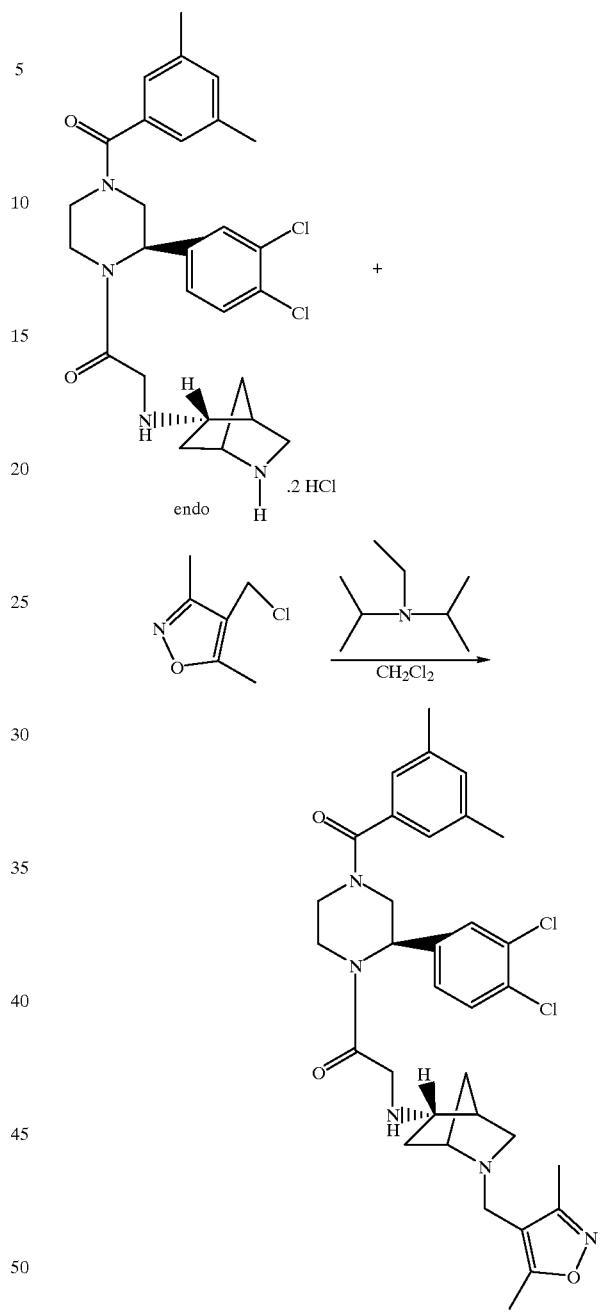

A mixture of the product of step 4 (0.15 g, 0.255 mmol) in CH$_2$Cl$_2$ (4 mL), Hünig's base (0.12 g, 0.9 mmol) and 4-chloromethyl-3,5-dimethyl-isoxazole (37 mg, 0.255 mmol) was stirred at RT for 3 days under N$_2$. After completion, the reaction was diluted with CH$_2$Cl$_2$ (40 mL), washed with brine (30 mL, 3×), dried (Na$_2$SO$_4$), filtered and evaporated to give the product as a brown oil. Product was purified by flash silica gel chromatography, eluting with 5% [(1:9)NH$_4$OH—CH$_3$OH]/95% CH$_2$Cl$_2$ to give a yellow solid (1.4 g), m.p. 78–80° C.; FABMS $^{35}$Cl[M+1] 624.2; HRMS $^{35}$Cl[M+1]$^+$:cal'd for C$_{33}$H$_{40}$N$_5$O$_3$Cl$_3$: 624.2508; Found: 624.2506.

EXAMPLE 63

1,1-Dimethylethyl [1(R)-[[endo-5-[[2-[2(R)-(3,4-dichlorophenyl)-4-(3,5-dimethylbenzoyl)-1-piperazinyl]-2-oxoethyl]amino]-2-azabicyclo[2.2.1]-heptan-2-yl]carbonyl]-2-phenylethyl]carbamate (racemic mixture from enantiomer B)

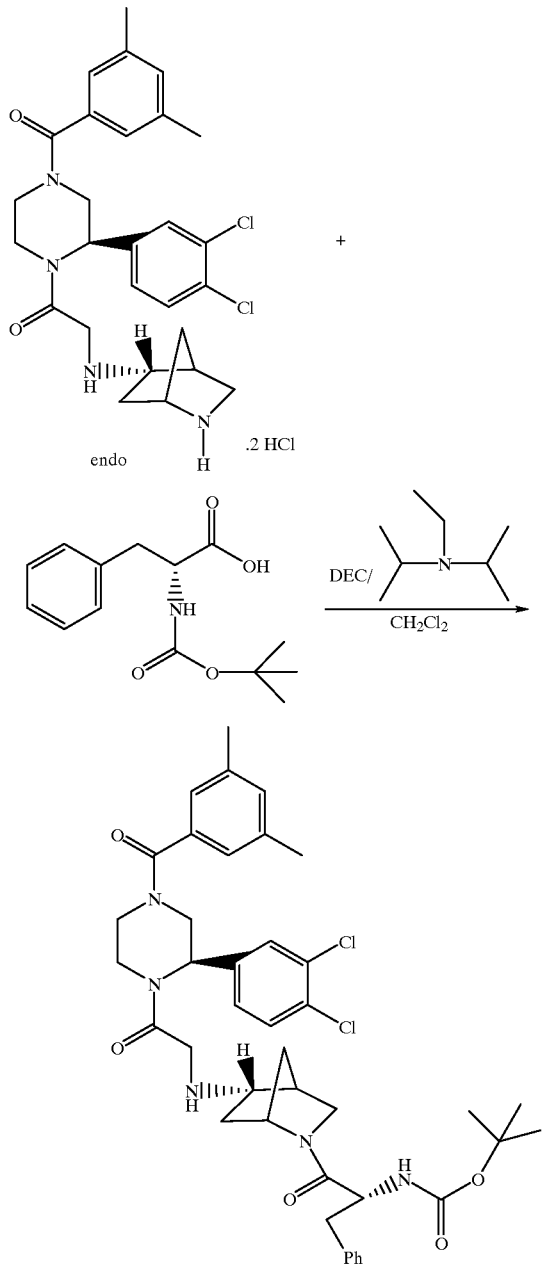

EXAMPLE 64

Endo-2-(2(R)-amino-1-oxo-3-phenylpropyl)-5-[[2-[2(R)-(3,4-dichlorophenyl)-4-(3,5-dimethylbenzoyl)-1-piperazinyl]-2-oxoethyl]amino]-2-aza[2.2.1]heptane, dihydrochloride (enantiomer B)

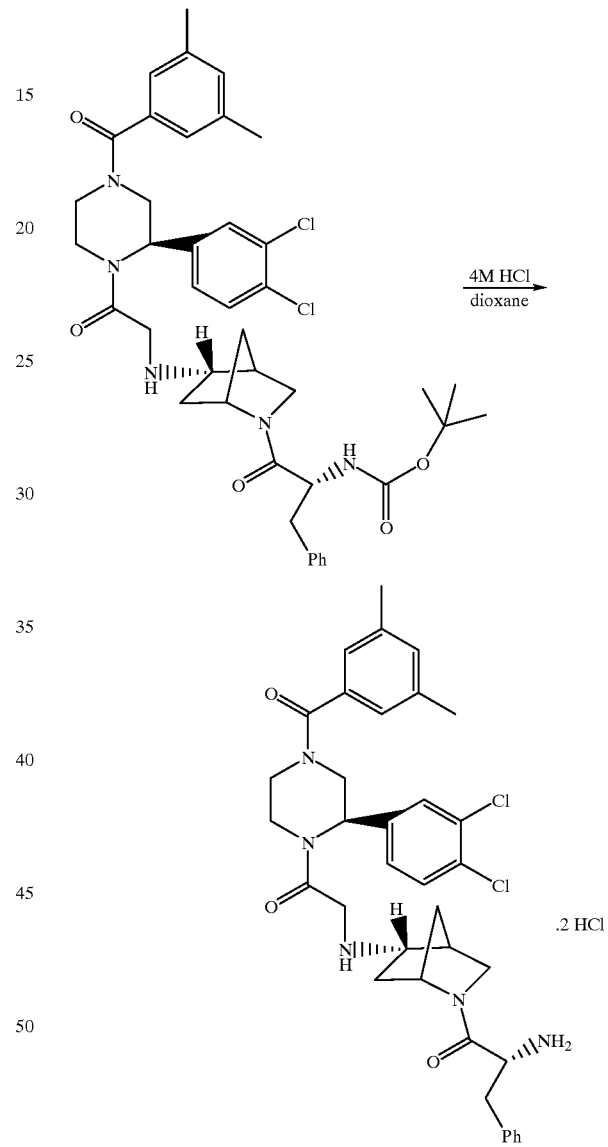

By an analogous method to that described for Example 17, using N-t-BOC-D-phenylalanine in place of N-t-BOC-D-phenylglycine and the product of Example 62, step 4 in place of the product of Example 16, the title compound was obtained as a white solid after flash chromatography on silica gel, m.p. 112–114° C.; HRMS $^{35}$Cl [M+1]$^+$: cal'd for $C_{41}H_{50}N_5O_5Cl_2$: 762.3189; Found: 762.3188.

By an analogous method to that described for Example 18, using compound obtained from Example 63 in place of the product of Example 17, the title compound was obtained as a light yellow solid, m.p. >200° C.; HRMS $^{35}$Cl [M+1]$^+$: cal'd for $C_{36}H_{42}N_5O_3Cl_2$ 662.2665; Found 662.2645.

EXAMPLE 65

1,1-Dimethylethyl 3-[(phenylmethyl)amino]-8-azabicyclo[3.2.1]octane-8-carboxylate (exo and endo products)

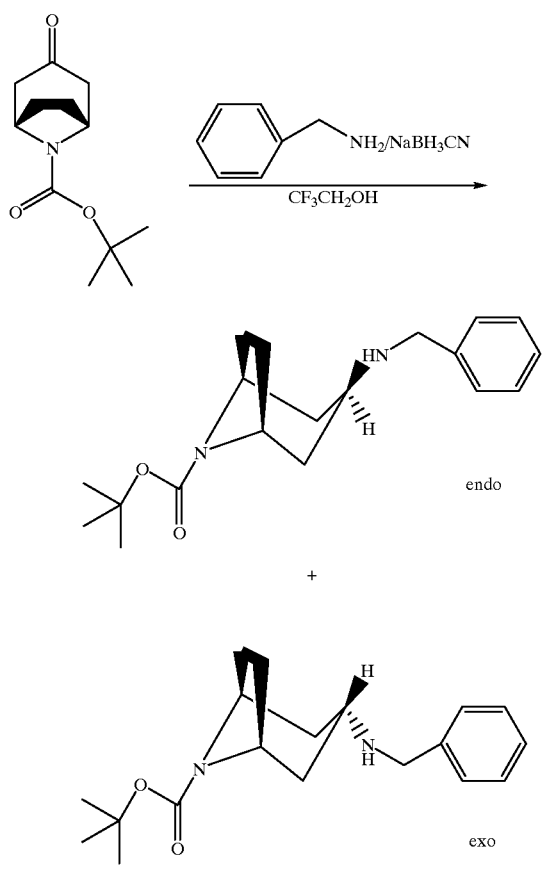

To a solution of compound 2 from Example 52 (10 g, 44.4 mmol) in CF$_3$CH$_2$OH (50 mL) was added benzylamine (4.8 g, 44.4 mmol) and NaBH$_3$CN (5.7 g, 62.84 mmol). The mixture was stirred at RT for 20 h. After completion of the reaction, solvent was removed and the residue was redissolved in EtOAc (200 mL), washed with saturated NaHCO$_3$ solution (150 mL, 2×), dried (Na$_2$SO$_4$), filtered and concentrated to give the product as an oil. The crude material was purified by flash chromatography on silica gel (300 g), eluting with 2% [(NH$_4$OH:CH$_3$OH) (1:9)]/98% CH$_2$Cl$_2$ to give endo product (3.6 g, 11.73 mmol, 25.6%) as a white solid, FAB MS [M+1]$^+$314.4 and exo product (3.6 g, 11.73 mmol, 25.6%) as a clear oil, FAB MS [M+1]$^+$313.3.

EXAMPLE 66

1,1-Dimethylethyl 3-endo-amino-8-azabicyclo[3.2.1]octane-8-carboxylate

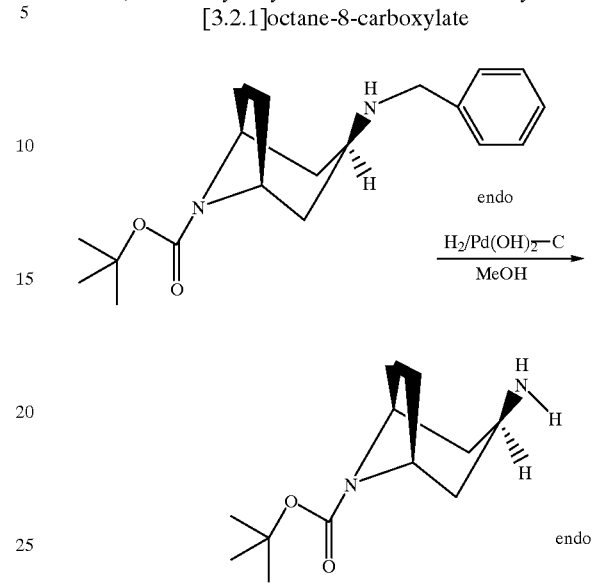

The endo compound (3.6 g, 11.3 mmol) from Example 65 was dissolved in CH$_3$OH (100 mL) and Pd(OH)$_2$—C (0.76 g) was added. The mixture was hydrogenolyzed at 45 psi at RT for 2 days. Additional Pd(OH)$_2$—C (0.76 g) was added and hydrogenolysis was continued at 45 psi for one more day. After completion of the reaction, the catalyst was filtered off and the filtrate was concentrated to give the product as an oil which was purified on flash grade silica gel (150 g), eluting with 5% [(NH$_4$OH: CH$_3$OH) (1:9)]/95% CH$_2$Cl$_2$ to give the title compound as a solid (1.9 g, 8.39 mmol, 74%), FAB MS [M+1]$^+$227.1.

EXAMPLE 67

1,1-Dimethylethyl 3-[[2-[2-(R)-(3,4-dichlorophenyl)-2-oxoethyl]endo-amino]-8-azabicyclo[3.2.1]octane-8-carboxylate

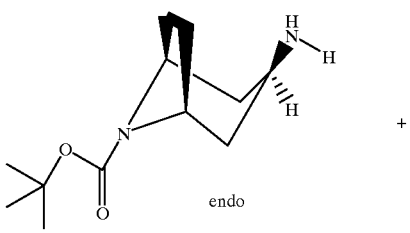

135
-continued

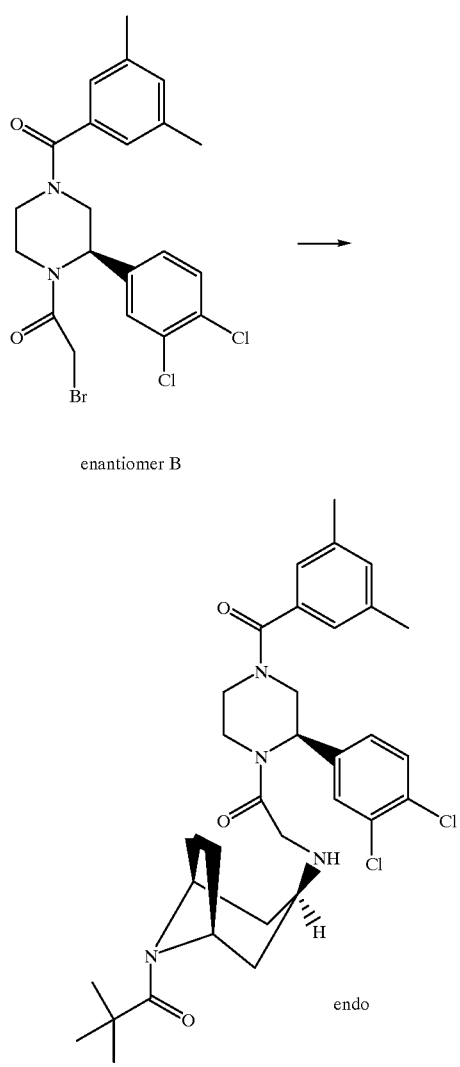

To a solution of the bromoacetyl derivative (1.33 g, 2.75 mmol) from Example 5 in CH$_2$Cl$_2$ (2 mL), and endo compound from Example 66 (0.75 g, 3.3 mmol) was added Hünig's base (0.13 g, 2.75 mmol). The mixture was stirred at RT overnight. The reaction was diluted with CH$_2$Cl$_2$ (100 mL), washed with water (50 mL, 3×), dried (Na$_2$SO$_4$), filtered and concentrated to give the product as a yellow solid (1.9 g). The crude material was purified by flash chromatography on silica gel (100 g), eluting with 3.5% [(1:9) (NH$_4$OH:CH$_3$OH)]/96.5% CH$_3$OH to give the title compound as an off-white solid (1.5 g, 2.38 mmol, 87%), m.p 98–100° C., FAB MS [M+1]$^{+35}$Cl 629.3.

136
EXAMPLE 68

2-(R)-(3,4-Dichlorophenyl)-4-(3,5-dimethylbenzoyl)-1-[[[8-azabicyclo-[3.2.1]octan-3-yl]endo-amino]acetyl]piperazine hydrochloride

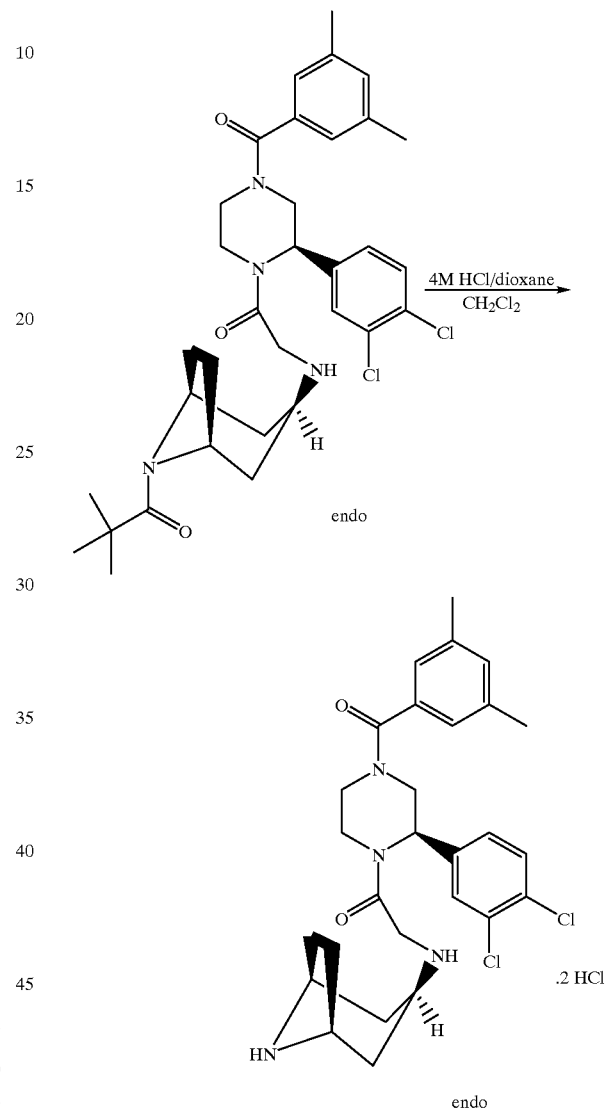

To a solution of the compound of Example 67 (1.46 g, 2.35 mol) in CH$_2$Cl$_2$ (2 mL) was added 4M HCl/dioxane (10 ml, 40 mmol). The mixture was stirred at RT for 1 h. Solvent and excess HCl were evaporated to give the title compound as a white solid in quantitative yield, FAB MS [M+1]$^{+35}$Cl 529.4.

EXAMPLE 69

1,1-Dimethylethyl 3-exo-amino-8-azabicyclo[3.2.1]octane-8-carboxylate

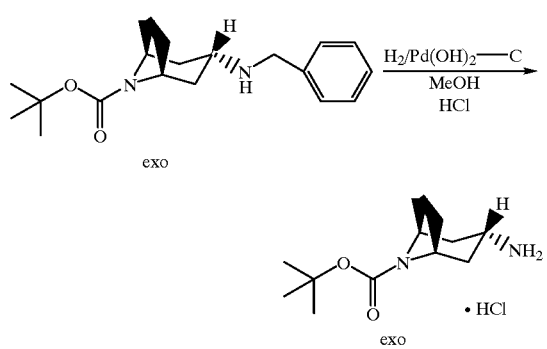

The title compound was prepared as its HCl salt according to the methods described in Example 66, but using the exo product made from Example 65 in place of the endo product from Example 65 with addition of HCl (0.5 equivalent) during the hydrogenolysis, FAB MS [M+1]$^+$227.0.

EXAMPLE 70

1,1-Dimethylethyl 3-[[2-[2-(R)-(3,4-dichlorophenyl)-2-oxoethyl]exo-amino]-8-azabicyclo[3.2.1]octane-8-carboxylate

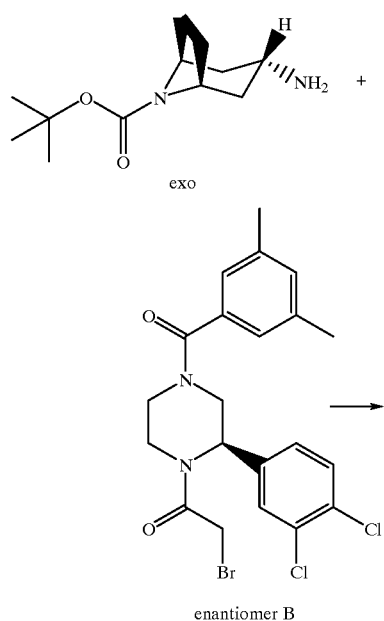

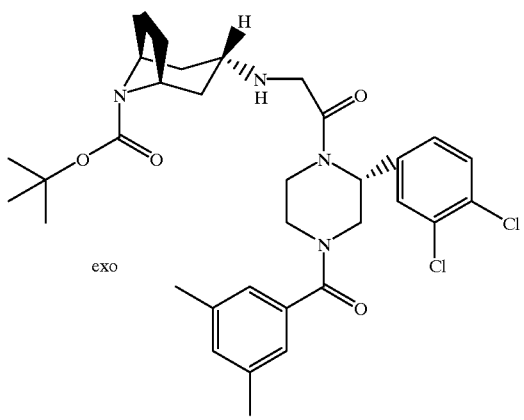

The title compound was prepared by an analogous method to that described in Example 67, but using the compound obtained from Example 69 in place of the endo product made in Example 66, FAB MS [M+1]$^{+35}$Cl 629.2.

EXAMPLE 71

2-(R)-(3,4-Dichlorophenyl)-4-(3,5-dimethylbenzoyl)-1-[[[8-azabicyclo-[3.2.1]octan-3-yl]exo-amino]acetyl]piperazine hydrochloride

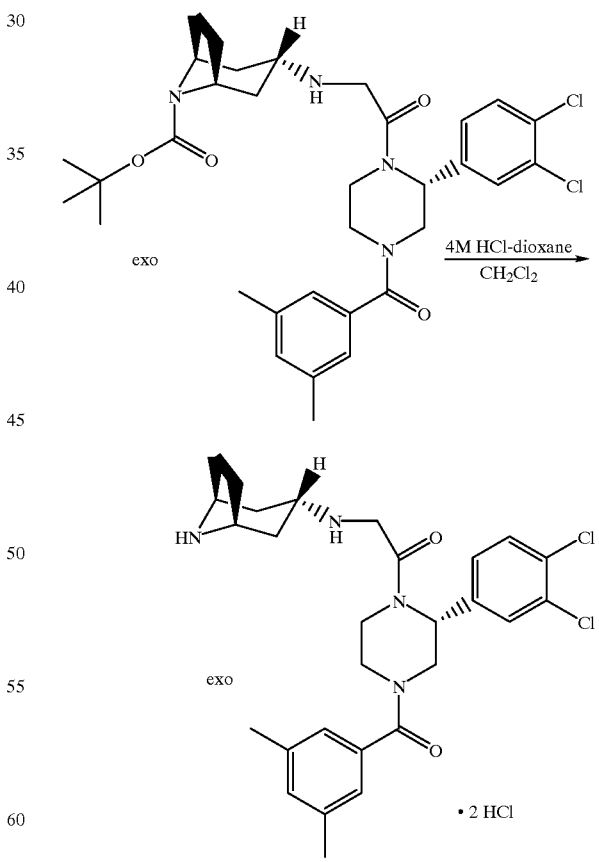

The title compound was prepared by an analogous method to that described in Example 68, but using the product of Example 70 in place of the endo product from Example 67. FAB MS [M+1]$^{+35}$Cl 529.3.

EXAMPLE 72

1,1-Dimethylethyl [1(S)-[[exo-3-[[2-2(R)-(3,4-dichlorophenyl)-4-(3,5-dimethy-lbenzoyl)-1-piperazinyl]-2-oxoethyl]amino]-8-aza[3.2.1]octan-8-yl]carbonyl]-2-phenylethyl]carbamate (enantiomer B)

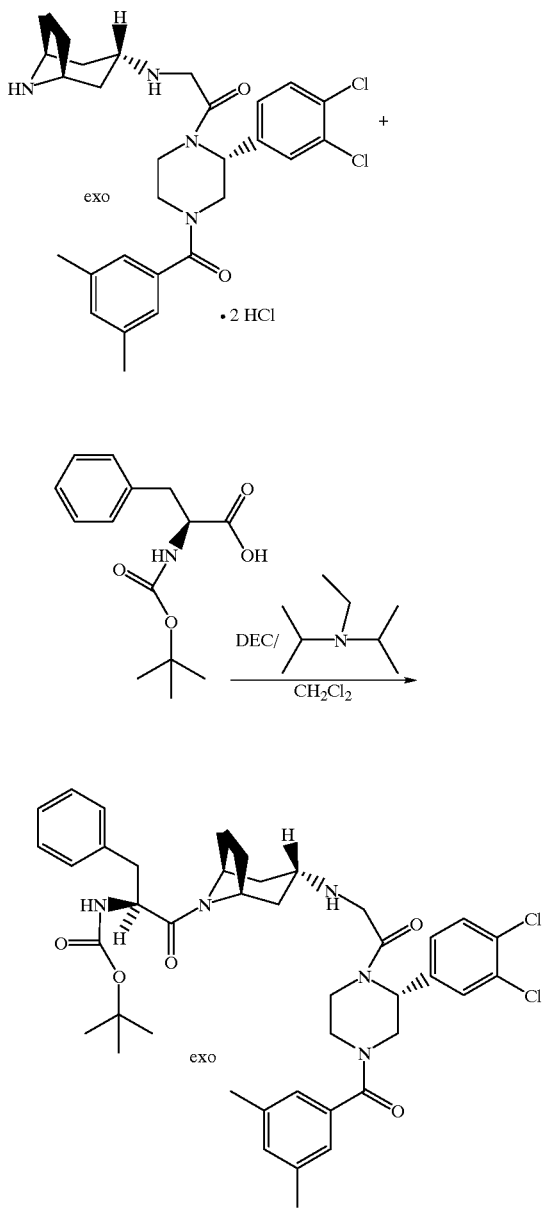

By an analogous method to that described for Example 17, using the product of Example 71 and reacting with N-t-BOC-L-phenylalanine, the title compound was obtained as a white solid after flash chromatography on silica gel, m.p. 112–114° C., HRMS $^{35}$Cl [M+1]$^+$: cal'd for $C_{42}H_{52}N_5O_5Cl_2$ 776.3346, Found : 776.3360.

EXAMPLE 73

Exo-8-(2(S)-amino-1-oxo-3-phenylpropyl)-3-[[2-[2(R)-(3,4-dichlorophenyl)-4-(3,5-dimethylbenzoyl)-1-piperazinyl]-2-oxoethyl]amino]-8-aza[3.2.1]octane, dihydrochloride (enantiomer B)

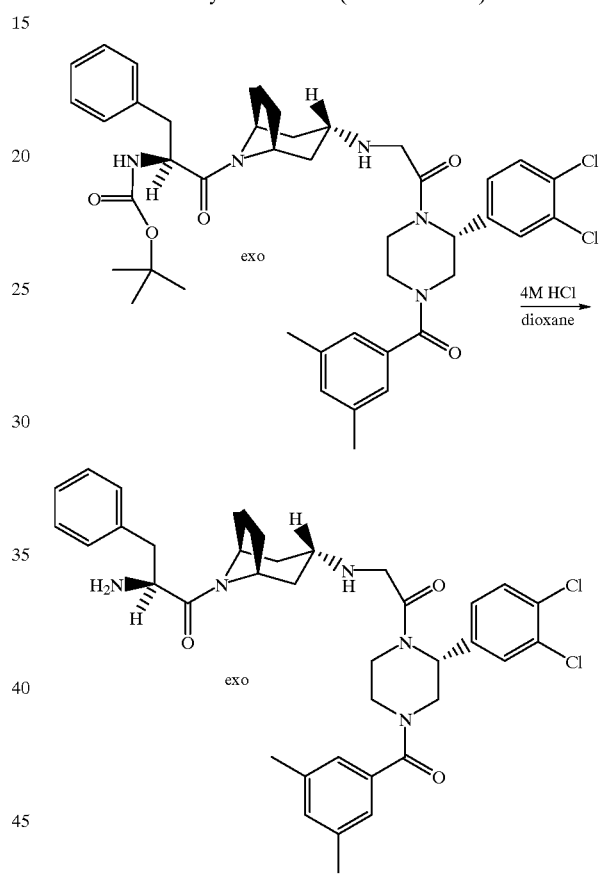

By an analogous method to that described for Example 18, using compound obtained from Example 72 in place of the product of Example 17, the title compound was obtained as a light yellow solid, m.p. >200° C.; HRMS $^{35}$Cl [M+1]$^+$:cal'd for $C_{37}H_{44}N_5O_3Cl_2$ 676.2821, Found: 676.2825.

EXAMPLE 74

1,1-Dimethylethyl [1(S)-[[endo-3-[[2-2(R)-(3,4-dichlorophenyl)-4-(3,5-dimethylbenzoyl)-1-piperazinyl]-2-oxoethyl]amino]-8-aza[3.2.1]octan-8-yl]carbonyl]-2-phenylethyl]carbamate (enantiomer B)

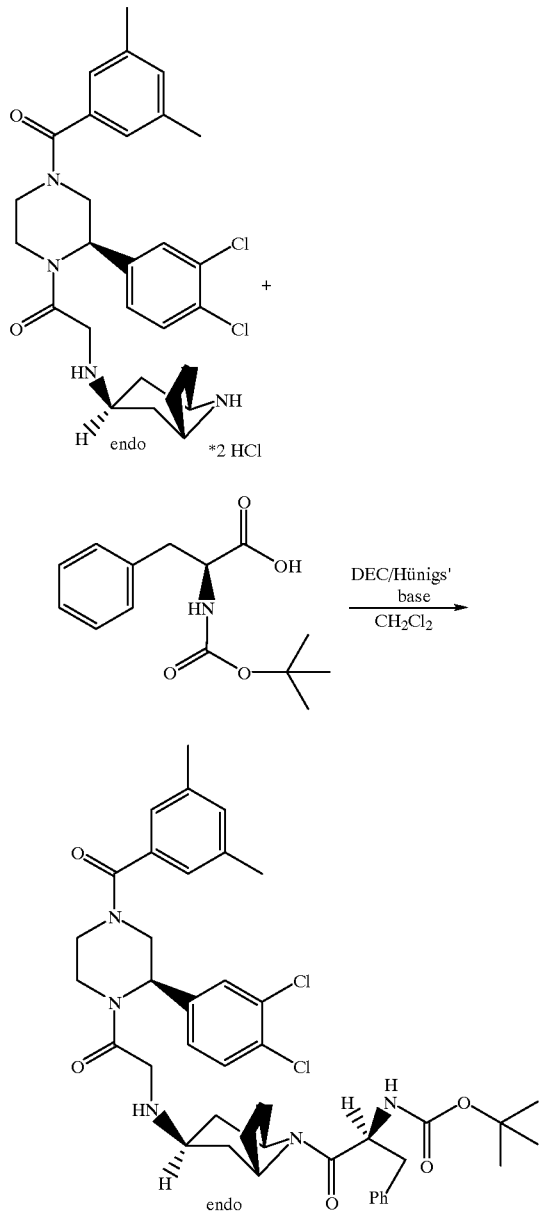

By an analogous method to that described for Example 17, using the product of Example 67 and reacting with N-t-BOC-L-phenylalanine, the title compound was obtained as a white solid after flash chromatography on silica gel, m.p. 112–114° C., HRMS $^{35}$Cl [M+1]$^+$:cal'd for $C_{42}H_{52}N_5O_5Cl_2$ 776.3346, Found : 776.3352.

EXAMPLE 75

Endo-8-(2(S)-amino-1-oxo-3-phenylpropyl)-3-[[2-[2(R)-(3,4-dichlorophenyl)-4-(3,5-dimethylbenzoyl)-1-piperazinyl]-2-oxoethyl]amino]-8-aza[3.2.1]octane, dihydrochloride (enantiomer B)

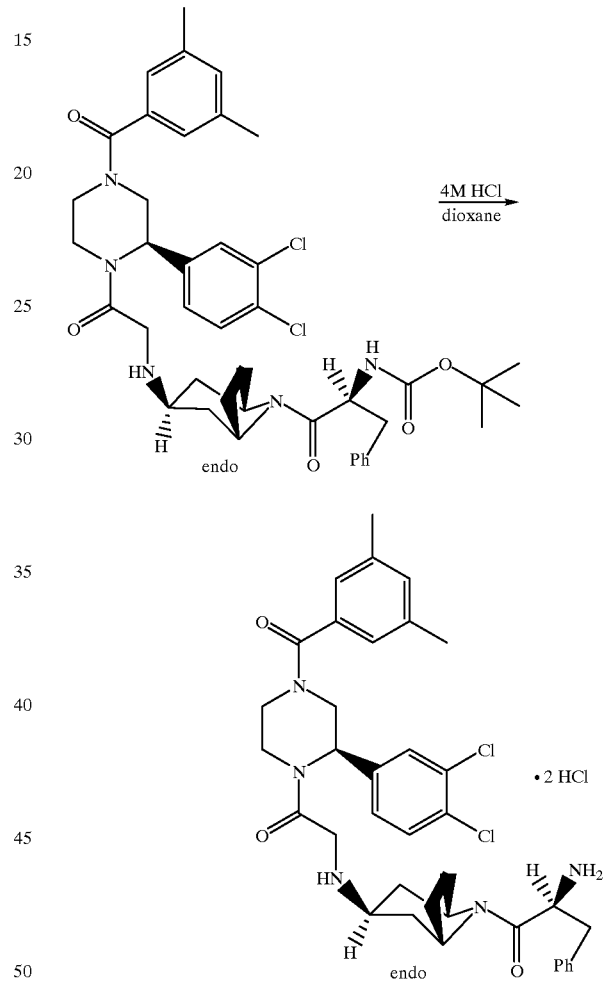

By an analogous method to that described for Example 18, using the product of Example 74 in place of the product of Example 17, the title compound was obtained as a light yellow solid, m.p. >200° C.; HRMS $^{35}$Cl [M+1]$^+$:cal'd for $C_{37}H_{44}N_5O_3Cl_2$ 676.2821, Found: 676.2816.

EXAMPLE 76

1,1-Dimethylethyl [1(R)-[[exo-3-[[2-2(R)-(3,4-dichlorophenyl)-4-(3,5-dimethylbenzoyl)-1-piperazinyl]-2-oxoethyl]amino]-8-aza[3.2.1]octan-8-yl]carbonyl]-2-phenylethyl]carbamate (enantiomer B)

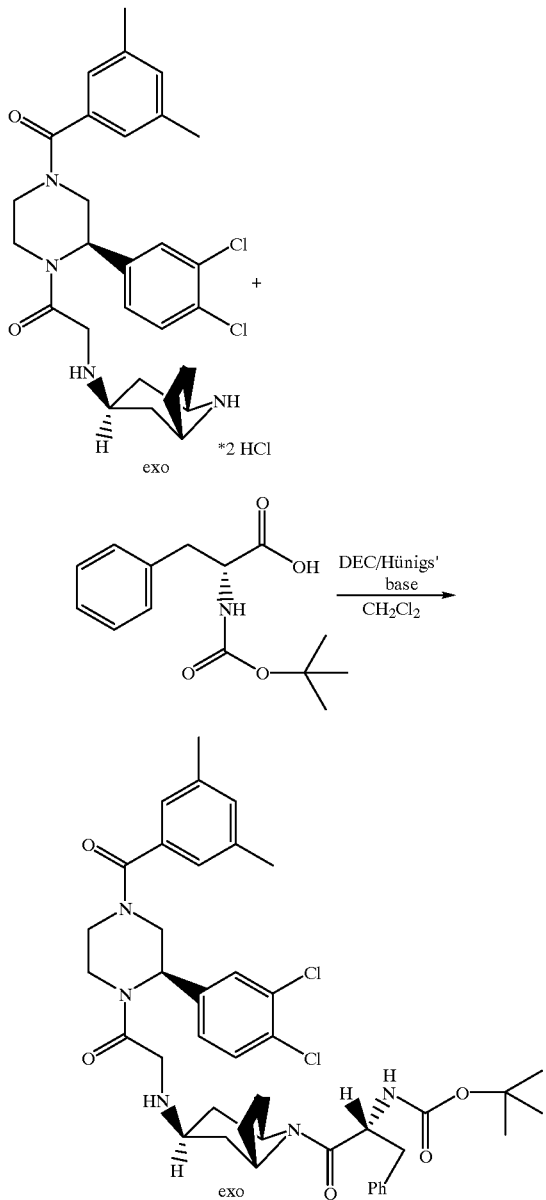

By an analogous method to that described for Example 17, using the product of Example 71 and reacting with N-t-BOC-D-phenylalanine, the title compound was obtained as a white solid after flash chromatography on silica gel, m.p. 112–114° C., HRMS $^{35}$Cl [M+1]$^+$:cal'd for $C_{42}H_{52}N_5O_5Cl_2$ 776.3346, Found: 776.3357.

EXAMPLE 77

Exo-8-(2(R)-amino-1-oxo-3-phenylpropyl)-3-[[2-[2(R)-(3,4-dichlorophenyl)-4-(3,5-dimethylbenzoyl)-1-piperazinyl]-2-oxoethyl]amino]-8-aza[3.2.1]octane, dihydrochloride (enantiomer B)

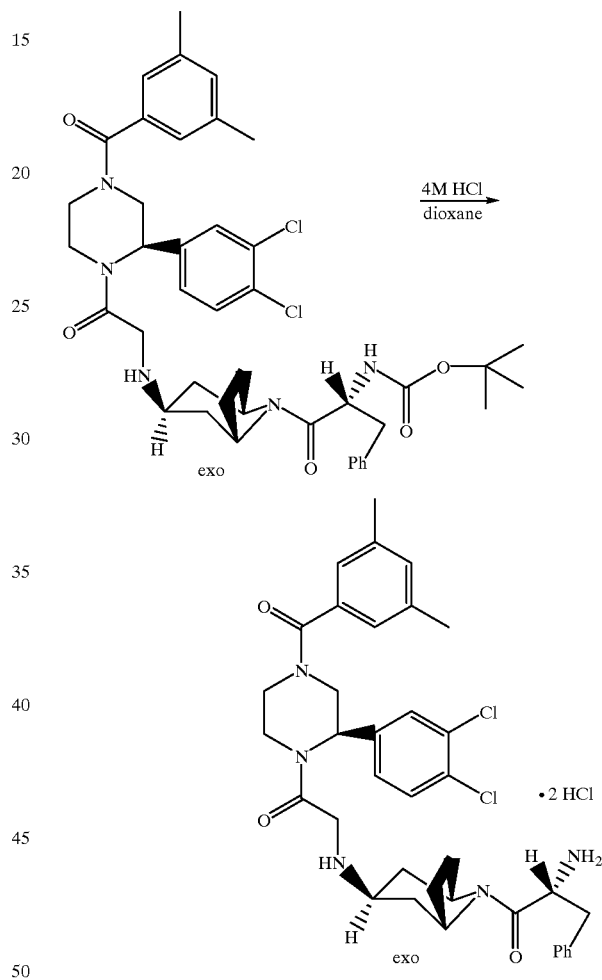

By an analogous method to that of Example 18, using the product of Example 76 in place of the product of Example 17, the title compound was obtained as a light yellow solid, m.p. >200° C.; HRMS $^{35}$Cl [M+1]$^+$: cal'd for $C_{37}H_{44}N_5O_3Cl_2$ 676.2821; Found : 676.2818.

EXAMPLE 78

(±)-N-[4-[[Endo-5-[[2-[2(R)-(3,4-dichlorophenyl)-4-(3,5-dimethyl-benzoyl)-1-piperazinyl]-2-oxoethyl]amino]-2-azabicyclo[2.2.1]heptan-2-yl]methyl]-phenyl]acetamide (from enantiomer B)

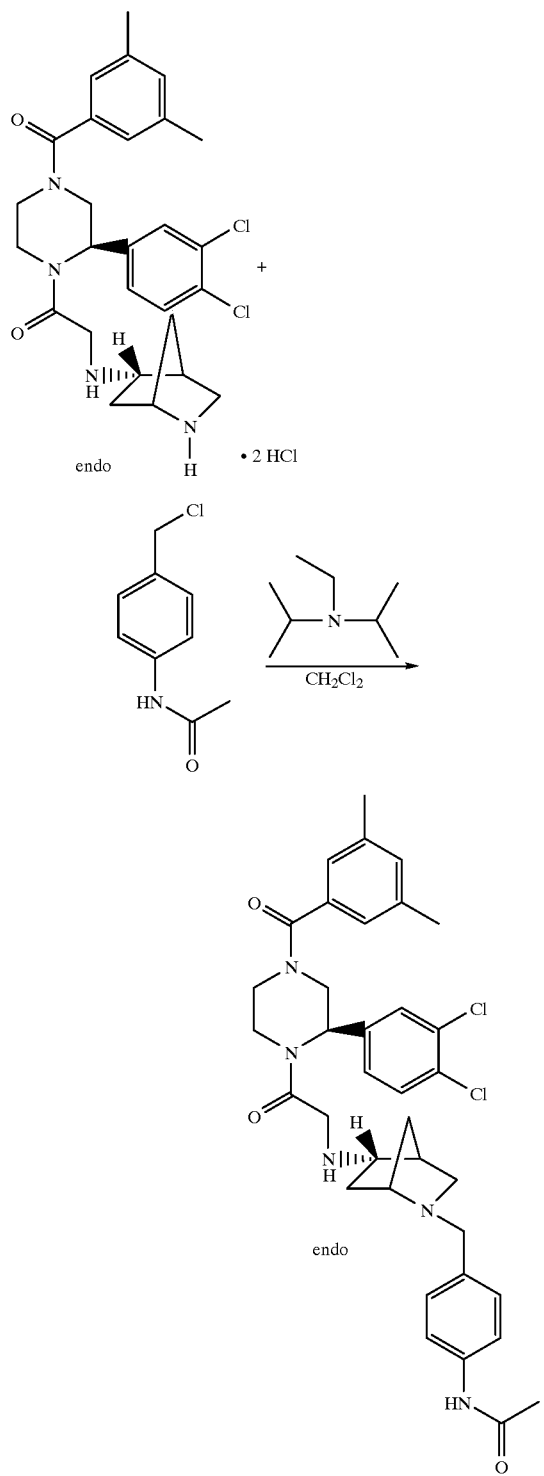

By an analogous method to that described for Example 62, using 4-aceto-aminobenzyl chloride in place of 4-chloromethyl-3,5-dimethyl-isoxazole, the title compound was obtained as a white solid after silica gel chromatography, m.p. 122–124° C.; HRMS $^{35}$Cl [M+1]$^+$ :calc'd for $C_{36}H_{42}N_5O_3Cl_2$ 662.2665, Found: 662.2652.

EXAMPLE 79

(±)-N-[3-[[Endo-5-[[2-[2(R)-(3,4-dichlorophenyl)-4-(3,5-dimethyl-benzoyl)-1-piperazinyl]-2-oxoethyl]amino]-2-azabicyclo[2.2.1]heptan-2-yl]methyl]-phenyl]acetamide (from enantiomer B)

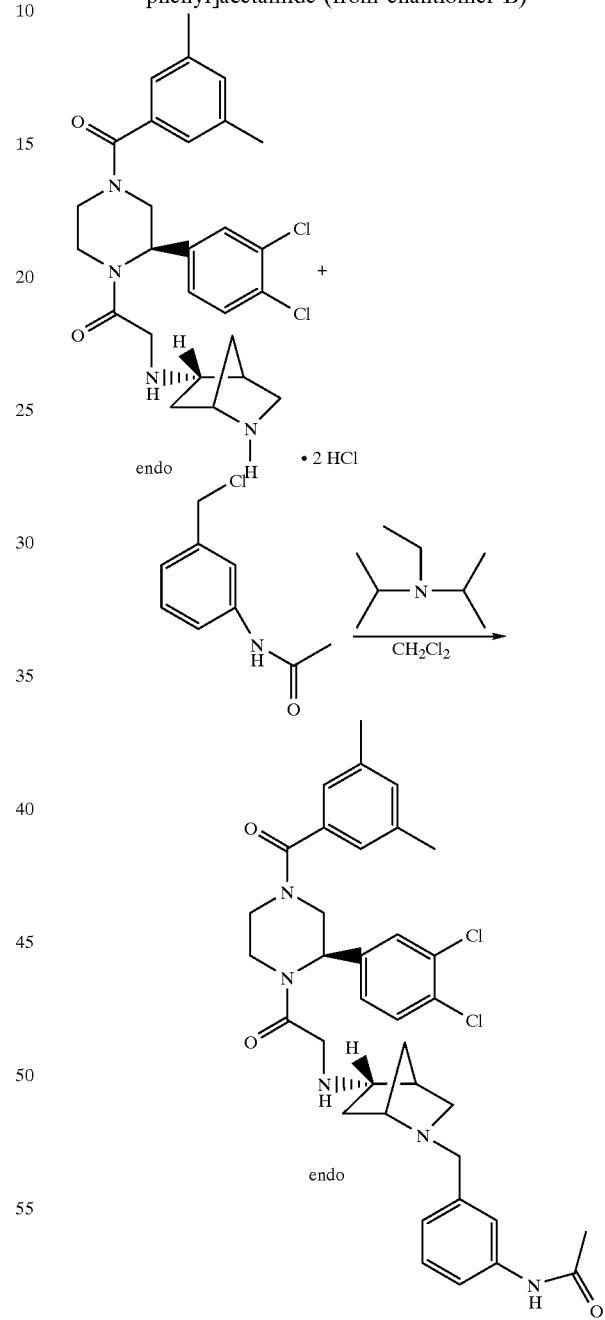

By an analogous method to that described for Example 62, using 3-aceto-aminobenzyl chloride in place of 3-chloromethyl-3,5-dimethyl-isoxazole, the title compound was obtained as a white solid after silica gel chromatography, m.p. 111–113° C.; HRMS $^{35}$Cl [M+1]$^+$: calc'd for $C_{36}H_{42}N_5O_3Cl_2$ 662.2665, Found: 662.2658.

EXAMPLE 80

(±)-1,1-Dimethylethyl trans-2-[[5-[3-[2(R)-(3,4-dichlorophenyl)-4-(3,5-dimethylbenzoyl)-1-piperazinyl]-3-oxopropyl]-1(S),4(S)-2,5-diaza-bicyclo-[2.2.1]heptan-2-yl]carbonyl]-3-phenyl-1-azetidinecarboxylate (enantiomer B)

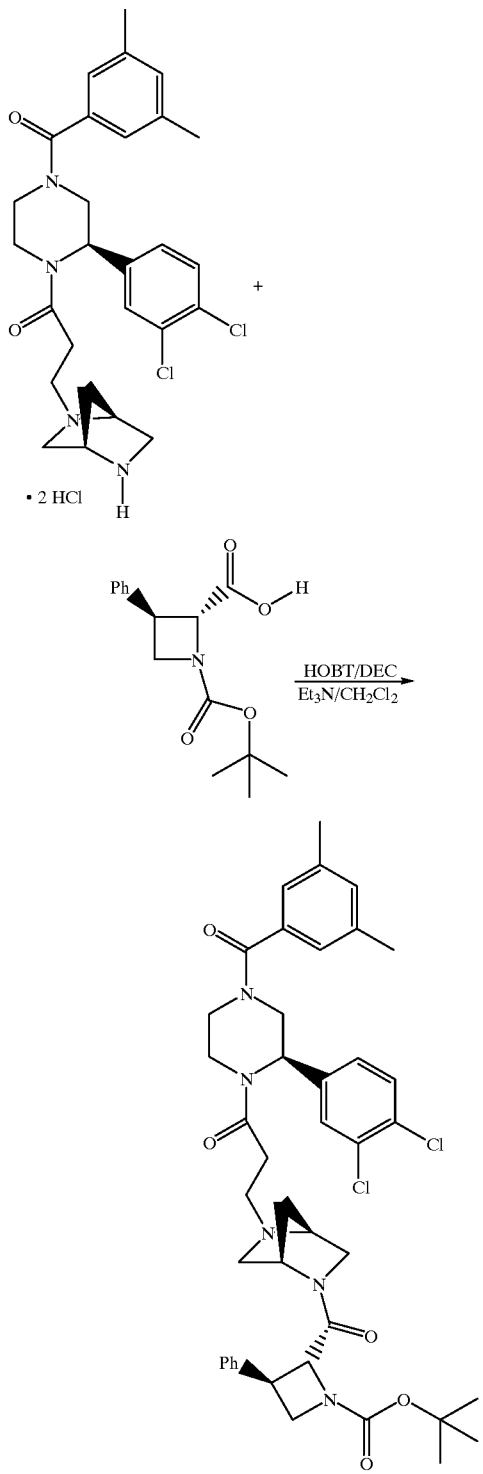

By an analogous method to that described for Example 17, using trans-N-t-BOC-2-phenyl azatidine carboxylic acid in place of N-t-BOC-D-phenyl-glycine, the title compound was obtained as a white solid after silica gel chromatography, m.p. 143–145° C.; FABMS $^{35}$Cl [M+1]$^+$ 774.

EXAMPLE 81

(±)-5-[3-[2(R)-(3,4-Dichlorophenyl)-4-(3,5-dimethylbenzoyl)-1-piper-azinyl]-3-oxopropyl]-2-[(trans-3-phenyl-2-azetidinyl)carbonyl]-1(S),4(S)-2,5-diazabicyclo[2.2.1]heptane, dihydrochloride (enantiomer B)

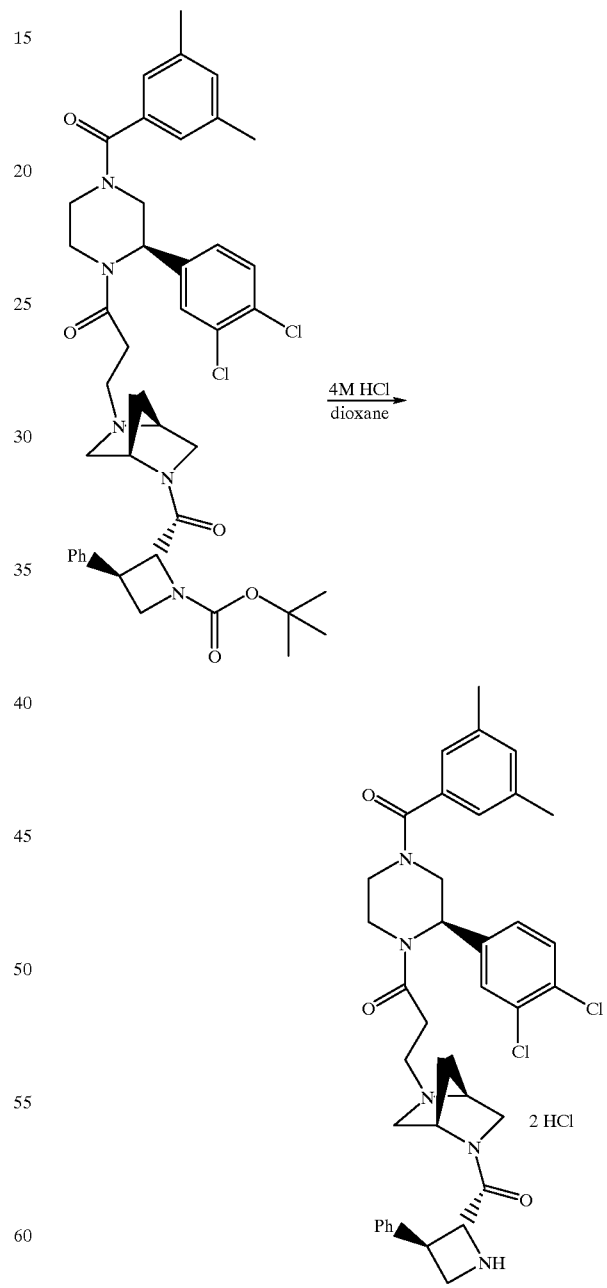

By an analogous method to that described for Example 18, the title compound was obtained as a light yellow solid, m.p. 175–180° C.; FABMS $^{35}$Cl [M+1]$^+$674.

EXAMPLE 82

The following compounds were prepared by analogous methods to those described in Examples 6, 47, 48, 49, 50 using compound (A) from Example 6 in place of compound (5) from Example 46.

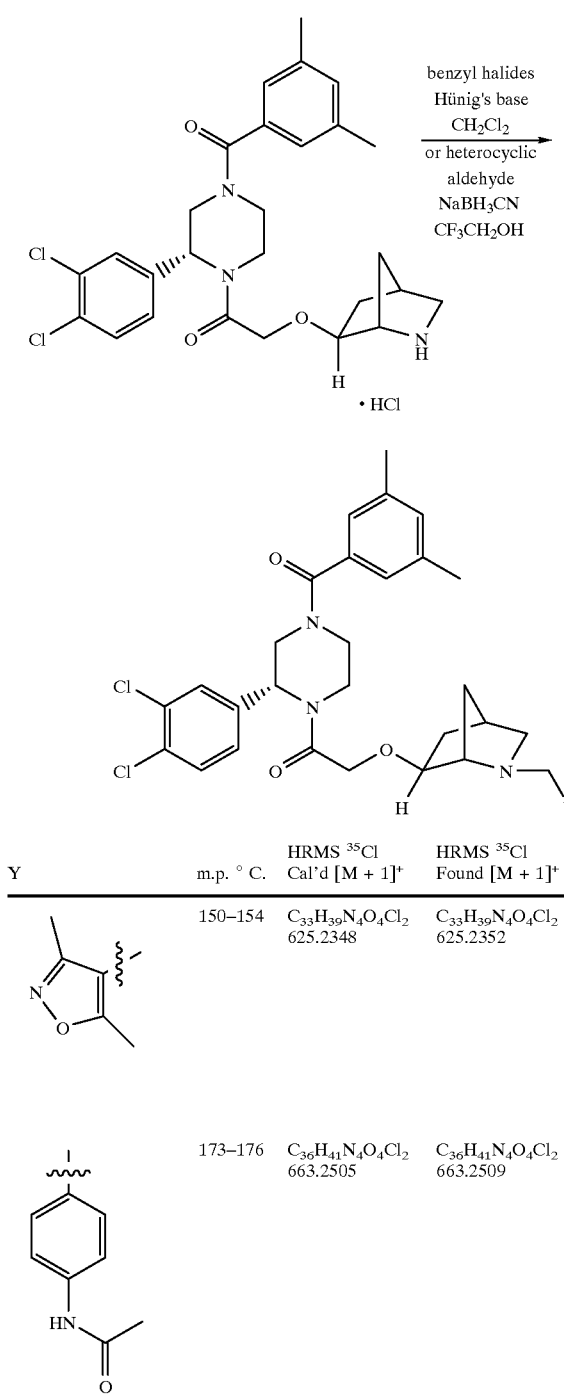

| Y | m.p. °C. | HRMS $^{35}$Cl Cal'd [M + 1]$^+$ | HRMS $^{35}$Cl Found [M + 1]$^+$ |
|---|---|---|---|
| (3,5-dimethylisoxazolyl) | 150–154 | $C_{33}H_{39}N_4O_4Cl_2$ 625.2348 | $C_{33}H_{39}N_4O_4Cl_2$ 625.2352 |
| (4-acetamidophenyl) | 173–176 | $C_{36}H_{41}N_4O_4Cl_2$ 663.2505 | $C_{36}H_{41}N_4O_4Cl_2$ 663.2509 |
| (phenyl) | 108–112 | $C_{34}H_{38}N_3O_3Cl_2$ 606.2290 | $C_{34}H_{38}N_3O_3Cl_2$ 606.2295 |
| (3-thienyl) | 117–122 | $C_{32}H_{36}N_3O_3SCl_2$ 612.1854 | $C_{32}H_{36}N_3O_3Cl_2$ 612.1849 |

EXAMPLE 83

A series of derivatives of (−)-1-[3-[(1S),4(S)-2,5-diazabicyclo[2.2.1]-heptan-2-yl)-1-oxopropyl]-2-(R)-(3,4-dichlorophenyl)-4-(3,5-dimethyl-benzoyl)-piperazine hydrochloride salt (from Example 16) was prepared as pure enantiomers according to the methods described for Example 9 or Example 50, but using appropriate reagents in place of benzyl bromide (Example 9) or 3-thiophenecarboxaldehyde (Example 50).

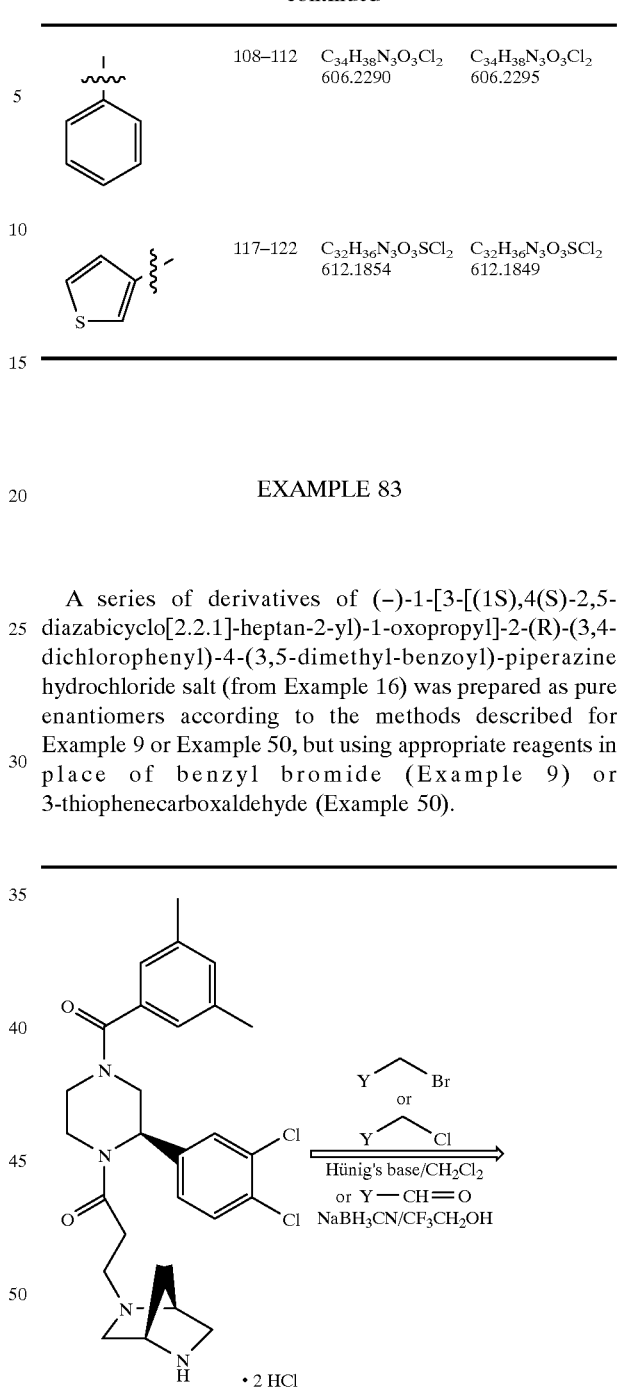

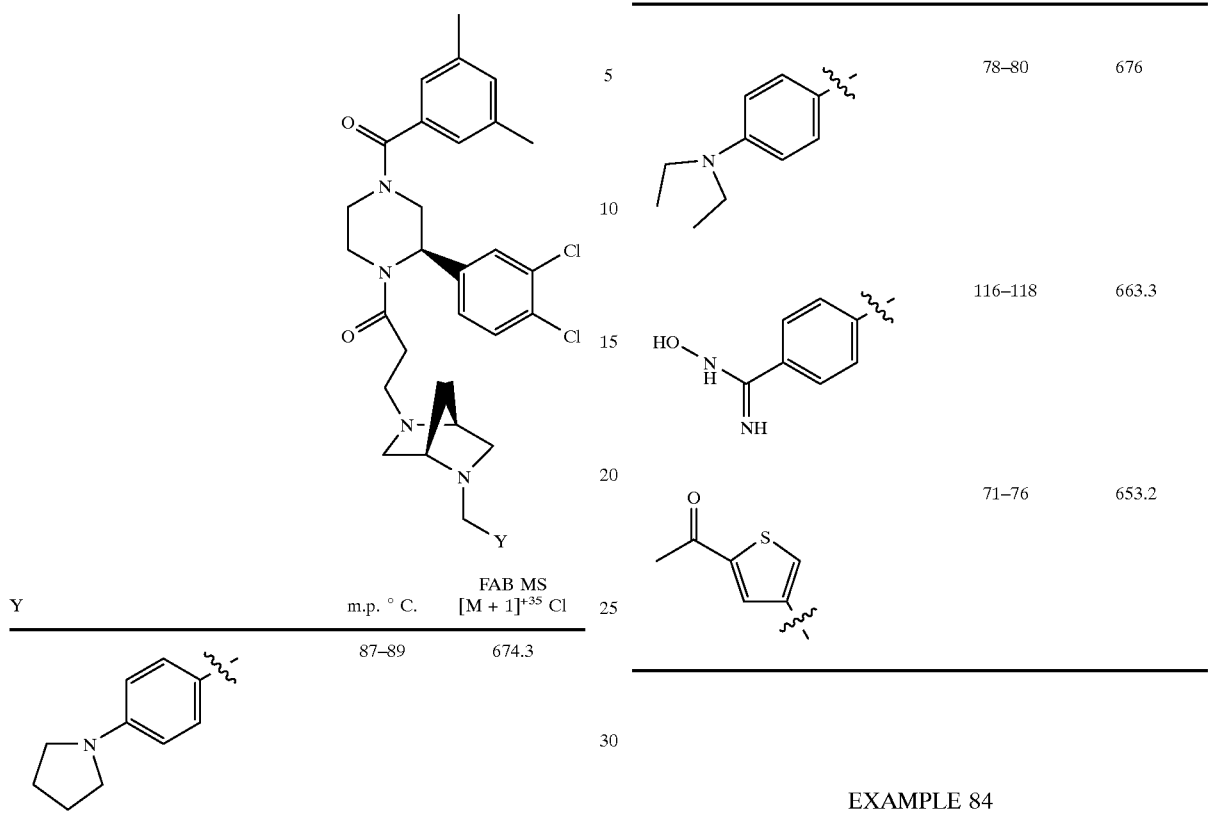
EXAMPLE 84
A series of benzylurea derivatives of the product of Example 16 was prepared according to the following scheme and their spectral data are listed as below.
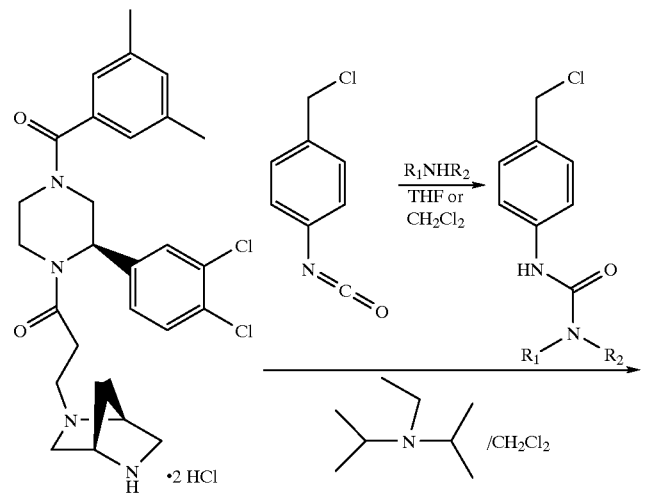

-continued
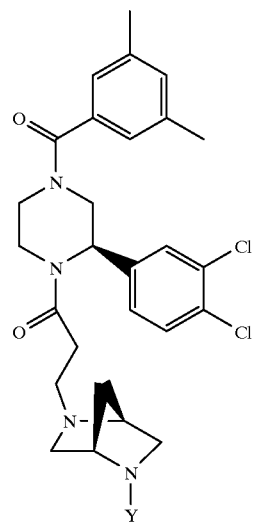
| Y | m.p. ° C. | FAB MS [M + 1]+35 Cl |
|---|---|---|
| 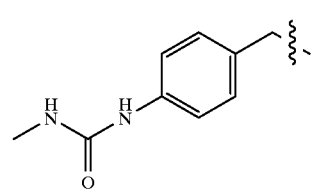 | 115–118 | 677 |
| 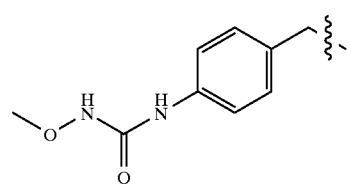 | 111–115 | 693 |
| 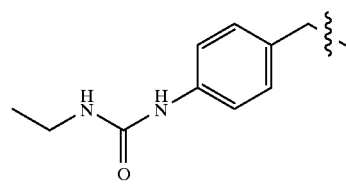 | 135–140 | 691 |
| 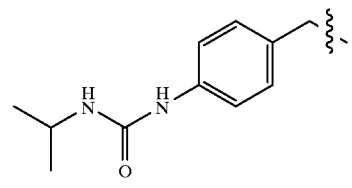 | 120–123 | 705 |

-continued

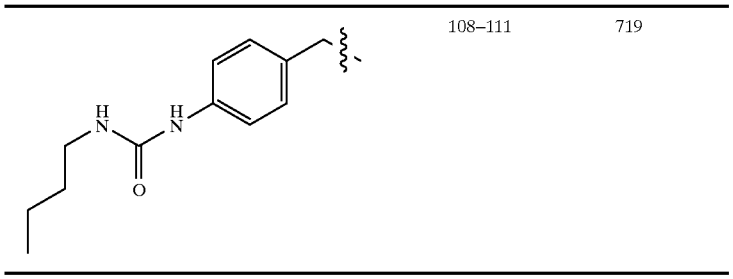

| | | 108–111 | 719 |

Using the test procedures described above, the following data (Ki) were obtained for preferred and/or representative compounds of formula I:

| Ex. | Ki (NK$_1$) (nM) | Ki (NK$_2$) (nM) |
|---|---|---|
| 19 (R = C$_6$H$_5$—CH$_2$—, from L-phenylalanine) | 45 | 14 |
| 20 (R = 2-thienyimethyl, from L-alanine) | 16 | 0.35 |
| 30 | 34 | 24 |
| 35 (R = —CH$_3$) | 6.3 | 0.93 |
| 50 | 1.8 | 2.6 |
| 51 | 1.5 | 4.4 |

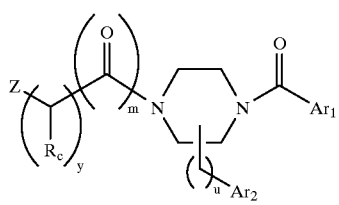

| 56 | >100 | 55 |
| 58 | 19 | 57 |

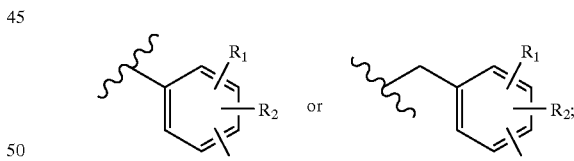

| 67 | 159 | 9.3 |

What is claimed is:

1. A compound of the formula:

[structure]

wherein u is 0 to 2;

m is 1, and y is 1 to 3; or m is 2, and y is 0;

each $R_c$ is independently selected from the group consisting of H and $C_1$–$C_6$ alkyl, with the proviso that no more than one $R_c$ is other than H;

$R_a$ and $R_b$ are independently selected from the group consisting of H,

[structure]

or $R_a$ and $R_b$ together are $C_3$–$C_6$ alkylene and are attached to the same nitrogen so that $R_a$ and $R_b$, together with the nitrogen to which they are attached, form a 4 to 7 membered ring;

$R_1$ and $R_2$ are independently selected from the group consisting of H, $C_1$—$C_6$alkyl, —CF$_3$, —C$_2$F$_5$, Cl, Br, I, F, —NO$_2$, —OR$_a$, —CN, —NR$_a$R$_b$, —C(O)—R$_a$, —O—C(O)—R$_a$, -continued

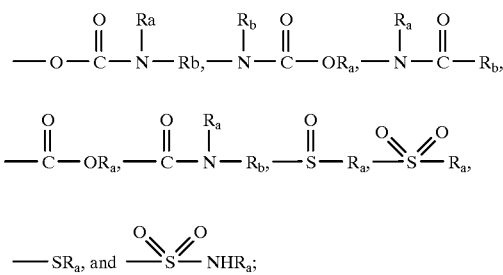

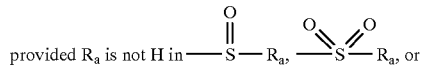

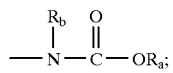

provided $R_a$ is not H in

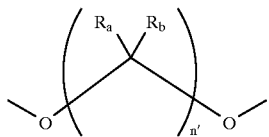

or when $R_1$ and $R_2$ are on adjacent carbons on a ring, they can form

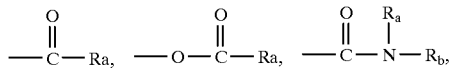

wherein n' is 1 or 2;

$R_3$ is independently selected from the group consisting of H, $C_1$-$C_6$ alkyl, —$CF_3$, —$C_2F_5$, Cl, Br, I, F, —$OR_a$, —$OCF_3$, phenyl,

$X_6$ is =S or =$NR_8$;
$R_b'$ is $R_b$ or —$OR_b$;
$R_8$ is $R_m$, —$OR_m$, —O$(CH_2)_{n10}$—$R_k$ or —O$(CH_2)_{n11}$—$R_n$;
$R_m$ is $R_a$, thienyl or pyridyl;
$R_k$ is $R_m$, —$OR_m$, —$SO_3H$, —$PO_3H$ or

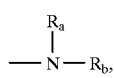

and $n_{10}$ is 2–4;
$R_n$ is CN or

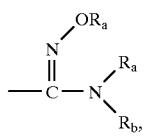

and $n_{11}$ is 1–4;

$X_7$ is =O, =S, =$NR_a$ or =N—$OR_a$;
$Ar_1$ is

Ar₁ is 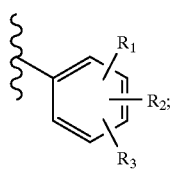   Ar₂ is 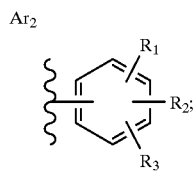

Z is

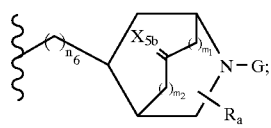

$m_1$ and $m_2$ are independently 0 or 1;
$n_6$ is 0 to 2;
$X_{5b}$ is (H, H);
G is

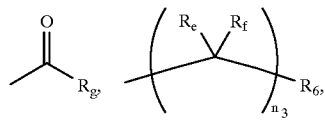

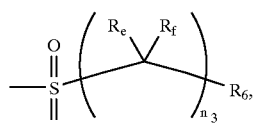

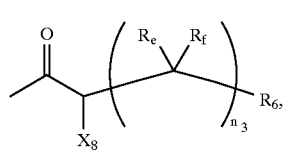

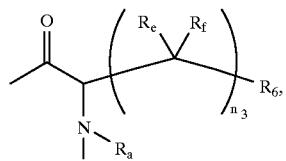

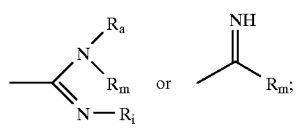

$n_3$ is 0 to 4;
$X_8$ is —$OR_m$, —$SR_m$, halogen, —O—$(CH_2)_{n10}$—$R_k$, —O—$(CH_2)_{n11}$—$R_n$, —S—$(CH_2)_{n10}$—$R_k$ or —S—$(CH_2)_{n11}$—$R_n$;

$R_g$ is

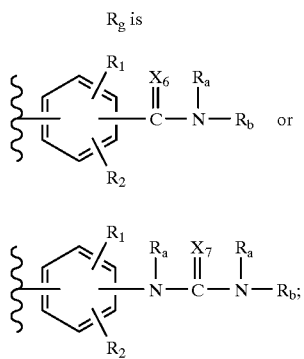

$R_h$ is H, $C_1$–$C_6$ alkyl, —C(O)$R_a$, —C(O)N$R_a R_b$, —C(O)O$R_a$, —C(O)CH(N($R_a$)($R_b$))—$R_7$, —SO$_2 R_m$, —(CH$_2$)$_{n10}$—$R_k$, —(CH$_2$)$_{n11}$—$R_n$,

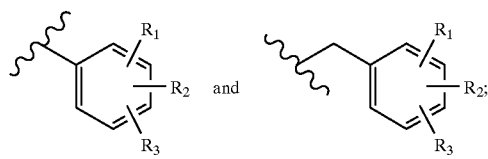

provided that when $R_h$ is —C(O)O$R_a$, Ra is not H;

$R_i$ is —CN or —$R_a$;

$R_e$ and $R_f$ are independently selected from the group consisting of H,

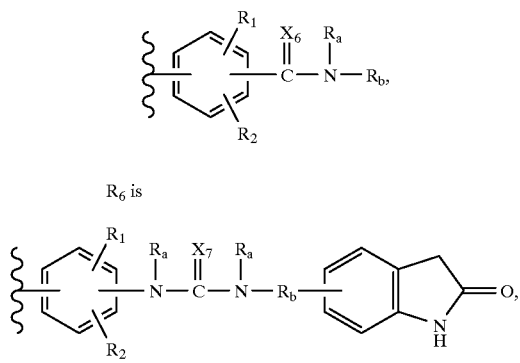

$C_1$—$C_6$ alkyl, allyl, $R_6$ is

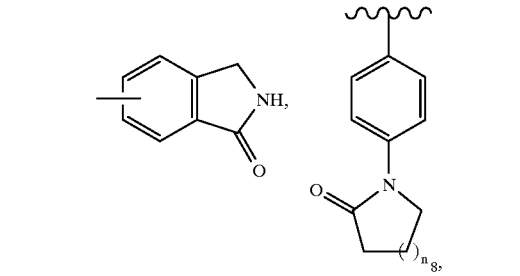

$R_6$ is

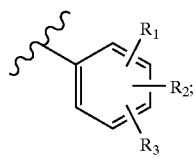

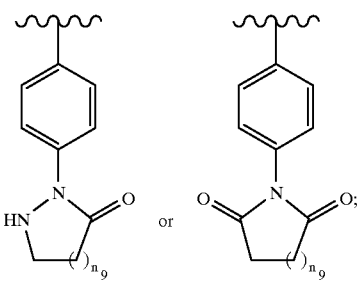

and when G is

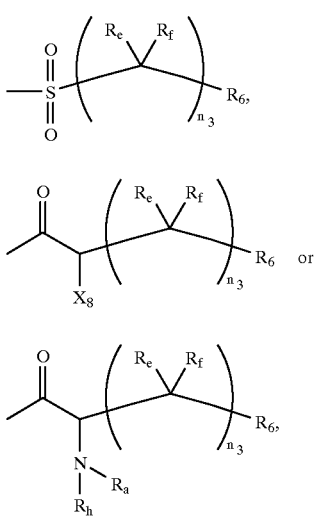

$R_6$ can also be

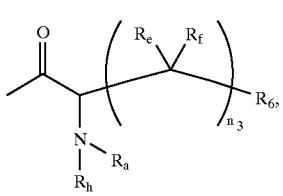

$n_8$ is 0, 1 or 2; $n_9$ is 1 or 2;

$R_7$ is

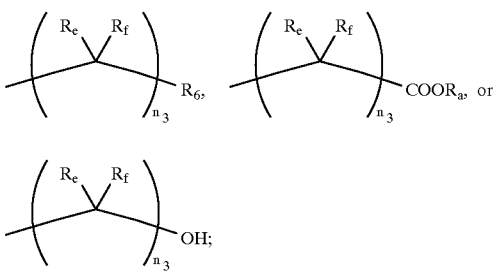

provided that when $X_{5b}$ is (H,H), $m_1$ is 0 or 1 and $m_2$ is 0, G is not

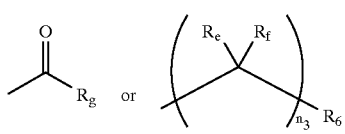

when R$_3$ is H, C$_1$–C$_6$ alkyl, —CF$_3$, —C$_2$F$_5$, Cl, Br, I, F, —OR$_a$, —OCF$_3$, phenyl,

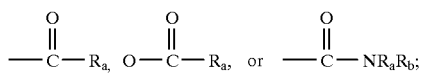

or an enantiomer or diastereomer thereof, or a pharmaceutically acceptable salt thereof.

2. A compound of claim 1 wherein m is 1 and u is 0.

3. A compound selected from the group consisting of: compounds represented by the formulas

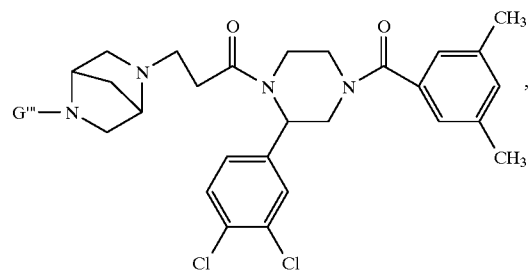

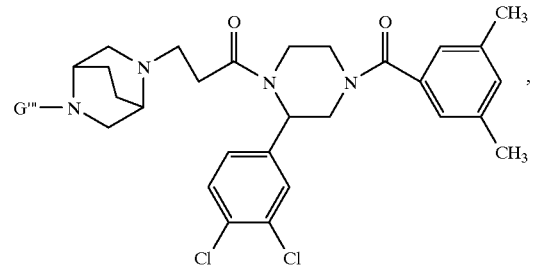

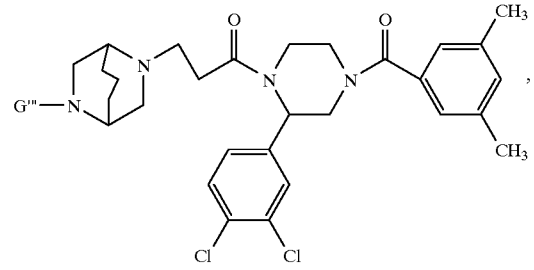

wherein G''' is selected from the group consisting of

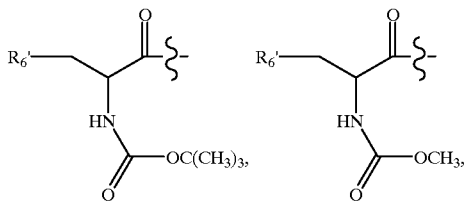

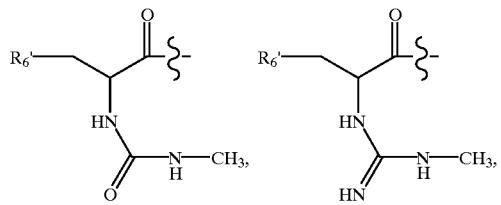

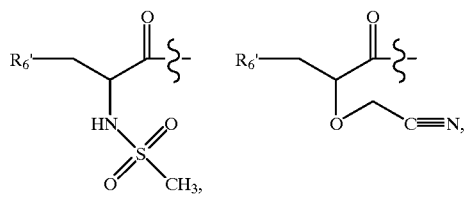

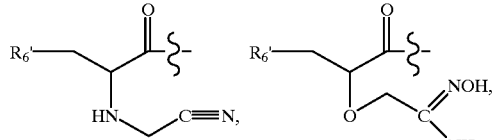

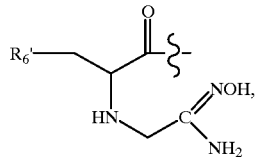

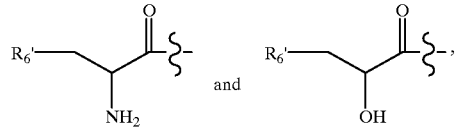

wherein R$_6$' is selected from the group consisting of

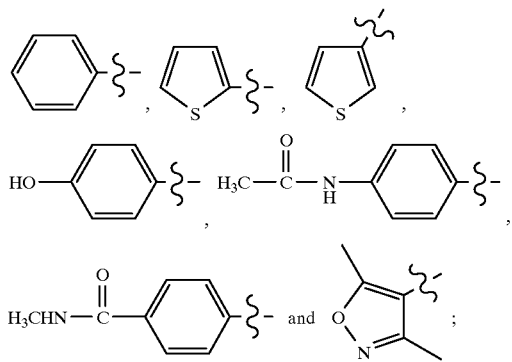

or G''' is selected from the group consisting of

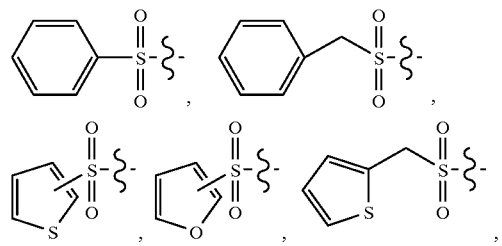

-continued
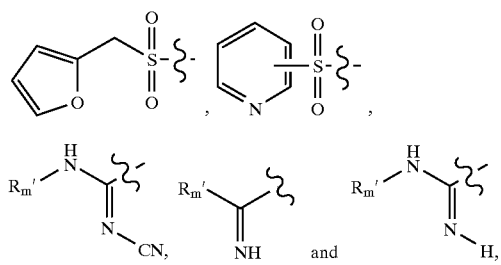
wherein $R_m'$ is selected from the group consisting of
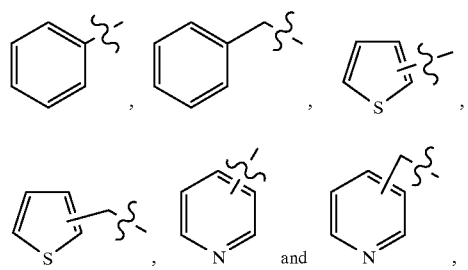
and wherein G''' is also selected from the group consisting of
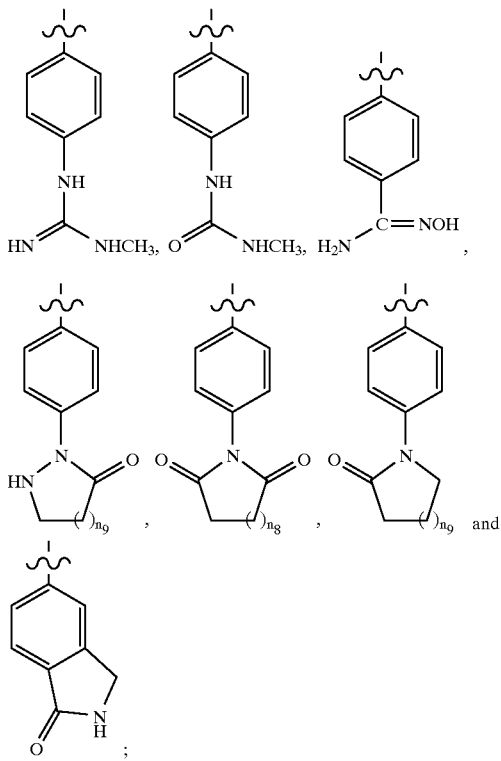
and compounds of the formula
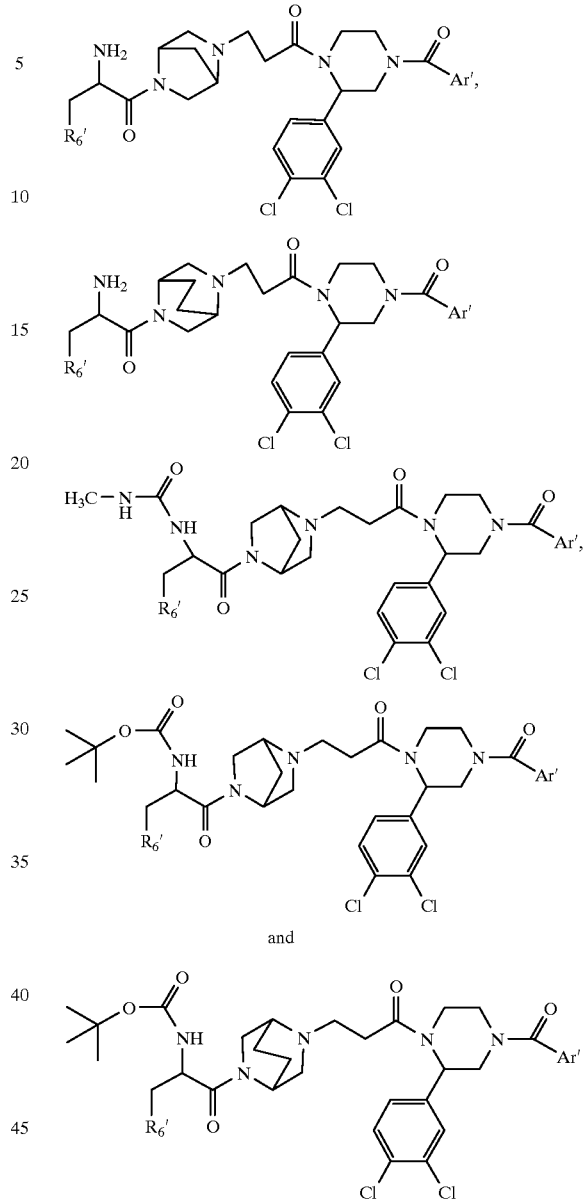
wherein $R_6'$ is as defined above and wherein Ar' is selected from the group consisting of
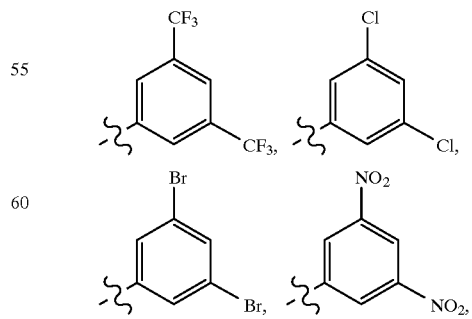

-continued
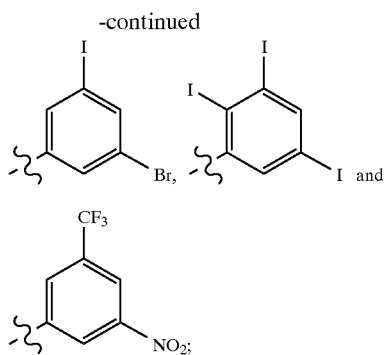
or a stereoisomer thereof, including any enantiomer, diastereomer, endo, exo, R or S form thereof, or a pharmaceutically acceptable salt thereof.
4. A compound selected from the group consisting of compounds represented by the formula
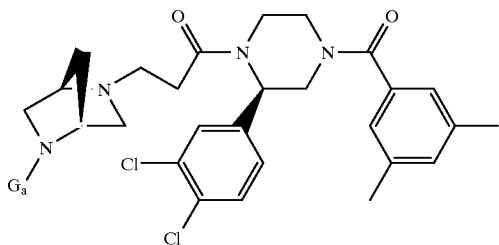
wherein $G_a$ is selected from the group consisting of
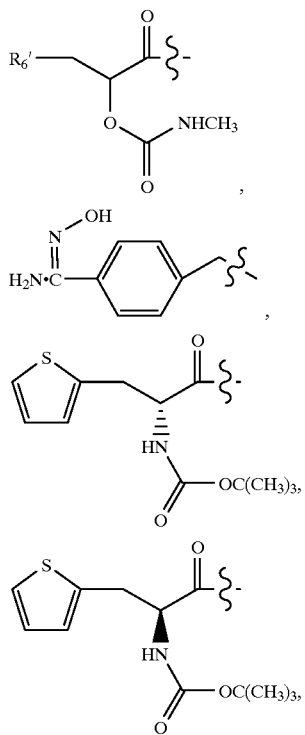
-continued
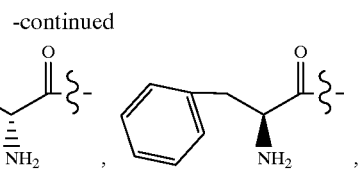
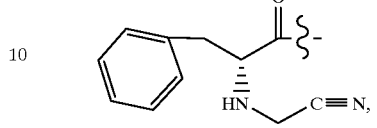
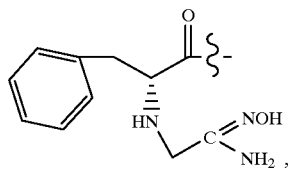
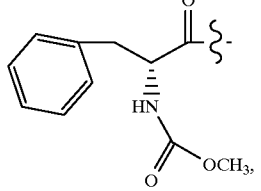
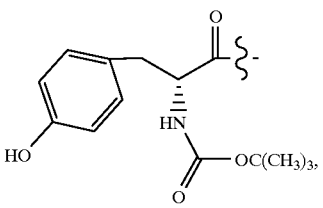
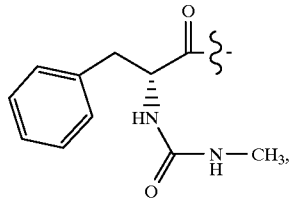
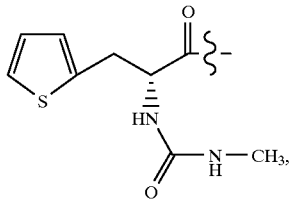
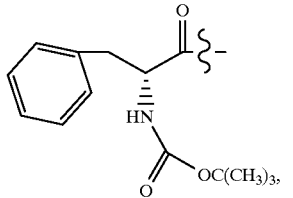
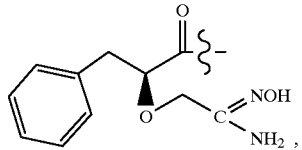

-continued

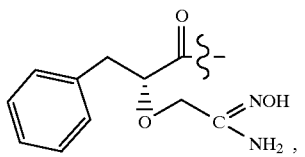

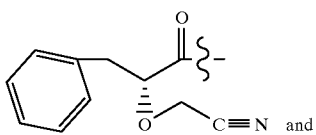

-continued

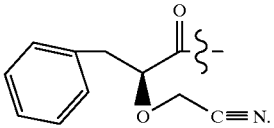

5. A pharmaceutical composition comprising a neurokinin antagonistic effective amount of a compound according to claim 1 and a pharmaceutically acceptable carrier material.

6. A method for treating asthma, bronchospasm, allergies, anxiety, depression, coughing or pain, comprising administering a therapeutically effective amount of a compound according to claim 1 to a mammal in need of such treatment.

* * * * *

UNITED STATES PATENT AND TRADEMARK OFFICE
CERTIFICATE OF CORRECTION

PATENT NO. : 5,968,929
DATED : October 19, 1999
INVENTOR(S) : David J. Blythin, et. al.

It is certified that error appears in the above-identified patent and that said Letters Patent is hereby corrected as shown below:

In column 155, line 67, after "H," insert -- $C_1$-$C_6$ alkyl, allyl, --.

In column 159, line 50, delete

"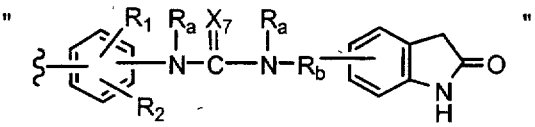"

and insert instead:

-- 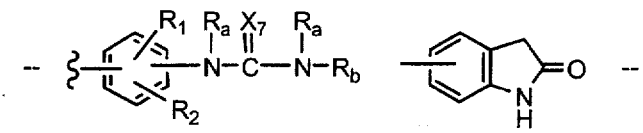 --

Signed and Sealed this

Twelfth Day of September, 2000

Attest:

Q. TODD DICKINSON

*Attesting Officer*          *Director of Patents and Trademarks*

UNITED STATES PATENT AND TRADEMARK OFFICE
CERTIFICATE OF CORRECTION

PATENT NO : 5,968,929
DATED : October 19, 1999
INVENTOR(S) : David J. Blythin, Xiao Chen, Richard J. Friary, Kevin D. McCormick, John J. Piwinski, Neng-Yang Shih, Ho-Jane Shue It is certified that error appears in the above-identified patent and that said Letters Patent are hereby corrected as shown below:

In column 158, line 15, delete

" 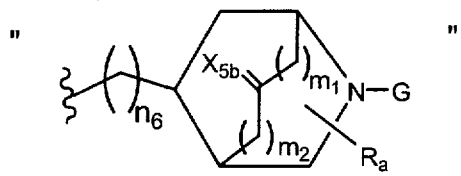 "

and insert instead

-- 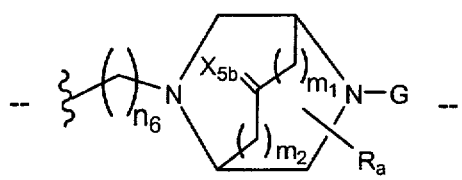 --

Signed and Sealed this

Twenty-sixth Day of December, 2000

Attest:

Q. TODD DICKINSON

*Attesting Officer*     *Director of Patents and Trademarks*